US006958148B1

(12) United States Patent
Green et al.

(10) Patent No.: US 6,958,148 B1
(45) Date of Patent: Oct. 25, 2005

(54) LINKAGE OF AGENTS TO BODY TISSUE USING MICROPARTICLES AND TRANSGLUTAMINASE

(75) Inventors: Howard Green, Brookline, MA (US); Bruce J. Compton, Lexington, MA (US); George D. Corey, Newton, MA (US); Philippe Djian, Paris (FR)

(73) Assignee: Pericor Science, Inc., Boston, MA (US)

( * ) Notice: Subject to any disclaimer, the term of this patent is extended or adjusted under 35 U.S.C. 154(b) by 0 days.

(21) Appl. No.: 09/620,783

(22) Filed: Jul. 21, 2000

Related U.S. Application Data

(63) Continuation-in-part of application No. 09/359,920, filed on Jul. 22, 1999, which is a continuation-in-part of application No. 09/234,358, filed on Jan. 20, 1999, now Pat. No. 6,267,957.
(60) Provisional application No. 60/071,908, filed on Jan. 20, 1998.

(51) Int. Cl.[7] .................. A61K 38/45; A61K 38/48; A61K 38/00; C12N 11/02; C07K 17/02
(52) U.S. Cl. ............... 424/94.5; 424/59; 424/94.63; 424/401; 435/16; 435/177; 435/193; 514/2; 530/402; 530/812
(58) Field of Search ................ 424/94.5, 94.63, 424/401, 59; 435/16, 177, 193; 514/2; 530/403, 812

(56) References Cited

U.S. PATENT DOCUMENTS

| | | | |
|---|---|---|---|
| 3,867,365 A | 2/1975 | Stahmann et al. | |
| 3,979,508 A | 9/1976 | Stahmann et al. | |
| 3,990,459 A | 11/1976 | Papantoniou | |
| 4,048,301 A | 9/1977 | Papantoniou | |
| 4,152,411 A | 5/1979 | Schall, Jr. | |
| 4,277,460 A | 7/1981 | Kojima et al. | |
| 4,279,996 A | 7/1981 | Yoshioka et al. | 435/69 |
| 4,284,537 A | 8/1981 | Beachey | |
| 4,338,214 A | 7/1982 | Fischer et al. | 252/545 |
| 4,352,883 A | 10/1982 | Lim | 435/178 |
| 4,356,166 A | 10/1982 | Peterson et al. | 525/54.1 |
| 4,357,259 A | 11/1982 | Senyei et al. | 264/4.3 |
| 4,369,037 A | 1/1983 | Matsunaga et al. | 8/127.51 |
| 4,407,965 A | 10/1983 | Yanaihara | |
| 4,517,175 A | 5/1985 | Iwabuchi et al. | 424/70 |
| 4,521,334 A | 6/1985 | Beachey | |
| 4,532,207 A | 7/1985 | Brewer et al. | |
| 4,534,881 A | 8/1985 | Sikes et al. | |
| 4,543,325 A | 9/1985 | Albert et al. | |
| 4,568,559 A | 2/1986 | Nuwayser et al. | 427/3 |
| 4,572,800 A | 2/1986 | Shimizu et al. | |
| 4,597,967 A | 7/1986 | Beachey | |
| 4,626,495 A | 12/1986 | Sakaguchi | |
| 4,631,190 A | 12/1986 | Shen et al. | |
| 4,645,503 A | 2/1987 | Lin et al. | |
| 4,663,286 A | 5/1987 | Tsang et al. | |
| 4,671,954 A | 6/1987 | Goldberg et al. | 424/450 |
| 4,680,338 A | 6/1987 | Sundoro | |
| 4,695,562 A | 9/1987 | Beachey et al. | |
| 4,699,778 A | 10/1987 | Marty | 424/59 |
| 4,701,521 A | 10/1987 | Ryser et al. | |
| 4,705,682 A | 11/1987 | Moeller et al. | 525/70 |
| 4,726,942 A | 2/1988 | Lang et al. | 424/47 |
| 4,728,639 A | 3/1988 | Beachey | |
| 4,741,872 A | 5/1988 | De Luca et al. | 264/4.7 |
| 4,744,933 A | 5/1988 | Rha et al. | 264/4.3 |
| 4,749,620 A | 6/1988 | Rha et al. | |

(Continued)

FOREIGN PATENT DOCUMENTS

| | | |
|---|---|---|
| AU | A-13742 | 9/1988 |
| CA | 2094658 | 10/1993 |
| CA | 2245310 A1 | 2/1999 |
| DE | 4335025 A1 | 4/1995 |
| DE | 19647863 A | 5/1998 |
| EP | 0 009 498 B1 | 8/1979 |
| EP | 0107053 A2 | 5/1984 |
| EP | 0111385 A2 | 6/1984 |
| EP | 015898 A2 | 8/1985 |
| EP | 0188309 A2 | 7/1986 |
| EP | 0285 474 | 10/1988 |
| EP | 0 354 847 A2 | 2/1990 |
| EP | 0359996 A2 | 3/1990 |
| EP | 0421478 A2 | 4/1991 |
| EP | 0481 504 | 10/1991 |
| EP | 0499164 A1 | 8/1992 |
| EP | 0511 116 | 10/1992 |
| EP | 0 599 303 A2 | 6/1994 |

(Continued)

OTHER PUBLICATIONS

International Search Report for PCT/US00/20211, mailed Nov. 15, 2000.
Asayama, et al. "Synthesis of Novel Polyampholyte Comb–Type Copolymers Consisting of a Poly(L–lysine) Backbone and Hyaluronic Acid Side Chains for a DNA Carrier," Bioconjugate Chem., 1998, vol. 9, pp. 476–481.
Maruyama, et al. "Nanoparticle DNA Carrier with Poly(L–l–ysine) Grafted Polysaccharide Copolymer and Poly(D,L–lactic acid)," Bioconjugate Chem., 1997, vol. 8, pp. 735–742.
Maruyama, et al. "Comb–Type Polycations Effectively Stabilize DNA Triplex," Bioconjugate Chem. 1997, vol. 8, pp. 3–6.
Wagner, et al. "Transferrin–polycation conjugates as carriers for DNA uptake into cells," 1998, Proc. Natl. Acad. Sci. USA, vol. 87, pp. 3410–3414.

(Continued)

Primary Examiner—David M. Naff
(74) Attorney, Agent, or Firm—Wolf, Greenfield & Sacks, P.C.

(57) ABSTRACT

Methods, products and kits are provided for attaching agents to a body tissue surface via microparticles using endogenous or exogenous transglutaminase. The microparticles have surface available transglutaminase substrate reactive groups. In an embodiment, the groups are part of a polymer containing at least two contiguous linked lysines or at least three contiguous linked glutamines.

39 Claims, 1 Drawing Sheet

U.S. PATENT DOCUMENTS

| | | | |
|---|---|---|---|
| 4,832,946 A | 5/1989 | Green | 424/70 |
| 4,834,978 A | 5/1989 | Nuwayser | 424/448 |
| 4,839,168 A | 6/1989 | Abe et al. | 424/74 |
| 4,847,240 A | 7/1989 | Ryser et al. | |
| 4,879,116 A | 11/1989 | Fox et al. | 424/682 |
| 4,880,911 A | 11/1989 | Brewer et al. | |
| 4,885,169 A | 12/1989 | Gazzani | 424/104 |
| 4,892,733 A | 1/1990 | Bichon et al. | |
| 4,908,404 A | 3/1990 | Benedict et al. | |
| 4,973,473 A | 11/1990 | Schneider et al. | 424/63 |
| 5,017,229 A | 5/1991 | Burns et al. | |
| 5,075,019 A | 12/1991 | Evans et al. | 508/260 |
| 5,080,888 A | 1/1992 | Grollier et al. | 424/61 |
| 5,091,173 A | 2/1992 | Buultjens et al. | 424/70 |
| 5,098,833 A | 3/1992 | Lasky et al. | |
| 5,100,673 A | 3/1992 | Bader et al. | |
| 5,100,956 A | 3/1992 | O'Lenick, Jr. | 514/54.1 |
| 5,116,320 A | 5/1992 | Lo Duca | |
| 5,132,230 A | 6/1992 | Rosenthal et al. | |
| 5,135,913 A | 8/1992 | Pickart | 424/16 |
| 5,145,675 A | 9/1992 | Won | 424/78.31 |
| 5,156,959 A | 10/1992 | Abrahmsen et al. | 435/69.1 |
| 5,162,505 A | 11/1992 | Dean et al. | |
| 5,166,320 A | 11/1992 | Wu et al. | |
| 5,175,112 A | 12/1992 | Amiral et al. | |
| 5,202,431 A | 4/1993 | della Valle et al. | 536/55.1 |
| 5,206,012 A | 4/1993 | Farer et al. | 424/69 |
| 5,232,984 A | 8/1993 | Hubbell et al. | |
| 5,246,780 A | 9/1993 | Farer et al. | 428/404 |
| 5,258,041 A | 11/1993 | Guire et al. | |
| 5,263,992 A | 11/1993 | Guire | |
| 5,264,207 A | 11/1993 | Bommelaer et al. | 424/69 |
| 5,271,961 A | 12/1993 | Mathiowitz et al. | 427/213.31 |
| 5,286,629 A | 2/1994 | Denis et al. | 435/7.1 |
| 5,334,640 A | 8/1994 | Desai et al. | |
| 5,354,844 A | 10/1994 | Beug et al. | |
| 5,358,706 A | 10/1994 | Marlin et al. | |
| 5,366,958 A | 11/1994 | Weiner et al. | |
| 5,405,939 A | 4/1995 | Suhadolnik et al. | |
| 5,409,904 A | 4/1995 | Hecht et al. | |
| 5,436,291 A | 7/1995 | Levy et al. | |
| 5,461,081 A | 10/1995 | Ali et al. | |
| 5,470,829 A | 11/1995 | Prisell et al. | |
| 5,470,956 A | 11/1995 | Hayashi et al. | |
| 5,487,977 A | 1/1996 | de Weck | |
| 5,490,980 A | 2/1996 | Richardson et al. | 424/94.6 |
| 5,494,682 A | 2/1996 | Cohen et al. | 424/489 |
| 5,501,863 A | 3/1996 | Röet al. | |
| 5,505,952 A | 4/1996 | Jiang et al. | |
| 5,510,329 A | 4/1996 | Belkin et al. | |
| 5,521,291 A | 5/1996 | Curiel et al. | |
| 5,523,222 A | 6/1996 | Page et al. | |
| 5,525,336 A | 6/1996 | Green et al. | 424/94.5 |
| 5,548,064 A | 8/1996 | Russell-Jones et al. | |
| 5,559,104 A | 9/1996 | Romeo et al. | |
| 5,573,934 A | 11/1996 | Hubbell et al. | |
| 5,576,188 A | 11/1996 | Schlaeppi et al. | |
| 5,578,442 A | 11/1996 | Desai et al. | |
| 5,578,598 A | 11/1996 | Abe et al. | |
| 5,587,175 A | 12/1996 | Viegas et al. | |
| 5,587,301 A | 12/1996 | Hawkins et al. | |
| 5,591,648 A | 1/1997 | Hayashi et al. | |
| 5,593,658 A | 1/1997 | Bogdanov et al. | |
| 5,595,893 A | 1/1997 | Pometto, III et al. | |
| 5,595,897 A | 1/1997 | Midoux et al. | |
| 5,614,212 A | 3/1997 | D'Angelo et al. | 424/449 |
| 5,620,013 A | 4/1997 | Bretton | |
| 5,629,011 A | 5/1997 | Illum | |
| 5,629,021 A | 5/1997 | Wright | 424/489 |
| 5,633,230 A | 5/1997 | Twist et al. | |
| 5,635,380 A | 6/1997 | Naftilan et al. | |
| 5,635,383 A | 6/1997 | Wu et al. | |
| 5,635,385 A | 6/1997 | Leopold et al. | |
| 5,635,447 A | 6/1997 | Sanders | |
| 5,646,133 A | 6/1997 | Sanders | |
| 5,643,672 A | 7/1997 | Marchi et al. | 428/402 |
| 5,646,120 A | 7/1997 | Sumner-Smith et al. | |
| 5,656,609 A | 8/1997 | Wu et al. | |
| 5,658,592 A | 8/1997 | Tanihara et al. | |
| 5,658,915 A | 8/1997 | Abe et al. | |
| 5,660,851 A | 8/1997 | Domb | |
| 5,661,040 A | 8/1997 | Huff et al. | |
| 5,674,849 A | 10/1997 | Twist et al. | |
| 5,674,977 A | 10/1997 | Gariépy | |
| 5,677,276 A | 10/1997 | Dickerson et al. | |
| 5,679,377 A | 10/1997 | Bernstein et al. | 424/491 |
| 5,681,568 A | 11/1997 | Goldin et al. | |
| 5,686,113 A | 11/1997 | Speaker et al. | 424/490 |
| 5,688,527 A | 11/1997 | Bordier et al. | 424/450 |
| 5,693,509 A | 12/1997 | Cotton et al. | |
| 5,693,851 A | 12/1997 | Sielcken et al. | |
| 5,705,270 A | 1/1998 | Soon-Shiong et al. | |
| 5,711,915 A | 1/1998 | Siegmund et al. | |
| 5,716,614 A | 2/1998 | Katz et al. | |
| 5,718,900 A | 2/1998 | Hill et al. | |
| 5,723,301 A | 3/1998 | Burke et al. | |
| 5,733,572 A | 3/1998 | Unger et al. | 424/450 |
| 5,738,864 A | 4/1998 | Schacht et al. | |
| 5,744,156 A | 4/1998 | De Lacharriere et al. | 424/445 |
| 5,756,069 A | 5/1998 | Torchilin et al. | |
| 5,760,200 A | 6/1998 | Miller et al. | |
| 5,763,160 A | 6/1998 | Wang | |
| 5,766,585 A | 6/1998 | Evans et al. | |
| 5,770,229 A | 6/1998 | Tanihara et al. | |
| 5,770,628 A | 6/1998 | Cantoro | |
| 5,773,577 A | 6/1998 | Cappello | 530/350 |
| 5,780,054 A | 7/1998 | Tardi et al. | |
| 5,783,178 A | 7/1998 | Kabanov et al. | |
| 5,783,566 A | 7/1998 | Mislick | |
| 5,783,669 A | 7/1998 | Hawkins et al. | |
| 5,783,691 A | 7/1998 | Malson et al. | |
| 5,785,977 A | 7/1998 | Breithbarth | 424/401 |
| 5,788,959 A | 8/1998 | Singh | |
| 5,789,230 A | 8/1998 | Cotton et al. | |
| 5,789,531 A | 8/1998 | Sumner-Smith et al. | |
| 5,792,645 A | 8/1998 | Beug et al. | |
| 5,795,860 A | 8/1998 | Witt et al. | |
| 5,795,909 A | 8/1998 | Shashoua et al. | |
| 5,817,644 A | 10/1998 | Gustafson | |
| 5,820,882 A | 10/1998 | Hubbell et al. | |
| 5,830,731 A | 11/1998 | Seed et al. | |
| 5,830,913 A | 11/1998 | Ogawa et al. | |
| 5,831,001 A | 11/1998 | Twist et al. | |
| 5,834,444 A | 11/1998 | Falk et al. | |
| 5,834,556 A | 11/1998 | Desai et al. | |
| 5,837,533 A | 11/1998 | Boutin | |
| 5,837,747 A | 11/1998 | Soon-Shiong et al. | |
| 5,842,477 A | 12/1998 | Naughton et al. | |
| 5,843,770 A | 12/1998 | Ill et al. | |
| 5,846,530 A | 12/1998 | Soon-Shiong et al. | 424/93.7 |
| 5,846,951 A | 12/1998 | Gregoriadis et al. | |
| 5,849,839 A | 12/1998 | Hubbell et al. | |
| 5,851,229 A | 12/1998 | Lentz et al. | |
| 5,851,527 A | 12/1998 | Hansen | |
| 5,856,435 A | 1/1999 | Bazile et al. | 530/300 |
| 5,858,746 A | 1/1999 | Hubbell et al. | |
| 5,861,149 A | 1/1999 | Ritter | 424/78.06 |
| 5,861,156 A | 1/1999 | George et al. | |
| 5,863,990 A | 1/1999 | Papisov | 525/398 |
| 5,869,466 A | 2/1999 | Russell-Jones et al. | |
| 5,871,710 A | 2/1999 | Bogdanov et al. | |

| | | | | | | |
|---|---|---|---|---|---|---|
| 5,871,722 A | 2/1999 | Nacht et al. ............. 424/78.03 | | 6,166,130 A | 12/2000 | Rhee et al. |
| 5,874,064 A | 2/1999 | Edwards et al. ............... 424/46 | | 6,177,257 B1 | 1/2001 | Macphee et al. |
| 5,874,297 A | 2/1999 | Wu et al. | | 6,177,259 B1 | 1/2001 | Yuan et al. |
| 5,874,500 A | 2/1999 | Rhee et al. | | 6,200,595 B1 | 3/2001 | Motoyashiki et al. |
| 5,876,698 A | 3/1999 | Schmitt-Willich et al. | | 6,221,397 B1 | 4/2001 | Russell-Jones et al. |
| 5,876,744 A | 3/1999 | Della Valle et al. | | 6,221,959 B1 | 4/2001 | Kabanov et al. |
| 5,882,645 A | 3/1999 | Toth et al. | | 6,224,893 B1 | 5/2001 | Langer et al. |
| 5,885,609 A | 3/1999 | Amiji | | 6,229,009 B1 | 5/2001 | Lambert et al. |
| 5,902,795 A | 5/1999 | Toole et al. | | 6,235,313 B1 | 5/2001 | Mathiowitz et al. |
| 5,913,884 A | 6/1999 | Trauner et al. ............... 607/88 | | 6,235,726 B1 | 5/2001 | Burns et al. |
| 5,922,859 A | 7/1999 | Birnstiel et al. | | 6,251,392 B1 | 6/2001 | Hein et al. |
| 5,925,626 A | 7/1999 | della Valle et al. | | 6,251,599 B1 | 6/2001 | Chen et al. |
| 5,935,586 A | 8/1999 | De Lacharriere et al. ... 424/401 | | 6,267,957 B1 * | 7/2001 | Green et al. ............... 424/94.5 |
| 5,939,323 A | 8/1999 | Valentini et al. | | 6,271,216 B1 | 8/2001 | Mello et al. |
| 5,939,453 A | 8/1999 | Heller et al. ................. 514/452 | | 6,271,344 B1 | 8/2001 | Turley |
| 5,945,100 A | 8/1999 | Fick | | 6,280,745 B1 | 8/2001 | Flore et al. |
| 5,955,109 A | 9/1999 | Won et al. ................... 424/501 | | 6,281,192 B1 | 8/2001 | Leahy et al. |
| 5,955,578 A | 9/1999 | Pierschbacher et al. | | 6,281,341 B1 | 8/2001 | Mares-Guia et al. |
| 5,962,015 A | 10/1999 | Delrieu et al. | | 6,303,752 B1 | 10/2001 | Olsen et al. |
| 5,962,018 A | 10/1999 | Curtis et al. ................. 424/450 | | 6,306,993 B1 | 10/2001 | Rothbard et al. |
| 5,965,152 A | 10/1999 | Galin et al. | | 6,323,278 B2 | 11/2001 | Rhee et al. |
| 5,965,404 A | 10/1999 | Buschle et al. | | 6,331,289 B1 | 12/2001 | Klaveness et al. |
| 5,965,493 A | 10/1999 | Grieco et al. | | 6,348,508 B1 | 2/2002 | Denick, Jr. et al. |
| 5,965,532 A | 10/1999 | Bachovchin | | 6,353,022 B1 | 3/2002 | Schneider et al. |
| 5,968,500 A | 10/1999 | Robinson | | 6,353,055 B1 | 3/2002 | Kabanov et al. |
| 5,968,542 A | 10/1999 | Tipton | | 6,355,690 B1 | 3/2002 | Tsuji |
| 5,968,543 A | 10/1999 | Heller et al. ................. 424/425 | | 6,368,586 B1 | 4/2002 | Jacob et al. |
| 5,972,326 A | 10/1999 | Galin et al. | | 6,378,527 B1 | 4/2002 | Hungerford et al. |
| 5,972,707 A | 10/1999 | Roy et al. | | 6,379,965 B1 | 4/2002 | Boutin |
| 5,980,883 A | 11/1999 | Tanihara et al. | | 6,387,390 B1 | 5/2002 | Deaver et al. |
| 5,981,719 A | 11/1999 | Woiszwillo et al. ......... 530/410 | | 6,395,029 B1 | 5/2002 | Levy |
| 5,985,354 A | 11/1999 | Mathiowitz et al. ........ 427/2.21 | | 6,420,519 B1 | 7/2002 | Hwang et al. |
| 5,990,095 A | 11/1999 | Falk et al. | | 6,511,957 B1 * | 1/2003 | Green et al. .................... 514/2 |
| 5,993,805 A | 11/1999 | Sutton et al. ............... 424/94.1 | | 2001/0031740 A1 | 10/2001 | Unger et al. |
| 5,993,856 A | 11/1999 | Ragavan et al. | | 2001/0039336 A1 | 11/2001 | Miller et al. |
| 5,994,311 A | 11/1999 | Eichner et al. | | 2002/0013408 A1 | 1/2002 | Rhee et al. |
| 5,998,588 A | 12/1999 | Hoffman et al. | | 2002/0016304 A1 | 2/2002 | Maruyama et al. |
| 6,005,004 A | 12/1999 | Katz et al. ................... 514/549 | | 2002/0019439 A1 | 2/2002 | Grieco et al. |
| 6,007,816 A | 12/1999 | St. John et al. | | 2002/0052000 A1 | 5/2002 | Parthasarathy et al. |
| 6,013,641 A | 1/2000 | Lussow et al. | | | | |
| 6,020,200 A | 2/2000 | Enevold ...................... 435/382 | | FOREIGN PATENT DOCUMENTS | | |
| 6,022,735 A | 2/2000 | Curiel et al. | | EP | 0615 745 | 9/1994 |
| 6,022,866 A | 2/2000 | Falk et al. | | EP | 0693293 A1 | 1/1996 |
| 6,025,138 A | 2/2000 | Hawkins et al. | | EP | 0704 221 | 4/1996 |
| 6,025,337 A | 2/2000 | Truong et al. ................. 514/44 | | EP | 0725141 A1 | 8/1996 |
| 6,027,741 A | 2/2000 | Cialdi, et al. | | EP | 0727223 A1 | 8/1996 |
| 6,030,954 A | 2/2000 | Wu et al. | | EP | 0808844 A2 | 11/1997 |
| 6,030,958 A | 2/2000 | Burns et al. | | EP | 0950406 A2 | 10/1999 |
| 6,033,677 A | 3/2000 | Cabane et al. ............... 424/401 | | EP | 0992794 A2 | 4/2000 |
| 6,037,329 A | 3/2000 | Baird et al. | | EP | 0999278 A1 | 5/2000 |
| 6,037,467 A | 3/2000 | Stahl et al. | | EP | 1067116 A1 | 1/2001 |
| 6,045,835 A | 4/2000 | Soper et al. .................... 424/89 | | EP | 1067117 A1 | 1/2001 |
| 6,054,312 A | 4/2000 | Larocca et al. | | EP | 1067173 A1 | 1/2001 |
| 6,054,313 A | 4/2000 | Bryan et al. | | EP | 1067174 A1 | 1/2001 |
| 6,066,328 A | 5/2000 | Ribier et al. ................. 424/401 | | FR | 2092875 A | of 1972 |
| 6,069,133 A | 5/2000 | Chiou et al. | | FR | 2659352 | 9/1991 |
| 6,077,663 A | 6/2000 | Curiel et al. | | FR | 2719316 A1 | 11/1995 |
| 6,086,863 A | 7/2000 | Ritter et al. | | GB | 2038628 A | 7/1980 |
| 6,089,234 A | 7/2000 | Bretton et al. | | GB | 2185397 A | 7/1987 |
| 6,103,525 A | 8/2000 | Stern et al. | | JP | 57163318 A | 10/1982 |
| 6,107,326 A | 8/2000 | Jori | | JP | 58225028 A | 12/1983 |
| 6,110,208 A | 8/2000 | Soranzo et al. | | JP | 61073665 A | 4/1986 |
| 6,123,965 A | 9/2000 | Jacob et al. | | JP | 61172807 | 8/1986 |
| 6,127,170 A | 10/2000 | Boutin | | JP | 63253028 A | 10/1988 |
| 6,127,448 A | 10/2000 | Domb | | JP | 1097861 A | 4/1989 |
| 6,129,956 A | 10/2000 | Morra et al. | | JP | 2-204407 | 2/1990 |
| 6,132,462 A | 10/2000 | Li | | JP | 02169511 | 6/1990 |
| 6,136,793 A | 10/2000 | Falk et al. | | JP | 2193914 A | 7/1990 |
| 6,138,680 A | 10/2000 | Bretton | | JP | 03038511 | 2/1991 |
| 6,150,461 A | 11/2000 | Takei et al. | | JP | 03083908 | 4/1991 |
| 6,159,955 A | 12/2000 | Asculai et al. | | JP | 4215760 A | 8/1992 |

| | | |
|---|---|---|
| JP | 4244015 A | 9/1992 |
| JP | 05085924 | 4/1993 |
| JP | 5-56785 | 5/1993 |
| JP | 7216000 A | 8/1995 |
| WO | WO 79/00515 | 8/1979 |
| WO | WO90/13256 A1 | 11/1990 |
| WO | WO91/04058 | 4/1991 |
| WO | WO 91/09958 | 7/1991 |
| WO | WO 91/15193 | 10/1991 |
| WO | WO91/17761 A1 | 11/1991 |
| WO | WO 92/07871 | 5/1992 |
| WO | WO 92/12238 | 7/1992 |
| WO | WO 93/04701 | 3/1993 |
| WO | WO 9309176 A2 | 5/1993 |
| WO | WO93/16733 | 9/1993 |
| WO | WO 93/21941 | 11/1993 |
| WO | WO 94/14464 | 7/1994 |
| WO | WO 94/18945 | 9/1994 |
| WO | WO 94/23738 | 10/1994 |
| WO | WO 95/11038 | 4/1995 |
| WO | WO 95/23611 A1 | 9/1995 |
| WO | WO 95/24929 | 9/1995 |
| WO | WO 9530020 A1 | 11/1995 |
| WO | WO 96/11990 | 4/1996 |
| WO | WO96/12405 A1 | 5/1996 |
| WO | WO 96/21036 | 7/1996 |
| WO | WO 97/33552 | 9/1997 |
| WO | WO 97/40854 | 11/1997 |
| WO | WO 97/41215 | 11/1997 |
| WO | WO 98/13381 | 4/1998 |
| WO | WO98/35056 A1 | 8/1998 |
| WO | WO 98/52614 | 11/1998 |
| WO | WO99/02683 A1 | 1/1999 |
| WO | WO 99/36570 | 7/1999 |
| WO | WO 01/06829 | 2/2001 |
| WO | WO 01/07009 | 2/2001 |
| WO | WO 01/13957 | 3/2001 |
| WO | WO 01/32850 A1 | 5/2001 |
| WO | WO 01/62297 | 8/2001 |

OTHER PUBLICATIONS

Lemaitre, et al. "Specific antiviral activity of a poly(L–lysine)–conjugated oligodeoxyribonucleotide sequence complementary to vesicular stomatitis virus N protein mRNA initiation site," 1987, Proc. Natl. Acad. Sci. USA, vol. 84, pp. 648–652 Abstract.

Zheng, et al., "Production of microspheres with surface amino groups from blends of poly(lactide–co–glycolide) and poly(C–EBZ–L–lysine) and use of encapsulation", *Biotechnol. Prog.*, 15(4):763–7 (1999).

Polysciences, Inc., Technical Data Sheet #238C–238E (2000).

Sol–Gel Technology (2000).

Caponetti, et al., "Microparticles of novel branch copolymers of lactic acid and amino acids:preparation and characterization", *J. Pharm. Sci.*, 88(1):136–41 (1999) ABSTRACT.

Capan, et al., "Influence of formulation parameters on the characteristics of poly(D,L–lactide–co–glycolide) microspheres containing poly(L–lysine) complexed plasmid DNA", *J. Controlled Release*, 60(2–3):279–86 (1999) ABSTRACT.

Maruyama, et al., "Nanoparticle DNA carrier with poly(L–l-ysine) grafted polysaccharide copolymer and poly(D,L–lactic acid", *Bioconjug Chem.*, 8(5):735–42 (1997) ABSTRACT.

NCB1 Accession No. JC 4660—serum albumin precusor—cat, Feb. 16, 1997.

NCB1 Accession No. AAA 30988—albumin, Apr. 27, 1993.

NCB1 Accession No. T05737—probably hardein C.—barley, Aug. 20, 1999.

NCB1 Accession No. P04701—Zein–Alpha precurso (clone Z4), Feb. 15, 2000.

NCB1 Accession No. P14692—Kafirin PSK8 precursor, Feb. 15, 2000.

NCB1 Accession No. T06500—alpha/beta gliadin A–IV precursor—wheat, Aug. 20, 1999.

Seradyn Specification Sheet for Microparticles (2000) pp. 1–5.

*Women's Wear Daily,* p. 6 (Abstract) (1992).

Banks–Schlegal, *J. of Cell Biology,* 90:732, 737 (1981).

Davies, et al., *Adv. Exp. Med. Biol.* 250, 391–401 (1988).

Eckert, *Cell,* 46:583–589 (1986).

Etoh, *Biochem. Biophys Res Comm,* 136:51–56 (1986).

Fietz, *J. of Cell Biol.*, 110:427–436 (1990).

Folk 17A: 889–894, (1970) Tabor, H and C. Tabor Eds.

Green, *Cell,* 11:405–416 (1977).

Greenberg, *FASEB J.*, 5:3071–3077 (1991).

Highley, *Cosmetics & Toiletries,* 99:57–62 (1984).

Hohl, *J. of Biol. Chem.,* 266:6626–6636 (1991).

Hohl, *Dermatologica,* 180:201–211 (1990).

Kahlem, et al., *Proc. Natl. Acad. Sci. USA,* 93:14580–14585 (1996).

Kvedar, *Differentiation,* 49:195–204 (1992).

Lajemi, M., et al., *Histochemical Journal* 29:593–606 (1997).

Markova, *Mol and Cell Biol,* 13:613–625 (1993).

Marvin, *Biochem.*, 89:11029–11030 (1992).

Mehrel, *Cell,* 61:1103–1112 (1990).

Phillips, *Biochem.,* 87:9333–9337 (1990).

Pober, et al., *Biochem.,* 17:11:2163–2169 (1978).

Rialdi et al., *Cosmetics & Toiletries,* 103:89–94 (1988).

Rice, *Cell,* 18:681–694 (1979).

Rice, *Cell,* 11:417–422 (1977).

Simon, *Cell,* 40:677–683 (1985).

Steven, *J. of Structural Biology,* 104:150–162 (1990).

Steven, M. et al., *J. Cell Science,* 107:693–700 (1994).

Jian et al., *Biosci. Biotech. and Biochem.,* 61(1):188–190, 1997 Abstract only.

<No Author Listed> *Chemical Abstracts,* 89:18 (1978).

<No Author Listed> *Chemical Abstracts,* 89:292 (1978).

Nogawa et al., *Proceed. Int'l. Symp. Control. Rel. Bioact. Mater.,* 26:821–822, 1999.

Blackwell et al., *Federation Proceedings,* 36(1):98–101, 1973.

Smith et al., *Arthritis & Rheumatism,* 37(1):125–136, 1994.

Hembry et al., *Am. J. Path.* 143(2):628–642, 1993.

Park et al., *Proceed. Int'l. Symp. Control. Rel. Bioact. Mater.,* 26:823–824, 1999.

Anderson, *Annals New York Academy of Sciences, Dept of Pathology and Macromolecular Science, Case Western Reserve University, Cleveland Ohio, 44106,* "Poly (amino acids)", pp67–75.

Li et al., *Cancer Res,* 58:2404–2409, 1981.

Cera et al., *Anti–Cancer Drug Design,* 7:143–151, 1992.

Park et al., *Prep Biochem Biotechnol,* 29(4):353–370, 1999 Abstract only.

Hu et al., *Tissue Engineering,* 6(6):558–593(9), 2000.

Mayurama, et al., *Bioconjug Chem,* 9(2):292–299, 1998 Abstract only.

Asayama et al., *Bioconjug Chem,* 10(2):246–253, 1999 Abstract only.

Hu et al., *J. Biomed Mat Res*, 47(1):79–84, 1999 Abstract only.

Zu, et al., *J. Biosci, Biotech Biochem*, 61(1):188–190, 1997.

Asayama et al., *Bioconjug Chem*, 9:476–481, 1998.

Kabanov, A.V., et al. "DNA Complexes with Polycations for the Delivery of Genetic Material into Cells" Bioconjugate Chem., 1995, vol. 6, pp. 7–20.

Lebaron, R.G., et al. "Hyaluronic Acid Binding Properties of Versican" J Biol Chem, vol. 267, No. 14, pp. 10003–100. Abstract.

Peach, R.J., et al., "Identification of Hyaluronic Acid Binding Sites in the Extracellular Domain of CD44" J Cell Biol., 1993 Jul; vol. 122, No. 1, pp. 257–264. Abstract.

Degols, G, et al., "Oligonucleotide–poly(L–lysine)–Heparin Complexes: Potent Sequence–Specific Inhibitors of HIV–1 infection" Bioconjugate Chem. 1994 Jan–Feb; Vol. 5, No. 1, pp. 8–13, Abstract.

Shen, W.C., et al., "Poly(L–lysine) has Different Membrane Transport and Drug–Carrier Properties when Complexed with Heparin" Proc. Natl Acad Sci USA, 1981, vol. 78, No. 12, pp. 7589–7593, Abstract.

Delmage, J.M., et al. "The selective Suppression of Immunogenicity by Hyaluronic Acid," Ann Clin Lab Sci, 1986 Jul–Aug, vol. 16, No. 4, pp. 303–310. Abstract.

Abuchowski, A., et al. "Effect of Covalent Attachment of Polyethylene Glcol on Immunogenicity and Circulating Life of Bovine Liver Catalase," J Biol Chem., 1977 Jun 10; vol. 252, No. 11, pp. 3582–3586, Abstract.

Wu, G. Y., et al. "Evidence for Targeted Gene Delivery to Help G2 Hepatoma Cells in Vitro," Biochemistry, 1988 Feb 9., vol. 27, No. 3, pp. 887–892, Abstract.

\* cited by examiner

LINKAGE OF AGENTS TO BODY TISSUE USING MICROPARTICLES AND TRANSGLUTAMINASE

RELATED APPLICATIONS

This application is a continuation-in-part of application Ser. No. 09/359,920, filed Jul. 22, 1999 (pending), which is a continuation-in-part of application Ser. No. 09/234,358, filed Jan. 20, 1999, now U.S. Pat. No. 6,267,957, which claims benefit to provisional application No. 60/071,908, filed Jan. 20, 1998, which applications are incorporated herein in their entirety.

FIELD OF THE INVENTION

This invention relates to the delivery of agents to tissue using microparticles and involves methods, products and kits relating thereto.

BACKGROUND OF THE INVENTION

Transglutaminases are a family of calcium-dependent enzymes mediating covalent cross-linking reactions between specific peptide bound γ-glutamyl residues and various primary amino groups of aliphatic amines, lysines or polyamines, acting as amine donor substrates (Davies, et al., *Adv. Exp. Med Biol.* 250, 391–401, 1988). These enzymes stabilize biological structures via the formation of isopeptide cross-links. In mammals, at least five enzymatically active transglutaminases have been identified, cloned and sequenced. The number of proteins acting as glutaminyl substrates for transglutaminases is restricted, and no obvious consensus sequence around these substrates' glutamines has been found.

Three main lines of investigation have been conducted surrounding transglutaminases. These enzymes have been used to label membrane proteins and, in the absence of exogenous amines, to catalyze the formation of (γ-glutamine)-lysyl cross-links between them. The labeling is quite specific and can be carried out under mild (physiological) reaction conditions. Thus, for example, transglutaminases were used to study rhodopsin in the intact disc membrane, as only residues of rhodopsin located in the aqueous phase in the exposed side of the disc membranes were expected to be labeled. In these experiments, rhodopsin was labeled by transglutaminase using putrescine and dansylcadaverine as detectable substrates.

The role of transglutaminases in living cells also has been studied, for example, using the cell-penetrating labeled substrate fluoresceincadaverine for detecting amine acceptor protein substrates accessible to active transglutaminase in living cells. A similar strategy was employed using 5-(biotinamido)-pentylamine as a label. Such labeled substrates can be detected directly, for example by fluorescence, or can be detected indirectly, for example using antibodies, to identify native proteins to which the labeled substrate has been covalently attached by transglutaminase. See, Pober, J. S. et al., *Biochemistry*, Vol. 17, No. 11:2163–2169 (1978); Lajemi, M. et al., *Histochemical Journal* 29:593–606 (1997).

More recently, an investigation was carried out to determine if polyglutamine is a transglutaminase substrate. It was determined that as long as polypeptides including stretches of polyglutamine are rendered sufficiently soluble by the flanking residues, all were excellent substrates of transglutaminase. Based upon these studies, it was speculated that certain diseases such as Spinocerebellar ataxia Type I, Machado-Joseph disease, and Dentato-Rubral pallidoluysian atrophy which are characterized by proteins having polyglutamine stretches, may arise as a result of aggregation of such proteins acted upon by a transglutaminase.

It also is described in U.S. Pat. No. 5,525,336 (the disclosure of which is incorporated herein by reference in its entirety) that transglutaminase and corneocyte proteins, the natural substrates of transglutaminases, can be used together as cosmetic treatments to cross-link preparations of corneocyte proteins to the outer layer of skin, hair or nails to form a protective layer on the skin, hair or nails.

U.S. Pat. No. 5,490,980 describes selecting agents having or modifying agents to have an aliphatic amine, and then attaching those agents to skin, hair or nails using transglutaminase. While the idea was sound in principle, in practice the '980 applicants achieved results that were barely above background. (See Example Section of '980 patent). An aliphatic amine was applied in the examples as a single linking molecule or prophetically in clusters (according to a formula in the '980 patent). In selecting the amine moiety of the pair of known transglutaminase substrate moieties, the '980 patent taught away from using the carboxamide substrate moiety.

SUMMARY OF THE INVENTION

The invention relates to microparticles and their use in delivering agents to tissues, preferably external surfaces such as skin, nails and hair. More specifically, the invention provides compositions, kits and methods for delivery of a variety of agents using microparticles which can be covalently linked to such tissues.

In one aspect, the invention provides a method of treating a subject to attach microparticles to a skin surface of the subject. The method involves contacting the skin surface with microparticles having surface available transglutaminase substrate reactive groups (i.e., carboxamide-bearing substrates or transglutaminase or aliphatic amine-bearing substrates of transglutaminase that are available (for reaction) at the surface of a microparticle) in an amount sufficient to attach the microparticles to the skin surface in the presence of endogenous transglutaminase, and allowing the microparticles to remain in contact with the skin surface for a time sufficient to permit a layer of microparticles to covalently attach to the skin surface.

In a related aspect, the invention provides a method similar to the preceding method except in the use of exogenous transglutaminase rather than endogenous transglutaminase. Thus, the method involves contacting the skin surface with microparticles having surface available transglutaminase substrate reactive groups in an amount sufficient to attach the microparticles to the skin surface in the presence of exogenous transglutaminase, applying exogenous transglutaminase to the skin surface, and allowing the microparticles and exogenous transglutaminase to remain in contact with the skin surface for a time sufficient to permit a layer of microparticles to covalently attach to the skin surface.

In one embodiment, the surface available transglutaminase substrate reactive groups comprise aliphatic amines. In a related embodiment, the surface available transglutaminase reactive groups are lysines. In another embodiment, the surface available transglutaminase substrate reactive groups comprise carboxamides. In a related embodiment, the surface available transglutaminase substrate reactive groups are glutamines. The layer of microparticles may be planar or non-planar.

In one embodiment, the microparticles further comprise an active agent. The active agent may be selected from the group consisting of a cosmetic agent, a bulking agent, a hair conditioning agent, a hair fixative, a sunscreen agent, a moisturizing agent, a depilatory agent, an anti-nerve gas agent, a film forming agent, a vitamin, an insect repellant, a coloring agent, a pharmaceutical agent, a ligand-receptor complex and a receptor of a ligand-receptor complex. In another embodiment, the active agent is not itself a substrate of transglutaminase. The active agent may be a non-nucleic acid active agent or it may be a non-protein active agent, but it is not so limited.

In yet another embodiment, the microparticles may further comprise a synthetic polymer. In one embodiment, the synthetic polymer is latex. In another embodiment, it is polystyrene. In one instance, the microparticle is porous, while in another it is hollow (i.e., a microsphere or a microcapsule). In certain embodiments, the size of the microparticle is less than 5 $\mu$m, or less than 1 $\mu$m, or 100 nm to 500 nm, or less than 100 $\mu$m, or 20 nm to 90 nm, or 20 nm to 35 nm, or less than 20 nm, or 1 nm to 10 nm, or 5 nm to 10 mm. In some embodiments, the microparticles enter the cornified layer of the skin but not the layer of living cells. However, in these latter embodiments, the agent contained within the microparticle may be able to enter the layer of living cells.

In important embodiments, the microparticles are non-biodegradable. The microparticles preferably are water insoluble and more preferably, are detergent insoluble.

In one embodiment, the transglutaminase substrate reactive groups are part of a polymer. The polymer may be a polymer of amino acid residues, non-amino acid residues, or a mixture of amino acid and non-amino acid residues, but it need not be so limited. In one embodiment, at least 50% of the residues in the polymer possess aliphatic amines or at least 50% possess carboxamides. In a related embodiment, at least 50% of the residues in the polymer are lysines or at least 50% are glutamines. The polymer may be covalently attached to the microparticle, but need not be. In one embodiment, the polymer is rich in aliphatic amines or rich in carboxamides, or rich in both, preferably at a surface available terminus or at a surface available loop. In another embodiment, the polymer is lysine-rich or glutamine-rich, or both, at a surface available terminus or at a surface available loop. In certain embodiments, the polymer comprises a polymer selected from the group consisting of at least two contiguous linked aliphatic amines or carboxamides, at least three contiguous linked aliphatic amines or carboxamides, at least four contiguous linked aliphatic amines or carboxamides, at least five contiguous linked aliphatic amines or carboxamides. In related embodiments, the polymer comprises a polymer selected from the group consisting of at least two contiguous linked lysines or glutamines, at least three contiguous linked lysines or glutamines, at least four contiguous linked lysines or glutamines, and at least five contiguous linked lysines or glutamines. In other embodiments, the polymer comprises a polymer selected from the group consisting of at least five contiguous linked aliphatic amines or carboxamides, at least ten contiguous linked aliphatic amines or carboxamides, at least fifteen contiguous linked aliphatic amines or carboxamides, at least twenty contiguous linked aliphatic amines or carboxamides, at least thirty, at least forty, at least fifty, at least 60 and at least 70 contiguous linked aliphatic amines or carboxamides. In other embodiments, the polymer comprises a polymer selected from the group consisting of at least five contiguous linked lysines or glutamines, at least ten contiguous linked lysines or glutamines, at least fifteen contiguous linked lysines or glutamines, and at least twenty contiguous linked lysines or glutamines. Many of the embodiments provided herein which relate to lysine or lysine-rich polymers apply equally to aliphatic amines and polymers rich in aliphatic amines, respectively. Similarly, many of the embodiments provided herein which relate to glutamine or glutamine-rich polymers apply equally to carboxamides and polymers rich in carboxamides.

In yet another aspect of the invention, a composition is provided that is a microparticle, preferably non-biodegradable, comprising an active agent and a polymer rich in aliphatic amine transglutaminase substrates that are preferably surface available. In an important embodiment, the microparticle comprises an active agent and a lysine-rich polymer having transglutaminase substrate reactive groups, wherein the microparticle is non-biodegradable, and the transglutaminase substrate reactive groups are surface available.

The invention further provides a composition comprising a microparticle that comprises an active agent and either a polymer rich in carboxamide transglutaminase substrates or a polymer rich in aliphatic amine transglutaminase substrates, wherein the transglutaminase substrates are preferably surface available. In one important embodiment, the microparticle comprises an active agent and a glutamine-rich polymer having transglutaminase substrate reactive groups, wherein the transglutaminase substrate reactive groups are surface available. In one embodiment, the microparticle comprises an active agent and a polymer rich in both aliphatic amines and carboxamides. Pharmaceutical preparations comprising a microparticle composition and a pharmaceutically acceptable carrier are also provided.

In one embodiment, the transglutaminase substrate reactive groups are surface available in an amount sufficient to attach the microparticle to a skin surface in the presence of endogenous transglutaminase. In another embodiment, the transglutaminase substrate reactive groups are surface available in an amount sufficient to attach the microparticle to a skin surface in the presence of exogenous transglutaminase.

In another embodiment, the microparticle is non-biodegradable. Preferably, the microparticle is water insoluble and, even more preferably, it is detergent insoluble. In certain embodiments, the microparticle is less than 5 $\mu$m, or less than 1 $\mu$m, or 100 nm to 500 nm, or less than 100 nm, or 20 nm to 90 nm, or 20 nm to 35 nm, or less than 20 nm, or 1 nm to 10 nm, or 5 nm to 10 nm. The microparticle may be porous or it may be hollow, but is not so limited.

In one embodiment, the microparticle further comprises a synthetic polymer. In one embodiment, the synthetic polymer is non-biodegradable and preferably is either latex or polystyrene. In related embodiments, the lysine-rich polymer or the glutamine-rich polymer is covalently linked to the synthetic polymer.

The glutamine-rich polymer may comprise a polymer of amino acids or a polymer of amino acid and non-amino acid residues. In one embodiment, the glutamine-rich polymer comprises at least 20%, at least 30%, at least 40% or at least 50% glutamines. Similarly, the lysine-rich polymer may comprise a polymer of amino acids or a polymer of amino acid and non-amino acid residues. In one embodiment, the lysine-rich polymer comprises at least 20%, at least 30%, at least 40% or at least 50% lysines. Polymers rich in aliphatic amines or carboxamides are similarly defined and embrace the afore-mentioned ranges (i.e., a polymer rich is aliphatic amines may comprise at least 20%, at least 30%, at least 40% or at least 50% aliphatic amines, etc.). The glutamine-rich polymer may be glutamine-rich at a surface available terminus or at a surface available loop. The lysine-rich polymer may be lysine-rich at a surface available terminus or at a surface available loop. The glutamine-rich polymer or the lysine-rich polymer may be covalently attached to the microparticle.

In certain embodiments, the glutamine-rich polymer comprises a polymer selected from the group consisting of at least five contiguous linked glutamines, at least ten contiguous linked glutamines, at least fifteen contiguous linked glutamines, and at least twenty contiguous linked glutamines. In other embodiments, the lysine-rich polymer comprises a polymer selected from the group consisting of at least two contiguous linked lysines, at least three contiguous linked lysines, at least four contiguous linked lysines, and at least five contiguous linked lysines.

In certain embodiments, the active agent is selected from the group consisting of a cosmetic agent, a bulking agent, a hair conditioning agent, a hair fixative, a sunscreen agent, a moisturizing agent, a depilatory agent, an anti-nerve gas agent, a film forming agent, a vitamin, an insect repellant, a coloring agent, a pharmaceutical agent, a ligand-receptor complex and a receptor of a ligand-receptor complex. In one embodiment, the active agent comprised within the microparticle is not itself a substrate of transglutaminase. In another embodiment, the active agent is a non-protein active agent. In yet another embodiment, the active agent is a non-nucleic acid active agent.

The invention further provides in yet another aspect, a composition comprising a microparticle comprising a non-nucleic acid active agent and covalently attached surface available transglutaminase substrate reactive groups. The microparticle size may be 100 nm to 500 nm. In other embodiments, the microparticle may be less than 100 nm in size, preferably 20 nm to 90 nm in size and even more preferably 20 nm to 35 nm in size. In yet a further embodiment, the surface available transglutaminase substrate reactive groups are free pendant groups.

The invention further provides, in other aspects, kits comprising any of the microparticles of the invention described above (or later herein), and instructions for topically administering the microparticle to a skin surface. The kits may include a microparticle comprising surface available transglutaminase substrate reactive groups in an amount sufficient to attach the microparticle to a skin surface in the presence of endogenous transglutaminase. Alternatively, the surface available transglutaminase substrate reactive groups are in an amount sufficient to attach the microparticle to a skin surface in the presence of exogenous transglutaminase. In this latter embodiment, the kit may further comprise transglutaminase. In either kit, the microparticle may be provided in a topically administered form including those selected from the group consisting of an ointment, an aerosol, a gel, and a lotion.

The microparticles are linked to proteinaceous material. When used in vivo, the microparticles are attached to a body tissue. Particularly important body tissues as sites of attachment are the integument (including specifically skin, nails, hair, mucous membranes and the surface of the eye), internal organs, internal tissue and wound beds. In in vitro applications, the tissue may be a body tissue, a tissue or cell isolate, isolated proteins, synthetic proteins, cell cultures and the like for use, for example, in assay systems according to the invention. In preferred embodiments, the body tissue is a skin, nail or hair surface. In any of the embodiments described herein relating to the treatment of skin or a skin surface, it is to be understood that treatment of hair and nails is also intended, and can be interchanged.

These and other aspects of the invention are described in further detail below.

DETAILED DESCRIPTION OF THE INVENTION

Figure 1:
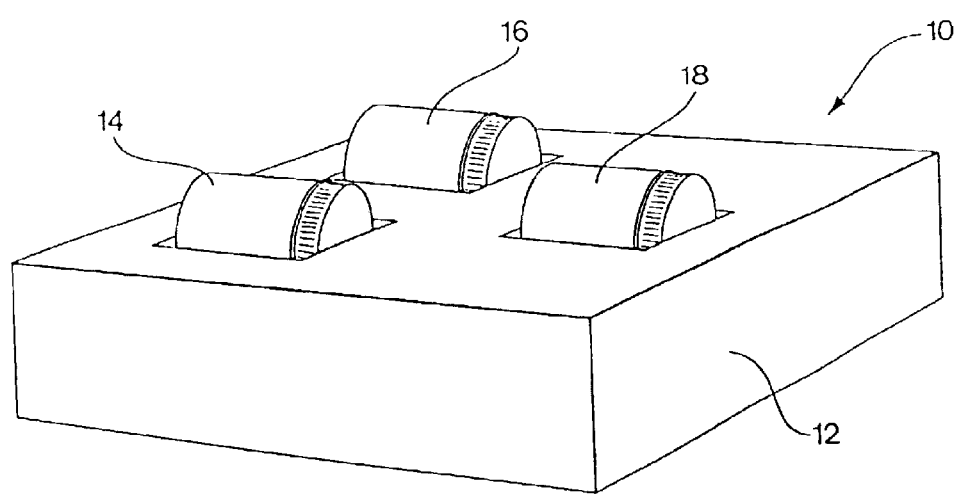
FIG. 1 depicts a kit according to the invention.

The invention relates in part to the discovery that microparticles with particular surface characteristics can be linked to a tissue and can thereby effect an extended period of agent delivery to the tissue.

The microparticles of the invention possess transglutaminase substrate reactive groups on their surface in an accessible form (i.e., surface available transglutaminase substrate reactive groups). Transglutaminase substrate reactive groups comprise carboxamide groups, such as those of glutamine residues, and aliphatic amine residues, such as those of lysine residues. The microparticles of the invention contain an active agent which when released from the microparticle provides prophylactic, therapeutic or cosmetic benefit to an external body surface with which it is in contact. The microparticles of the invention are preferably intended for use on an external body surface such as skin, hair or nails. As a result, the microparticles which remain attached to the external surface and which do not degrade substantially throughout the course of treatment (e.g., days or weeks) are most useful in the invention. Any microparticle that contains an active agent (as described herein) and that can hold (as a result of the covalent binding described herein) and release the active agent onto an external surface (e.g., a skin surface) for a period of time sufficient for the active agent to achieve its prophylactic, therapeutic or cosmetic purpose is useful in the invention. Microparticles commonly effect delivery of agents by way of diffusion, or by degradation or erosion. Examples of diffusional systems in which the active agent permeates at a controlled rate from a polymer are described in U.S. Pat. Nos. 3,854,480, 5,133,974 and 5,407,686. Examples of erosional systems in which the active agent is contained within a matrix which in turn erodes with time are described in U.S. Pat. Nos. 4,452,775, 4,675,189 and 5,736,152.

The invention provides microparticles which are either biodegradable or non-biodegradable. The term "biodegradable" as used herein refers to the ability of a substance (in this case, a microparticle) to degrade in vivo, (i.e., upon contact with external surfaces such as the skin). Commonly, biodegradable microparticles are made from polymers having bonds which are easily hydrolyzed once in contact with a physiological environment.

According to the present invention, covalent linkage of the microparticle to the skin, hair or nails is desired. It is the covalent linkage which keeps the microparticles on the skin for the desired time, preferably in a layer, to achieve uniform and extended release of the active agent as desired. If the microparticles degrade too quickly, or degrade when contacted with a detergent such as soap, then the uniform distribution and extended release will be undermined. If degradation is slow or if degradation can occur independent of covalent attachment (such as degradation within a shell), then degradation can be acceptable. Thus, biodegradable microparticles are embraced by some aspects of the invention. Preferably, the biodegradable microparticles degrade substantially only after the period of time corresponding to the treatment (e.g., days or weeks) in order to ensure sufficient delivery of the active agent to the skin surface.

Microparticles that are differentially biodegradable are also useful in the invention. A "differentially biodegradable" microparticle is one which does not degrade uniformly throughout its volume. It may instead degrade initially in an internal or core region, as an example. Internally degradable microparticles may be formed by coating biodegradable cores with non-biodegradable porous films or shells. The microparticle may alternatively degrade from the outer surface, however, it would still be necessary that a sufficient amount of reactive groups remain covalently attached at the surface and extending within the microparticle even throughout the portion of the degradation process during which covalent attachment of the microparticle is desired. This can be achieved, for example, by a microparticle which is covalently crosslinked internally. In important embodiments, the microparticles are substantially non-biodegradable at their point of attachment to the skin surface over the period of time during which covalent attachment is desired.

Another type of microparticle which is useful to the invention is one which is non-biodegradable. A non-biodegradable microparticle is one which does not degrade upon exposure to a physiological environment or temperature. As mentioned above, such non-biodegradable particles release active agent by diffusion. It is preferred that a subset of microparticles having carboxamide or aliphatic amine reactive groups be non-biodegradable. In important embodiments, the microparticles are substantially non-biodegradable during the treatment period, which may last for several days to several weeks or completely non-biodegradable. In this instance, the microparticles will simply be sloughed off along with the dead skin cells to which they are attached. As is well known to those of ordinary skill in the art, the outermost portion of the skin (i.e., the cornified layer), to which the microparticles will be attached in some instances, is not living and is sloughed off and replaced completely every 10 to 14 days.

The microparticles of the invention may be synthesized using naturally occurring or non-naturally occurring polymers. Non-naturally occurring polymers are referred to herein as synthetic polymers. Naturally occurring polymers include nucleic acids, peptides, polypeptides, carbohydrates, alginate, polysaccharides (e.g., dextran, cellulose and glycogen), lipopolysaccharides, chitosan, chitin, peptidoglycans, starch, glycosaminoglycans, collagen, rubber (cis-1,4-polyisoprene), guayule (Parthenium argentatum), collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof.

The microparticles may further comprise one or more synthetic polymers or co-polymers. As used herein, the term "synthetic" refers to a substance which is not naturally occurring. Exemplary synthetic polymers include, but are not limited to, polyamides, polycarbonates, polyalkylenes, polysulfones, poly(2-sulfobutyl-vinyl alcohol)-graft-poly(D,L-lactic-co-glycolic acid), poly-hydroxyalkanoates, polyalkylene glycols, polyalkylene oxides, polyalkylene terepthalates, polydimethylsiloxane polyvinyl alcohols, polyvinyl ethers, polyvinyl esters, polyvinyl halides, silicones, polyglycolic acid (PGA), polylactic acid (PLA), copolymers of lactic and glycolic acids (PLGA), polyanhydrides, polyorthoesters, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Still other microparticles may be comprised of chimeric polymers of synthetic and naturally occurring residues. "Chimeric polymers" as used herein, refer to polymers of different residues or units. For example, a chimeric polymer may contain amino acid and non-amino acid residues, or it may contain natural and synthetic residues. As used herein, a residue in a polymer refers to (and may be used interchangeably with) a unit of a polymer. Examples of a polymer residue (i.e., a polymer unit) include an amino acid in a peptide and a nucleotide in a nucleic acid. Non-amino acid residues such as saccharides, fatty acids, sterols, isoprenoids, purines, pyrimidines, derivatives or structural analogs of the above, or combinations thereof and the like may be used. Non-naturally occurring non-amino acid substitutes include but are not limited to 2-azetidinecarboxylic acid, pipecolic acid, S-ethylisothiourea, 2-$NH_2$-thiazoline and 2-$NH_2$-thiazole.

The natural, synthetic and chimeric polymers may themselves be biodegradable or non-biodegradable, as intended herein. Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as those listed herein. In general, these materials degrade either by enzymatic hydrolysis or exposure to water in vivo, by surface or bulk erosion. The polymers may optionally be in the form of a hydrogel that can absorb up to about 90% of its weight in water and further, optionally may be crosslinked with multivalent ions or other polymers.

Examples of non-biodegradable synthetic polymers include latex, polystyrene, polystyrene derivatives, poly-N-ethyl-4-vinylpyridinium bromide, silicone, polypropylene, ethylene vinyl acetate, poly(meth)acrylic acid, polymethylacrylate, polyamides, copolymers and mixtures thereof. U.S. Pat. No. 5,861,149 discloses methods for making non-biodegradable microparticles which can be used in the present invention. Polystyrene particles useful in the invention are commercially available from a variety of manufacturers including Polysciences, Inc. (Warrington, Pa.), Seradyn (Indianapolis, Ind.) and Dynal.

The microparticles may also be formed from or may include non-polymer moieties such as lipids including sterols such as cholesterol, cholesterol esters and fatty acids or neutral fats such as mono- di- and tri-glycerides.

The microparticles may be made from organic and/or inorganic substances. The majority of polymers listed above are organic. Examples of inorganic substances include but are not limited to polyphosphate, zirconia-silica (ZS), $Si(OC_2H_5)_4$, $Al(NO_3)_3 \times 9H_2O$, $AgNO_3$, $HNO_3$, poly (phenylphosphinoborane) (an inorganic analogue of polystyrene) and PRIMM.

The polymer and non-polymers which make up the microparticles may be crosslinked, but need not be. Crosslinking agents include chemicals such as glutaraldehyde, dithiobis (succinimidyl) propionate, carbodiimide, and N-succinimidyl-3-(2-pyridyldithio) propionate (SPDP), 1,4-Bis(acryloyl)piperazine, N-Hydroxysulfosuccinimide, as well as electromagnetic radiation such as UV radiation. A wide variety of crosslinking agents suitable to the various chemistries of the microparticles described herein are commercially available from manufacturers such as Pierce Chemical Co. (Rockford, Ill.) and Sigma Aldrich (St. Louis).

In some embodiments, the microparticles may be predominantly composed of one or more polymers. A blend of natural and synthetic polymers may be used in microparticle synthesis. The microparticles may have an external coating composed of the same or a different polymer or non-polymer substance. As an example, the microparticle may be composed internally of polystyrene and an active agent and may have an exterior coating (preferably covalently attached) of a substance rich in transglutaminase substrate reactive groups (as discussed below). In other related embodiments, more than one polymeric or non-polymeric substance, or a combination thereof, may be commingled prior to microparticle formation, resulting in their combined presence both internally and on the external surface of the microparticle.

As used herein, the term "microparticle" embraces particles, spheres and capsules of both nanometer and micrometer sizes (i.e., microparticles, microspheres, nanoparticles, nanospheres, microcapsules and nanocapsules). The microparticles may adopt a variety of shapes including regular shapes such as spheres and ellipses as well as non-regular shapes. Additionally, the surface may be, but need not be, smooth. The microparticles may be hollow with the agent stored in the core of the shell, in which case, they may be referred to as microcapsules or nanocapsules. Alternatively, they may be porous with the agent dispersed throughout the solid polymeric or non-polymeric matrix, in which case they may be referred to as microspheres or nanospheres. A porous microparticle is one having internal, potentially interconnected channels (or pores) which are preferably open to the external surface of the particle. Methods for synthesizing hollow and porous microparticles are well known in the art. Porous microparticles are generally made by the inclusion of a porogen during microparticle synthesis followed by its removal (e.g., through dissolution in an appropriate solvent) and subsequent replacement with a solution containing the active agent. As provided herein, the porous microparticles may additionally have a coat comprising transglutaminase substrate reactive groups (as described below), while being internally void of these groups.

It is recommended that the microparticle be less than five microns in size (i.e., any single dimension of the microparticle is less than 5 microns). The microparticle should be small enough so as to feel smooth when applied to the external body surface. In some embodiments, it is preferred that the particles be large enough to preclude their penetration into the external surface. It has previously been reported that microparticles less than 100 microns are capable of penetrating the skin surface. In certain embodiments, the microparticles or their surface available transglutaminase reactive groups are capable of penetrating the external surface, preferably up to but not including the layer of living cells. Thus, in some embodiments, the average size of the microparticle is less than 1 micron but greater than 100 nm, and in others, it is 100 nanometers to 500 nanometers. In still other embodiments, the average size of the microparticles is less than 100 nm in size, 20 nm to 90 nm in size, or 20 nm to 35 nm in size. These smaller particle sizes may be preferred when particle penetration of the skin is desired. In most instances, it may be undesirable for the microparticles to penetrate the living layer, and it is therefore intended that the microparticle remain in the cornified layer. It is believed that microparticles less than 1 nm, as well as others that are less than 5 nm could penetrate to the living layer, and thus should be avoided in most instances. However, it may be desirable for the particles to enter the cornified layer and thereby release their active agent which may diffuse into and thereby enter the living layer. Still, microparticles of an average size of 1 nm to 20 nm and in particular 5 nm to 10 nm may be desirable in some aspects of the invention. It is well within the realm of the ordinary artisan to determine the size of particles which are best suited to the various embodiments recited herein.

It also should be noted that size may be uniform as in all the particles being of a certain size or range or size may be mixed. Where it is desired to prevent the microparticles from penetrating the outer most surface of the epidermis, then all the microparticles should be at least a certain size (e.g., at least 100 nm). If it is desired that all microparticles penetrate the outer most surface of the epidermis, then all should be no larger than a certain size (e.g., no larger than 100 nm). It also may be desired to have a variety of sizes whereby the microparticles will penetrate to different extents depending on size, thereby forming a three dimensional "layer". Size will depend upon factors such as the agent to be delivered, the condition being treated, the desired length of treatment, and other such factors well known to those of ordinary skill in the art. Appropriate size can be determined by no more than routine experimentation, trying different sizes to select the one or ones that are ideal for a particular purpose.

The microparticles are linked to proteinaceous material. When used in vivo, the microparticles are attached to a body tissue. Particularly important body tissues as sites of attachment are the integument (including specifically skin, nails, hair, mucous membranes and the surface of the eye), internal organs, internal tissue and wound beds. In in vitro applications, the tissue may be a body tissue, a tissue or cell isolate, isolated proteins, synthetic proteins, cell cultures and the like for use, for example, in assay systems according to the invention. In preferred embodiments, the body tissue is a skin, nail or hair surface.

Due to the preferred use of these particles on skin, hair and nails, it is important that some of these particles be resistant to the action of detergents, such as those regularly used on these surfaces (e.g., hand, face and body soap, and shampoo). Thus, in some embodiments, the microparticles are water insoluble and, preferably, detergent insoluble (i.e., neither the microparticle nor the bond between the microparticle and the external surface are adversely affected by exposure to detergents, such as hand, body and hair soap). Many of the organic polymers listed herein are water insoluble. It is well within the realm of the ordinary artisan to determine which of these are preferred for making water insoluble particles. One way of making microparticles detergent insoluble is by cross-linking or by or by derivatizing the microparticles or their substituents with other properties which produce bonds other than those which covalent in order to render the microparticle insoluble. If cross-linking is used, it is recommended that the transglutaminase substrate reactive groups are protected to prevent them from participating in the cross-linking, that a crosslinking agent be used which does not involve the transglutaminase substrate reactive groups or that the transglutaminase substrates be attached to the microparticle after such cross-linking. In another embodiment, the microparticles can be made more resilient to detergent treatment by the incorporation of fluorinated steroids as taught in U.S. Pat. No. 4,927,687.

To be useful, the microparticles must possess transglutaminase substrate reactive groups. Transglutaminase substrate reactive groups comprise carboxamide groups, preferably γ-carboxamides, and amine groups, preferably, aliphatic amine groups. Carboxamide groups are at least present in glutamine residues and aliphatic amines are at least present in lysine residues. The reactive groups may be provided by any moiety which contains them, including, but not limited to, peptides, polypeptides and proteins.

It has been previously shown that transglutaminases are capable of crosslinking substrates other than lysine to glutamine residues. For example, compounds containing aliphatic amines, such as diamines and polyamines (including spermine and spermidine), have been shown to act as transglutaminase substrates. Thus, one of ordinary skill in the art will be able to synthesize and test the transglutaminase substrates-described herein, including polymers of reactive amines and carboxamides with no more than routine experimentation.

As suggested in the foregoing discussion, it is important that these reactive groups be accessible to the body tissue (e.g., the skin) to which the microparticles are to be bound. The reactive groups must be sufficiently exposed, and the backbone to which they are attached preferably sufficiently flexible, to react with and form a covalent bond with reactive groups on the contacted surface. Reactive groups which are present on the surface of the microparticles are likely to be accessible, and thus such "surface available" reactive groups are generally preferred.

Surface available reactive groups may be "free" or "fixed." Free surface available reactive groups include those which are present on a free, unconstrained end of a polymeric or non-polymeric substance, present at the surface of the microparticle. The free, unconstrained end of the polymeric or non-polymeric substance may be any length, provided the reactive groups contained therein are capable of reacting with the skin. Free reactive groups also embrace those which are non-complexed. A non-complexed reactive group is one which is not in physical association with another moiety to the extent that it is precluded from contacting and being covalently attached to a reactive group on, for example, the skin. Fixed reactive groups may also be useful in the invention, provided they are sufficiently flexible to bind to skin surface reactive groups. Thus, a reactive group may be present in a loop of a polymer the ends of which are both bound to the surface of the microparticle. As long as the loop is long enough and flexible enough to allow the reactive groups to contact and react with the skin surface, this type of "fixed reactive group" will be useful.

The surface available transglutaminase substrate reactive groups must also be present in an amount sufficient to attach covalently the microparticles to the skin in the presence of transglutaminase. Transglutaminase may be supplied exogenously (i.e., exogenous transglutaminase) or it may be endogenous to the tissue (i.e., endogenous transglutaminase). The source of transglutaminase plays an important role in the amount of surface available transglutaminase substrate reactive groups that are sufficient to link the microparticle to an external surface (and in the size of the microparticle, as discussed above). Exogenously supplied transglutaminase may be supplied in quantities exceeding those which are available endogenously. As a result, in embodiments relying on the action of endogenous transglutaminase for linking of microparticles to, for example, the skin, the amount of surface available groups sufficient for linking will generally be higher than that amount sufficient for linking using exogenous transglutaminase.

Polymeric and non-polymeric substances from which the microparticles are synthesized may inherently possess the necessary reactive groups, or they may be derivatized either prior to or following microparticle formation to possess such groups. Alternatively, the microparticles may be formed of substances lacking transglutaminase substrate reactive groups (e.g., polystyrene) and then coated with a substance which contains these groups, or such substrates may be added to the microparticle components during synthesis whereby they are present in and on the surface of the microparticle but not covalently linked to it. In a variation of this, the transglutaminase substrate reactive groups may also be linked to the surface of the microparticle after microparticle formation. As an example, the surface may be prepared or treated to contain carboxamide residues, after which it is exposed to an excess of an aliphatic amine-containing polymer (e.g., present in a lysine-rich polymer) in the presence of limited quantities of transglutaminase. It is likely that even after binding of the carboxamide residues to the aliphatic amines in a 1:1 ratio, an excess of aliphatic amine reactive groups will still be present on and pendant from the surface of the microparticle. A similar approach in which the surface of the microparticle is initially treated to contain aliphatic amines is also envisioned. Polymers rich in such reactive groups also can be covalently attached at a terminal end of a substrate at the surface of the microparticle, or simply be covalently attached to the surface of the microparticle using homo and heterobifunctional cross-linkers. It further is envisioned that such polymers can be tethered to the surface of a microparticle by hydrophobic bonding. The manufacture of such microparticles is well within the realm of the ordinary artisan.

The methods for manufacturing a variety of microparticles according to the prior art are well documented. The present invention differs from those of the prior art, in part, in that the polymers or non-polymers of the microparticle themselves contain or are derivatized to contain carboxamide groups such as those present in glutamines and/or aliphatic amines such as those present in lysines, but at the surface, available for covalent bonding to the skin. In one embodiment, the polymers of glutamine, lysine or glutamine and lysine are included within the mixture of polymers forming the matrix, resulting in the presence of these reactive groups throughout and at the surface of the microparticles. Examples of microspheres and nanospheres and their method of manufacture may be found in U.S. Pat. No. 5,075,019, PCT WO95/24929, PCT WO94/23738 and PCT WO97/03657, the disclosures of which are incorporated herein by reference.

Preferred polymers are polymers bearing multiple reactive carboxamides and/or aliphatic amines that are substrates of transglutaminase. Carboxamides that are substrates of transglutaminase are well known and include glutamines. Aliphatic amines that are substrates of transglutaminase also are well known and are exemplified in, for example, U.S. Pat. No. 5,490,980, the disclosure of which is incorporated herein by reference. Unlike the '980 patent, however, which depicts single aliphatic amine moieties and a plural thereof as independent substituents in certain circumstances, the present invention involves in one aspect using a plurality of aliphatic amines spaced apart at discrete intervals, preferably along the length of a branched or unbranched polymer. It has been discovered, surprisingly, that the spacing of the reactive moieties can be important to achieving the results of the present invention.

A further embodiment of the present invention involves microparticles comprising polymers having multiple units, which each bear a transglutaminase substrate reactive group in the form of an aliphatic amine or a carboxamide. The polymer can be a homopolymer or a heteropolymer. As used herein in connection with polymers having transglutaminase substrates, a polyaliphatic amine is a molecule with at least three aliphatic amines spaced apart from one another at discrete intervals along the backbone of the polymer, separated by one or more backbone atoms. This is most easily envisioned, for example, with polymers rich in lysine, whereby discrete units of the polymer carry the aliphatic amine, each being separately a substrate for transglutaminase. The polymer may comprise or in some instances consist solely of contiguous lysines, preferably at least 3, at least 4 and at least 5 such contiguous lysines. Polymers of contiguous units, each carrying an aliphatic amine, are preferred. The same is the case for carboxamides and glutamine.

Another category of preferred polymer is those rich in a carboxamide moiety or an aliphatic amine moiety, such as glutamine, lysine or both glutamine and lysine. A polymer rich in glutamine or lysine is a molecule wherein at least 20% of the units of the polymer carry a carboxamide, an aliphatic amine, or both, such as glutamine, lysine or glutamine and lysine, or wherein the molecule includes at least 3, preferably 4 and most preferably 5 separate and discretely spaced by a regular distance carboxamides or aliphatic amines, such as occurs with contiguous, linked glutamines or lysines. In other embodiments, the polymer includes at least 10, at least 15 or at least 20 separate and discretely spaced carboxamides or aliphatic amines. It should be understood, however, that a chain of as few as two glutamines or lysines can be attached to or tethered to an microparticle to render the microparticle a "substrate" of transglutaminase. The polymers may also contain at least 30%, at least 40%, at least 50% or more of lysine or glutamine or both lysine and glutamine, depending upon the embodiment.

In constructing microparticles, it may be desirable to vary not only the number of surface available transglutaminase substrate glutamines and/or lysines, but it also may be desirable to tether the transglutaminase substrate glutamines and/or lysines to the microparticle via a spacer. This can remove, for example, any problems that might arise from steric hindrance, wherein access by transglutaminase to the reactive group directly on the surface is hindered. These spacers can be any of a variety of molecules, preferably nonactive, such as straight or even branched carbon chains of $C_1$–$C_{30}$, saturated or unsaturated, phospholipids, amino acids, and in particular glycine, and the like, naturally occurring or synthetic. Additional spacers include alkyl and alkenyl carbonates, carbamates, and carbamides. These are all related and may add polar functionality to the spacers such as the $C_1$–$C_{30}$ previously mentioned.

The polymers may also have termini (either amino or carboxy) that are predominantly rich in glutamine or lysine. Preferably, the termini are located on the surface of the microparticle. The lysine or glutamine rich stretch of the polymer may also be located on a "loop" of the polymer which is present at the surface. Naturally occurring polymers rich in glutamine residues include prolamines such as gliadin, kafirin, zein and hordein. U.S. Pat. Nos. 5,679,377 and 5,271,961 disclose biodegradable microparticles which may include prolamines and which are treated with transglutaminase in order to increase their stability. As a result of this pre-treatment with transglutaminase, it is expected that glutamine carboxamide reactive groups of the reported microparticles will no longer be available for further covalent conjugation. The microparticles useful to the present invention differ from these prior art microparticles in that they at least require a sufficient amount of surface available transglutaminase substrate reactive groups in order to bind to the body tissue.

The conjugations or modifications described herein employ routine chemistry, which chemistry does not form a part of the invention and which chemistry is well known to those skilled in the art of chemistry. The use of protecting groups and known linkers such as mono- and heterobifunctional linkers are well documented in the literature and will not be repeated here.

Attachment according to the invention thus need not be directed attachment. The components of the compositions of the invention may be provided with functionalized groups to facilitate their attachment and/or linker groups may be interposed between the components of these compositions to facilitate their attachment. In addition, the components of the compositions of the present invention may be synthesized in a single process, whereby the components could be regarded as one and the same entity. For example, a protein agent may be synthesized recombinantly to include a polyglutamine at one end for linking to the tissue via transglutaminase.

As used herein, "linking" means two entities stably bound to one another by any physiochemical means. It is important that the nature of the attachment be such that it does not impair substantially the effectiveness of either entity. Keeping these parameters in mind, any linkage known to those of ordinary skill in the art may be employed including covalent or noncovalent. Covalent linkage is preferred, particularly as relates to the linking of microparticles of the invention to a body tissue, such as, the skin. Such means and methods of attachment are well known to those of ordinary skill in the art.

Specific examples of covalent bonds include those wherein bifunctional crosslinker molecules are used. The crosslinker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available crosslinkers are reactive with one or more of the following groups: primary amines, secondary amines, sulphydryls, carboxyls, carbonyls and carbohydrates. Examples of amine-specific cross-linkers are bis(sulfosuccinimidyl) suberate, bis[2-(succinimidooxycarbonyloxy)ethyl]sulfone, disuccinimidyl suberate, disuccinimidyl tartarate, dimethyl adipimate.2 HCl, dimethyl pimelimidate.2 HCl, dimethyl suberimidate.2 HCl, and ethylene glycolbis-[succinimidyl-[succinate]]. Cross-linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido)

butyl]-3'-[2'-pyridyldithio]propionamide. Crosslinkers preferentially reactive with carbohydrates include azidobenzoyl hydrazine. Crosslinkers preferentially reactive with carboxyl groups include 4-[p-azidosalicylamido] butylamine. Heterobifunctional cross-linkers that react with amines and sulfhydryls include N-succinimidyl-3-[2-pyridyldithio]propionate, succinimidyl[4-iodoacetyl] aminobenzoate, succinimidyl 4-[N-maleimidomethyl] cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[[3-dimethylaminopropyl]-carbodiimide hydrochloride. Heterobifunctional cross-linkers that react with carbohydrates and sulfhydryls include 4-[N-maleimidomethyl]-cyclohexane-1-carboxylhydrazide.2 HCl, 4-(4-N-maleimidophenyl)-butyric acid hydrazide.2 HCl, and 3-[2-pyridyldithio] propionyl hydrazide. The cross-linkers are bis-[β-4-azidosalicylamido)ethyl]disulfide and glutaraldehyde. Amine or thiol groups may be added at any nucleotide of a synthetic nucleic acid so as to provide a point of attachment for a bifunctional crosslinker molecule. The nucleic acid may be synthesized incorporating conjugation-competent reagents such as Uni-Link AminoModifier, 3'-DMT-C6-Amine-ON CPG, AminoModifier II, N-TFA-C6-AminoModifier, C6-ThiolModifier, C6-Disulfide Phosphoramidite and C6-Disulfide CPG (Clontech, Palo Alto, Calif.).

A number of different techniques exist for making microparticles including phase separation, solvent evaporation, emulsification and spray drying. The following examples are intended to provide guidance in the synthesis of some microparticles of the invention.

Encapsulated microspheres made from poly(lactide-co-glycolide) and poly(ε-CBZ-L-lysine) and subsequently treated so as to expose surface reactive amino groups have been reported previously. (Zheng and Hornsby, 1999, Biotechnol. Prog. 15:763–767) Once the microspheres are formed using double-emulsification/solvent evaporation (Alonso; et al., 1993, Pharmacol. Res. 10:945–953), the carbobenzoxy (i.e., CBZ) protective groups are removed using either acid hydrolysis or lithium/liquid ammonia reduction, thereby exposing reactive amine groups. Lithium/liquid ammonia reduction is recommended if microspheres are desired, given its less harsh effect of the external surface of the microparticle. In addition, the lithium treatment was reported to be more effective in producing surface reactive amino groups than was the acid hydrolysis procedure. If a solid surface particle (i.e., a microsphere) is desired, the lithium treatment may be preferred. In this latter method, the active agent may be added during the formation of the microparticles since the lithium treatment reportedly does not create pores in the surface of the particles and thus will not adversely affect the agent. If, on the other hand, a surface porous particle is desired, then the acid hydrolysis method may be preferred, provided the agent is either resistant to the acid treatment or is loaded into the particles following acid treatment.

A similar strategy may be used to produce non-biodegradable microparticles, by substituting poly(lactide-co-glycolide) with a non-biodegradable polymer such as those disclosed herein. In another variation of this method, a copolymer of lysine and a synthetic polymer such as, for example, poly(lactic acid-co-lysine) may be used alone to form the microparticles followed by mild acid hydrolysis or lithium treatment. Such lysine containing copolymers have been manufactured previously. (Barrera, et al., 1993, J. Am. Chem. Soc. 115:11010–11011) In yet a further variation, it may be possible to form particles from a biodegradable or a non-biodegradable polymer mixed with a CBZ-lysine rich polymer which is not poly-lysine or, alternatively, with short peptide or peptidomimetic backbone compounds which contain CBZ-protected aliphatic amines.

In another modification, microparticles may be made using the technique of Zheng and Hornsby but excluding poly-lysine. After being formed, the microparticles may be coated with a solution of poly(ε-CBZ-L-lysine). Commercially available microparticles such as those made from polyacrylamide, polyacrylate, polystyrene, or latex (Bio-Rad Laboratories (Richmond, Calif.), LKB Produkter (Stockholm, Sweden)) or those made from natural polymers such as agarose, crosslinked agarose, globulin, and liposomes (Bio-Rad Laboratories (Richmond, Calif.), Pharmacia (Piscataway, N.J.), IBF (France)) can also be coated with CBZ-protected as well as non-protected lysine containing polymer solutions following agent loading. Microcapsule coating methods are known in the art.

To determine whether a microparticle generated according to the teachings herein is a substrate of transglutaminase, a simple screening method is employed. The screening method involves selecting a microparticle that is a putative substrate for transglutaminase. The microparticle is applied, in an isolated form, to a proteinaceous material such as a body tissue, a body tissue isolate, or more preferably, a polymer rich in glutamine, a polymer rich in lysine or a polymer rich in glutamine and lysine. Transglutaminase is then applied to the proteinaceous material in an amount sufficient and under appropriate conditions to cross-link the microparticle to the proteinaceous material if the microparticle is a substrate of transglutaminase. Then it is determined whether the microparticle covalently binds to the proteinaceous material. The microparticle may be loaded with a labeling agent such as a fluorescent dye or a fragrance. As applied to the screening assay, it is recommended that the labeling agent is covalently fixed to the microparticle such that no label escapes from the microparticle. This will ensure that any label detected on the external surface is indicative of a microparticle that is bound to the surface rather than a label which has exited a microparticle which itself was not capable of binding to the surface. In a further modification of this assay, once the microparticle is allowed to bind to the surface, the surface may be additionally washed with water and/or a detergent and then again tested for the presence of the microparticle. The amounts of materials and conditions employed for these assays are derivable from the examples below and, in general, can be derived by those of ordinary skill in the art without undue experimentation from, for example, the publication by Kahlem, et al., *Proc. Natl. Acad. Sci., USA*, Vol. 93, pp. 14580–14585, December, 1996.

Prior to contact with the body tissue, the microparticle is loaded with an active agent, either physically entrapped therein, covalently bonded thereto or otherwise physiochemically attached to the microparticle. The active agent may be incorporated (i.e., "loaded") into the microparticle either at the time of, or after, microparticle formation, depending upon whether the microparticle formation process would be deleterious to the active agent. By active agent it is meant that the agent, once coupled to a biological tissue (such as skin) in vivo or in vitro, either directly or indirectly via a microparticle, has, maintains or can be released to have a desired activity such as a desired physiological, prophylactic, therapeutic or cosmetic activity.

Examples of active agents are pharmaceutical agents, sunscreen agents, insecticides, bactericides, fungicides, etc. In certain embodiments, the active agent is not a labeling agent such as a diagnostic agent. In other embodiments, the agent is not a cosmetic agent.

In some aspects of the invention, particularly where the microparticle comprises poly-lysine as the source of transglutaminase substrate reactive groups, the active agent is a non-nucleic acid active agent. A non-nucleic acid active agent, as used herein, refers to an active agent which is not a nucleic acid. In other embodiments, the active agent is a non-protein active agent. A non-protein active agent is an active agent which is not a protein (i.e., it is not composed exclusively of peptide linkages of amino acid residues or units).

In general, the active agents are chemical agents and include pharmaceutical agents, enzymes, cosmetics, bulking agents, hair conditioners and hair fixatives, anti-foaming agents, antistatic agents, moisturizing agents, including humectants, depilatories (i.e., hair removal agents), vitamins, film forming agents such as those used in hair fixatives or wound healing, anti-nerve gas or anti-neurotoxin agents, sunscreen agents, ligands of ligand-receptor pairs, receptors of ligand-receptor pairs, components of high affinity noncovalent bonding pairs, insecticides and repellants including louse repellents, bactericides, fungicides, tissue sealants, labels, structural proteins, chelating agents, microparticles and the like. Examples are listed below.

In certain embodiments the agent is a noncorneocyte, nonlabeling active agent. Specifically excluded in these embodiments are corneocyte proteins. Corneocyte proteins have been shown in the prior art to be among the natural substrates of transglutaminase. In certain embodiments the agent also is a non-extracellular matrix protein agent. A non-extracellular matrix protein agent is one that is not an extracellular matrix protein. Fibronectin, an extracellular matrix protein, also has been shown in the prior art to be a substrate of transglutaminase. A nonlabeling active agent is one that is not simply a passive label with no function, when applied to a body tissue, other than being a label. Thus, specifically excluded in some embodiments are labeled corneocyte proteins, labeled fibronectin, labeled extracellular matrix proteins, putrescine, dansylcadaverine, 5-(biotinamido)-pentylamine, fluoresceincadaverine and the like. Such compounds have been used in the prior art to detect substrates of transglutaminase in or on cells or cell extracts.

Typically the agents used according to the invention are not themselves, in their native form, substrates for transglutaminase. If desired, however, such agents can be modified according to the invention to render the agent a substrate of transglutaminase. This may be accomplished for example by adding a carboxamide side group(s) to an appropriate moiety of the agent (i.e. a "modified" agent) or by covalently coupling glutamine, lysine or both glutamine and lysine to the agent to form a conjugate that is a substrate of transglutaminase. The most preferred method is to couple polyglutamine, polylysine, a mixed polymer of glutamine and lysine, involucrin (a natural substrate of transglutaminase) or a fragment of involucrin to the agent to form an appropriate conjugate.

The active agent may be linked to the natural, synthetic or chimeric polymer or non-polymer. Such linkage may be covalent in nature. Preferably, any linkage between the active agent and another component of the microparticle is characterized by a bond that cleaves under normal physiological conditions or that can be caused to cleave specifically upon application of a stimulus such as light, whereby the agent can be released. Readily cleavable bonds include readily hydrolyzable bonds, for example, ester bonds, amide bonds and Schiff's base-type bonds. Bonds which are cleavable by light are well known. In certain instances, the agent may be inactive in its conjugated form and activated only when released. In other instances, the agent would be released to exert an activity remote from the point of attachment of the microparticle to the body tissue.

Noncovalent methods of conjugation may also be used. Noncovalent conjugation includes hydrophobic interactions, ionic interactions, high affinity interactions such as biotin-avidin and biotin-streptavidin complexation and other affinity interactions.

In some embodiments, it is preferred that the active agent is free and not linked to another component of the microparticle. In these latter embodiments, the release of the active agent from the microparticle is dependent upon the flow of (physiological) fluids into the porous network of the microparticle, the dissolution of the active agent in such fluids and the exit of fluid and agent from the microparticle. Preferably, the agent would be released in a sustained fashion.

Active agents in an isolated form may also be used according to the invention. "Isolated" as used herein will depend upon the agent employed. In general, isolated means that the material is essentially free of other substances to an extent practical and appropriate for the intended use of the material. In the case of pharmaceuticals and cosmetics, the materials are likely to be substantially pure. In the case of proteins, the proteins are sufficiently pure and sufficiently free from other biological constituents of the host cells from which the proteins are derived so as to be useful in the methods according to the invention. Typically, such active agents will be at least 95% or more pure.

Agents are sometimes described as native agents herein. A native agent is one as it occurs in nature (isolated or synthesized to duplicate a naturally occurring molecule), without modification or conjugation as described herein.

As mentioned above, the body tissue, to which the microparticles are to be applied, may be, but need not be, pretreated to facilitate the reaction with transglutaminase. Such treatments include washings, abrasive treatments including physical agents such as pumice, silica and oatmeal, enzymes such as papain, bromelins and the like and chemical agents such as alpha hydroxy acids and glycolic acids. The main object is to treat the body tissue so as to expose or create reactive glutamines and/or lysines. Likewise, as mentioned above, the body tissue may be pretreated by putting down a layer of reactive groups, such as by applying to the body tissue polymers rich in lysine, glutamine or both lysine and glutamine. These materials may be attached to the body tissue by any conventional means, but, according to the invention, also may be attached using transglutaminase.

It should be noted that glutamine, lysine, and polymers of glutamine and lysine are described above. As used herein, such terms embrace nonpeptidic multimers of glutamine and lysine whereby amino acid analogs are used to replace these amino acids in the polyglutamine or polylysine substrates. Some well known classes of peptide mimetics and pseudopeptides are: azabicycloalkane amino acids; thiazabicycloalkane amino acids; oxazabicycloalkane amino acids; diazabicycloalkane amino acids. D-amino acids are an important embodiment.

The transglutaminase may be exogenously added transglutaminase or may be endogenous transglutaminase present at the tissue.

The invention thus may be used, inter alia, to localize drugs to a tissue such as a wound bed or for localized delivery to a tissue, to hold a drug, insect repellant, bactericide fungicide, growth factors, cytokine, and the like at a particular location to prevent the drug from being flushed away to other body sites where it is not needed, to apply bulking agents and other cosmetic agents to the integuments, such as the skin, hair and nails, to hold sunscreen agents at the surface of the skin for longer periods of time, to hold anti-nerve gas enzymes at the surface of the skin whereby nerve gas can be deactivated, to hold or link chemical agents to the skin which can in turn act as binding sites for other agent or alternatively, as reactive sites for catalytic buildup of multiple alternating layers, to link hydrophobic compounds to the skin, thereby making the skin hydrophobic, to link conditioners to the hair, thereby giving hair the appearance of greater bulk and to provide agents to organs or tissues which are to be transplanted.

The active agent may be a sunscreen agent. Examples of sunscreen agents include: p-aminobenzoate analogs such as 2-ethylhexyl-4-dimethylaminobenzoate (Padimate O); p-methoxy-2-ethyl-hexyl-cinnamate (Parsol 1789); oxybenzone (benzophenone-3); ethylhexylsalicylate; diphenylacrylate polyisobutylene; alkyl-β,β-diphenylacrylate and α-cyano-β,β-diphenylacrylate; 1-(4-aminophenyl)-2-morpholinylethanone; (1-(4-methoxylphenyl)-3-(4-tert-butyl-phenyl)-propan-1-3-dione; methyl anthranilate; octocrylene; Tretinoin "-hydroxyacid; diphenylacrylate polyisobutylene; 1-(4-aminophenyl)-2-morpholinylethanone; diphenylacrylate polyisobutylene; digalloyl trioleate; glyceryl p-aminobenzoate; 4-(omega-dialkylaminoalkoxy)phenylmethylene)-1,3,3-trimethyl-2-oxabicyclo(2.2.2)octan-6-ones;5-(arylmethylene)-1,3,3-trimethyl-2-oxabicyclo(2.2.2)octan-6-ones; melanin.

Further examples of sunscreen agents include: 3-benzylidene camphor; 4-methylbenzylidene camphor; allantoin PABA benzalphthalide; benzophenone; benzophenone-1; benzophenone-10; benzophenone-11; benzophenone-12; benzophenone-2; benzophenone-3; benzophenone-4; benzophenone-5; benzophenone-6; benzophenone-7; benzophenone-8; benzophenone-9; benzyl salicylate; benzylidene camphor sulfonic acid; bornelone; bumetrizole; butyl methoxydibenzoylmethane; camphor benzalkonium methosulfate; cinoxate; DEA-methoxycinnamate; diisopropyl methyl cinnamate; dimethyl PABA ethyl cetearyldimonium tosylate; drometrizole; ethyl cinnamate; ethyl dihydroxypropyl PABA; ethyl diisopropylcinnamate; ethyl methoxycinnamate; ethyl urocanate; etocrylene; glyceryl octanoate dimethoxycinnamate; glyceryl PABA; glycol salicylate; homosalate; isoamyl p-methoxycinnamate; isopropyl dibenzoylmethane; isopropyl methoxycinnamate; isopropylbenzyl salicylate; menthyl anthranilate; menthyl salicylate; n-ethyl-3-nitro PABA; octocrylene; octrizole; octyl dimethyl PABA; octyl methoxycinnamate; octyl salicylate; octyl triazone; PABA; PEG-25 PABA; phenylbenzimidazole sulfonic acid; polyacrylamidomethyl benzylidene camphor; potassium methoxycinnamate; potassium phenylbenzimidazole sulfonate; red petrolatum; sodium phenylbenzimidazole sulfonate; TEA-phenylbenzimidazole sulfonate; TEA-salicylate; terephthalylidene dicamphor sulfonic acid; tripaba panthenol; urocanic acid.

Further examples of compounds which are suitable sunscreen agents include: derivatives of para-amine benzoic acid (PABA); salicylates; cinnamates; benzophenones; camphors;4-aminobenzoic acid; N,N,N-trimethyl-4-(2-oxoborn-3-ylidenemethyl) anilinium methyl sulphate; homosalate (INN); oxybenzone (INN); 2-phenylbenzimidazole-5-sulphonic acid and its potassium, sodium and triethanolamine salts; 3,3'-(1,4-phenylenedimethylene) bis (7,7-dimethyl-2-oxobicyclo-[2.2.1] hept-1-ylmethanesulphonic acid) and its salts; 1-(4-tert-butylphenyl)-3-(4-methoxyphenyl) propane-1,3-dione; alpha-(2-oxoborn-3-ylidene) toluene-4-sulphonic acid and its salts; 2-cyano-3,3-diphenyl acrylic acid, 2-ethylhexyl ester (octocrylene); polymer of N-{(2 and 4)-[(2-oxoborn-3-ylidene)methyl]benzyl} acrylamide; octyl methoxycinnamate; ethoxylated ethyl-4-aminobenzoate (PEG-25 PABA); isopentyl-4-methoxycinnamate (isoamyl p-methoxycinnamate); 2,4,6-trianilino-(p-carbo-2-ethylhexyl-1'-oxy)-1,3,5-triazine (octyl triazone); phenol 2-(2h-benzotriazol-2-yl)-4-methyl-6-(2-methyl-3-(1,3,3,3-tetramethyl-1-(trimethylsilyl)oxy)-disiloxanyl)propyl) (drometrizole trisiloxane); 3-(4'-methylbenzylidene)-d-1 camphor (4-methylbenzylidene camphor); 3-benzylidene camphor (3-benzylidene camphor); 2-ethylhexyl salicyclate (octyl-salicylate); 2-ethylhexyl-4-dimethylaminobenzoate; 2-hydroxy-4-methoxybenzo-phenone-5-sulphonic acid and sodium salt (sulisobenzone and sulisobenzone sodium); 4-isopropylbenzyl salicylate; cinnamic derivatives, such as, for example, 2-ethylhexyl p-methoxycinnamate; salicylic derivatives, such as, for example, 2-ethylhexyl salicylate; camphor derivatives, such as, for example, (4-methylbenzylidene)camphor or benzene-1,4-di(3-methylidene-10-camphorsulfonic) acid; benzimidazole derivatives, such as 2-phenylbenzimidazole-5-sulfonic acid; benzophenone derivatives, such as 2-hydroxy-4-methoxybenzophenone; dibenzoylmethane derivatives, such as 4-tert-butyl-4'-methoxydibenzoylmethane, or β,β-diphenylacrylate derivatives, such as 2-ethylhexyl α-cyano-β,β-diphenylacrylate; p-aminobenzoic acid, cinoxate, diethanolamine, p-methoxycinnamate, digalloyl trioleate, dioxybenzone, ethyl 4->bis>hydroxypropyl!aminobenzoate, 2-ethylhexyl 2-cyano-3,3-diphenylacrylate, ethylhexyl p-methoxycinnamate, 2-ethyhexyl salicylate, glyceryl aminobenzoate, homosalate (3,3,5-trimethylcyclohexylsalicylate), lawsone (2-hydroxy-1,4-naphthoquinone) with or without dihydroxyacetone, methyl anthranilate, oxybenzone, Padimate A, Padimate O, 2-phenylbenzimidazole-5-sulfonic acid, triethanolamine salicylate, red petrolatum, and suisobenzone; titanium dioxide or zinc oxide.

The active agent may also be a cosmetic agent. Examples of cosmetic components include: Vitamin C; Alpha-tocopherol (Vitamin E analog); Ammonium lauryl Sulfate; Cocamidopropyl Betaine; Lauramide DEA; Cocamide DEA; Methyl paraben; Propyl paraben; Butyl paraben; Salicylic acid; Propylene glycol; EDTA; BHT; BHA; TBHQ; DMDM hydantoin; Imidazolidinyl urea; Potassium sorbate; Sodium Benzoate; phenoxyethanol; Polysorbate 20 and 80; Sodium laurylether sulfate; Oleyl betaine; Tego betaine; Sorbitol; Glycerin monolaurate; Glycerol stearate.

The active agent may also be a coloring agent for coloring hair or skin. A coloring agent is one which is able to change the color of skin, hair or nails. Color change may be effected through for example, a lightening or darkening of skin, hair or nails. Examples of coloring agents for hair include: 1,2,4-benzenetriacetate; 1,2,4-trihydroxybenzene; 1,3-bis-(2,4-diaminophenoxy)propane; 1,5-naphthalenediol; 1-naphthol; 2,3-naphthalenediol; 2,4-diamino-5-methylphenetol HCl; 2,4-diamino-5-methylphenoxyethanol HCl; 2,4-diaminodiphenylamine; 2,4-diaminophenol; 2,4-diaminophenol HCl; 2,4-diaminophenoxyethanol HCl; 2,6-bis(2-hydroxyethoxy)-3,5-pyridinediamine HCl; 2,6-diaminopyridine; 2,6-dimethoxy-3,5-pyridinediamine HCl; 2,7-naphthalenediol; 2-amino-3-hydroxypyridine; 2-amino-3-nitrophenol; 2-amino-4-hydroxyethylaminoanisole; 2-amino-4-hydroxyethylaminoanisole sulfate; 2-amino-6-chloro-4-nitrophenol; 2-aminomethyl-p-aminophenol HCl; 2-chloro-5-nitro-n-hydroxyethyl p-phenylenediamine; 2-chloro-6-ethylamino-4-nitrophenol; 2-chloro-p-phenylenediamine; 2-chloro-p-phenylenediamine sulfate; 2-hydroxyethyl picramic acid; 2-hydroxyethylamino-5-nitroanisole; 2-methoxymethyl-p-aminophenol HCl; 2-methyl-5-hydroxyethylaminophenol; 2-methylresorcinol; 2-nitro-5-glyceryl methylaniline; 2-nitro-n-hydroxyethyl-p-anisidine; 2-nitro-p-phenylenediamine; 3,4-diaminobenzoic acid; 3,4-methylenedioxyaniline; 3,4-methylenedioxyphenol; 3-methylamino-4-nitrophenoxyethanol; 3-nitro-4-aminophenoxyethanol; 3-nitro-p-cresol; 3-nitro-p-hydroxyethylaminophenol; 4,4-diaminodiphenylamine; 4,5-diamino-1-methylpyrazole HCl; 4,6-bis(2-hydroxyethoxy)-m-phenylenediamine HCl; 4-amino-2-hydroxytoluene; 4-amino-2-nitrodiphenylamine-2-carboxylic acid; 4-amino-3-nitrophenol; 4-amino-m-cresol; 4-chlororesorcinol; 4-hydroxyindole; 4-hydroxypropylamino-3-nitrophenol; 4-methoxytoluene-2,5-diamine HCl; 4-nitro-m-phenylenediamine; 4-nitro-o-phenylenediamine; 4-nitro-o-phenylenediamine HCl; 4-nitrophenyl aminoethylurea; 5-amino-2,6-dimethoxy-3-hydroxypyridine; 5-amino-6-chloro-o-cresol; 6-amino-m-cresol; 6-amino-o-cresol; 6-hydroxyindole; 6-methoxy-2,3-pyridinediamine HCl; 6-nitro-2,5-pyridinediamine; 6-nitro-o-toluidine; acacia catechu; acid black 1; acid black 52; acid blue 1; acid blue 3; acid blue 62; acid blue 74; acid blue 9; acid brown 13; acid green 1; acid green 25; acid green 50; acid orange 24; acid orange 3; acid orange 6; acid orange 7; acid red 14; acid red 18; acid red 27; acid red 33; acid red 35; acid red 51; acid red 52; acid red 73; acid red 87; acid red 92; acid red 95; acid violet 43; acid violet 9; acid yellow 1; acid yellow 23; acid yellow 3; acid yellow 73 sodium salt; basic blue 26; basic blue 41; basic blue 6; basic blue 7; basic blue 9; basic blue 99; basic brown 16; basic brown 17; basic brown 4; basic green 1; basic red 2; basic red 22; basic red 76; basic violet 14; basic yellow 11; basic yellow 57; brilliant black 1; chromium hydroxide green; chromium oxide greens; curry red; dihydroxyindole; direct black 51; direct blue 86; direct red 23; direct red 80; direct red 81; direct violet 48; direct yellow 12; disperse black 9; disperse blue 1; disperse blue 3; disperse blue 7; disperse brown 1; disperse orange 3; disperse red 11; disperse red 15; disperse red 17; disperse violet 1; disperse violet 4; fast green FCF; HC blue No. 10; HC blue No. 11; HC blue No. 12; HC blue No. 2; HC blue No. 4; HC blue No. 5; HC blue No. 6; HC blue No. 7; HC blue No. 8; HC blue No. 9; HC brown No. 1; HC brown No. 2; HC green No. 1; HC orange No. 1; HC orange No. 2; HC orange No. 3; HC red No. 1; HC red No. 10; HC red No. 11; HC red No. 13; HC red No. 3; HC red No. 7; HC red No. 8; HC red No. 9; HC violet No. 1; HC violet No. 2; HC yellow No. 10; HC yellow No. 1; HC yellow No. 12; HC yellow No. 13; HC yellow No. 2; HC yellow No. 4; HC yellow No. 5; HC yellow No. 6; HC yellow No. 7; HC yellow No. 8; HC yellow No. 9; henna; hydroquinone; hydroxyanthraquinoneaminopropyl methyl morpholinium methosulfate; hydroxybenzomorpholine; hydroxyethyl-2,6-dinitro-p-anisidine; hydroxyethyl-2-nitro-p-toluidine; hydroxyethyl-3,4-methylenedioxyaniline HCl; hydroxyethyl-p-phenylenediamine sulfate; hydroxyethylaminomethyl-p-aminophenol HCl; hydroxypropyl bis(n-hydroxyethyl-p-phenylenediamine) HCl; lawsone; lead acetate; m-aminophenol; m-aminophenol HCl; m-aminophenol sulfate; m-phenylenediamine; m-phenylenediamine sulfate; N,N-bis(2-hydroxyethyl)-p-phenylenediamine sulfate; N,N-diethyl-m-aminophenol; N,N-diethyl-m-aminophenol sulfate; N,N-dimethyl 2,6-pyridinediamine HCl; N,N-dimethyl-p-phenylenediamine; N,N-dimethyl-p-phenylenediamine sulfate; N,N-bis(2-hydroxyethyl)-2-nitro-p-phenylenediamine; N,N-dimethyl-n-hydroxyethyl-3-nitro-p-phenylendiamine; n-ethyl-3-nitro PABA; n-methoxyethyl-p-phenylenediamine HCl; n-methyl-3-nitro-p-phenylenediamine; n-phenyl-p-phenylenediamine; n-phenyl-p-phenylenediamine HCl; n-phenyl-p-phenylenediamine sulfate; o-aminophenol; p-aminophenol; p-aminophenol HCl; p-aminophenol sulfate; p-methylaminophenol; p-methylaminophenol sulfate; p-phenylenediamine; p-phenylenediamine HCl; p-phenylenediamine sulfate; phenyl methyl pyrazolone; phloroglucinol; picramic acid; pigment blue 15; pigment green 7; pigment red 112; pigment red 172 aluminum lake; pigment red 4; pigment red 48; pigment red 5; pigment red 57; pigment red 57:1; pigment red 63:1; pigment red 64:1; pigment red 83; pigment red 90:1 aluminum lake; pigment violet 19; pigment violet 23; pigment yellow 12; pigment yellow 13; pigment yellow 73; ponceau sx; resorcinol; silver nitrate; sodium picramate; solvent black 3; solvent green 3; solvent green 7; solvent orange 1; solvent red 1; solvent red 23; solvent red 3; solvent red 43; solvent red 48; solvent red 72; solvent red 73; solvent violet 13; solvent yellow 29; solvent yellow 33; solvent yellow 44; sunset yellow, thymol; toluene-2,5-diamine; toluene-2,5-diamine sulfate; toluene-3,4-diamine; ultramarines; VAT red 1; m- and p-phenylenediamines, their N-substituted derivatives and their salts; N-substituted derivatives of o-phenylenediamines; methylphenylenediamines, their N-substituted derivatives and their salts; diaminophenols; hydroquinone; alpha-naphthol; lead acetate.

Coloring agents also include bleaching agents such as ammonium persulfate; hydroquinone and strontium dioxide.

Other examples of coloring agents are cosmetic colorants which include: acid red 195; aluminum stearate; anthocyanins; beta vulgaris; beta vulgaris; bismuth oxychloride; bromocresol green; bromothymol blue; calcium stearate; capsanthin/capsorubin caramel; CI 10006; CI 10020; CI 10316; CI 10316; CI 11680; CI 11710; CI 11725; CI 11920; CI 12010; CI 12085; CI 12120; CI 12150; CI 12370; CI 12420; CI 12480; CI 12490; CI 12700; CI 13015; CI 14270; CI 14700; CI 14700; CI 14720; CI 14815; CI 15510; CI 15510; CI 15525; CI 15580; CI 15620; CI 15630; CI 15800; CI 15850; CI 15850; CI 15850; CI 15850; CI 15850; CI 15850; CI 15850; CI 15850; CI 15850; CI 15850; CI 15850; CI 15865; CI 15865; CI 15880; CI 15980; CI 15985; CI 15985; CI 16035; CI 16185; CI 16185; CI 16230; CI 16255; CI 16290; CI 17200; CI 17200; CI 18050; CI 18130; CI 18690; CI 18736; CI 18820; CI 18965; CI 19140; CI 19140; CI 19140; CI 20040; CI 20170; CI 20470; CI 21100; CI 21108; CI 21230; CI 24790; CI 26100; CI 27290; CI 27755; CI 28440; CI 40215; CI 40800; CI 40820; CI 40825; CI 40850; CI 42045; CI 42051; CI 42053; CI 42080; CI 42090; CI 42090; CI 42090; CI 42100; CI 42170; CI 42510; CI 42520; CI 42735; CI 44045; CI 44090; CI 45100; CI 45190; CI 45220; CI 45350; CI 45350; CI 45370; CI 45370; CI 45370; CI 45370; CI 45380; CI 45380; CI 45380; CI 45380; CI 45396; CI 45405; CI 45410; CI 45410; CI 45410; CI 45410; CI 45410; CI 45410; CI 45410; CI 45425; CI 45425; CI 45425; CI 45430; CI 45430; CI 47000; CI 47005; CI 47005; CI 50325; CI 50420; CI 51319; CI 58000; CI 59040; CI 60724; CI 60725; CI 60730; CI 61565; CI 61570; CI 61585; CI 62045; CI 69800; CI 69825; CI 71105; CI 73000; CI 73015; CI 73015; CI 73360; CI 73385, CI 73900; CI 73915; CI 74100; CI 74160; CI 74180; CI 74260; CI 75100; CI 75120; CI 75125; CI 75130; CI 75135; CI 75170; CI 75300; CI 75470; CI 75810; CI 75810; CI 75810; CI 75810; CI 77000; CI 77002; CI 77004; CI 77004; CT 77004; CI 77007; CT 77015; CI 77120; CI 77163; CI 77220; CI 77231; CI 77266; CI 77267; CI 77268:1; CI 77288; CI 77289; CI 77346; CI 77400; CI 77480; CI 77489; CI 77491; CI 77492; CI 77499; CI 77510; CI 77713; CI 77742; CI 77745; CI 77820; CI 77891; CI 77947; lactoflavin; magnesium stearate; riboflavin and zinc stearate.

The active agent may also be a moisturizing agent. A moisturizing agent is an agent which softens and smoothens skin and in some instances hair. Some moisturizing agents are also humectants in that they are able to hold and retain moisture. Emollient agents can be moisturing agents. Moisturizing agents can be used soften skin prior to abrasive events such as shaving. In these latter embodiments, the composition of the invention comprising a moisturizing agent can be supplied in a shaving gel or creme. Examples of moisturizing agents include: proteoglycans and glycosaminoglycans including hyaluronic acid, crosslinked hyaluronic acid, derivatized hyaluronic acid, chondroitin sulfate; mono- and poly-hydroxyl containing chemicals such as glycerin, sorbitol; pyrrolidine carboxylic acid; proteins such as hydrolyzed animal and vegetable protein, collagens, derivatized collagens, elastins; allantoin; polymer skin conditioning agents; polyols such as glycerol; chitosans; derivatized chitosans; and polyglutamine.

Other examples of moisturizing agents include D,L-panthenol, D-panthenol, vitamin A palmitate, vitamin E acetate, methylsilanetriol mannuronate, natural oils such as tallow oil, macadamia nut oil, borage oil, evening primrose oil, kukui nut oil, rice bran oil, tea tree oil, a medium chain fatty acid ester of glycerol, such as glycerol triheptanoate, glyceryl trioctanoate, glycerol trioctanoate, mineral water, silicones, silicone derivatives; allantoin; dipotassium glycyrrhizinate; stearyl glycyrrhizinate; squalane NF; squalane EX; cetyl ester wax; orange roughy oil; hydrogenated phospholipids; hydrocarbon oils and waxes, such as mineral oil, polyethylene and paraffin; triglyceride esters, such as olive oil, avocado oil, and squalene; lanolin and derivatives; ether-esters, such as fatty acid esters of ethoxylated fatty alcohols; and fatty acids having 10 to 20 carbon atoms, such as lauric, myristic, oleyl, and stearate.

Emollients useful in the invention as moisturizers include: acetamidoethoxybutyl trimonium chloride; acetyl trioctyl citrate; acetylated castor oil; acetylated cetyl hydroxyprolinate; acetylated glycol stearate; acetylated hydrogenated cottonseed glyceride; acetylated hydrogenated lanolin; acetylated hydrogenated lard glyceride; acetylated hydrogenated tallow glyceride; acetylated hydrogenated tallow glycerides; acetylated hydrogenated vegetable glyceride; acetylated lanolin; acetylated lanolin alcohol; acetylated lanolin ricinoleate; acetylated lard glyceride; acetylated palm kernel glycerides; acetylated sucrose distearate; adeps bovis; adeps suillus; aleurites moluccana; allyl caproate;almond oil peg-6 esters; aloe barbadensis; althea officinalis; aluminum hydroxide; aluminum stearates; aluminum tristearate; amodimethicone/dimethicone copolyol; amp-isostearoyl hydrolyzed collagen; anacardium occidentale; apple peel wax; apricot kernel oil PEG-6 esters; arachidonic acid; arachidyl alcohol; arachidyl behenate; arachidyl glycol isostearate; arachidyl propionate; arachis hypogaea; arctium lappa; avena sativa; avocado oil PEG-11 esters; bassia latifolia; batyl alcohol; batyl isostearate; batyl stearate; bayberry wax; behenoxy dimethicone; behenyl/isostearyl beeswax; behenyl alcohol; behenyl behenate; behenyl erucate; behenyl isostearate; benzyl laurate; bis-diglyceryl/ caprylate/caprate/isostearate/hydroxystearate adipate; bis-diglyceryl caprylate/caprate/isostearate/stearate/ hydroxystearate adipate; bisphenylhexamethicone; borago officinalis; borago officinalis; brassica botrytis; brassica oleifera; brassica oleifera; brevoortia; bubulum; butyl acetyl ricinoleate; butyl isostearate; butyl myristate; butyl oleate; butyl stearate; butylene glycol dicaprylate/dicaprate; butylene glycol montanate; butyloctyl beeswax; butyloctyl oleate; butyrospermum parkii; butyroyl trihexyl citrate; butyrum; buxus chinensis; C10–18 triglycerides; C11–15 pareth-12 stearate; C11–15 pareth-3 oleate; C11–15 pareth-3 stearate; C12–13 alcohols; C12–13 alkyl lactate; C12–13 alkyl octanoate; C12–15 alcohols; C12–15 alkyl benzoate; C12–15 alkyl lactate; C12–15 alkyl octanoate; C12–15 pareth-12 oleate; C12–16 alcohols; C12–18 acid triglyceride; C13–14 isoparaffin; C15–18 glycol; C18–28 alkyl acetate; C18–36 acid glycol ester; C18–36 acid triglyceride; C18–38 alkyl beeswax; C18–70 isoparaffin; C20–40 alkyl behenate; C20–40 isoparaffin; C24–28 alkyl methicone; C30–45 alkyl methicone; C9–11 alcohols; Calendula officinalis; camelina sativa; cananga odorata; candelilla cera; canola; capryl glycol; caprylic/capric/diglyceryl succinate; caprylic/capric/lauric triglyceride; caprylic/capric/linoleic triglyceride; caprylic/capric/myristic/stearic triglyceride; caprylic/capric/stearic triglyceride; caprylic/capric glycerides; caprylic/capric triglyceride; carnauba; carthamus tinctorius; carthamus tinctorius; cera alba; ceratonia siliqua; ceratonia siliqua; cetearyl alcohol; cetearyl behenate; cetearyl candelillate; cetearyl isononanoate; cetearyl octanoate; cetearyl palmitate; cetyl acetate; cetyl acetyl ricinoleate; cetyl alcohol; cetyl C12–15-pareth-9 carboxylate; cetyl caprylate; cetyl dimethicone; cetyl esters; cetyl glycol; cetyl glycol isostearate; cetyl isononanoate; cetyl lactate; cetyl laurate; cetyl myristate; cetyl octanoate; cetyl oleate; cetyl palmitate; cetyl ricinoleate; cetyl stearate; cetylarachidol; chamomilla recutita; chimyl isostearate; cholesterol; cholesteryl hydroxystearate; cholesteryl isostearate; cholesteryl macadamiate; cholesteryl nonanoate; cholesteryl stearate; cistus ladaniferus; cocaminobutyric acid; cocaminopropionic acid; coco-caprylate/caprate; coco-rapeseedate; cocoglycerides; coconut acid; coconut alcohol; cocos nucifera; cocoyl glutamic acid; coenzyme a; corn acid; corn oil PEG-6 esters; corn oil PEG-8 esters; corylus americana; corylus avellana; cottonseed acid; cottonseed glyceride; cucumis sativus; cucurbita pepo; curcuma zedoaria; cyatheaceae; cyclomethicone; dalea spinosa; daucus carota; decyl alcohol; decyl isostearate; decyl myristate; decyl oleate; decyl succinate; decyltetradecanol; di-C12–13 alkyl malate; di-C12–13 alkyl tartrate; di-C12–15 alkyl adipate; dibutyl adipate; dibutyl sebacate; dicapryl adipate; dicaprylyl maleate; dicetyl adipate; dicocamine; dicocodimethylamine dilinoleate; dicocoyl pentaerythrityl distearyl citrate; didecene; diethyl palmitoyl aspartate; diethyl sebacate; diethyl succinate; diethylene glycol dibenzoate; diethylene glycol diisononanoate; diethylene glycol dioctanoate; diethylene glycol dioctanoate/diisononanoate; dihexyl adipate; dihydroabietyl behenate; dihydrocholesterol; dihydrocholesteryl octyldecanoate; dihydrogenated tallow phthalate; dihydrophytosteryl octyldecanoate; dihydroxyethyl soyamine dioleate; dihydroxyethylamino hydroxypropyl oleate; diisobutyl adipate; diisocetyl adipate; diisodecyl adipate; diisononyl adipate; diisopropyl adipate; diisopropyl dimer dilinoleate; diisopropyl sebacate; diisostearyl adipate; diisostearyl dimer dilinoleate; diisostearyl fumarate; diisostearyl glutarate; diisostearyl malate; dilaureth-7 citrate; dilauryl citrate; dilinoleic acid; dimethicone; dimethicone copolyol; imethicone copolyol almondate; dimethicone copolyol avocadoate; dimethicone copolyol beeswax; dimethicone copolyol cocoa butterate; dimethicone copolyol olivate; dimethicone copolyol phthalate; dimethicone copolyol shea butterate; dimethicone propylethylenediamine behenate; dimethiconol; dimethiconol hydroxystearate; dimethiconol isostearate; dimethiconol stearate; dimethyl adipate; dimethyl lauramine dimer dilinoleate; dimethyl lauramine isostearate; dimethyl maleate; dimethyl succinate; dimethyl tallowamine; dioctyl adipate; dioctyl dimer dilinoleate; dioctyl malate; dioctyl sebacate; dioctyl succinate; dioctylcyclohexane; dioctyldodecyl dimer dilinoleate; dipentaerythrityl hexaheptanoate/hexacaprylate/hexacaprate dipropyl adipate; dipropylene glycol dibenzoate; distearyldimethylamine dilinoleate; ditridecyl adipate; ditridecyl dimer dilinoleate; dodecyltetradecanol; dromiceius; elaeis guineensis; elaeis guineensis; epoxidized soybean oil; erucyl arachidate; erucyl erucate; erucyl oleate; ethiodized oil; ethyl arachidonate; ethyl avocadate; ethyl ester of hydrolyzed animal protein; ethyl isostearate; ethyl laurate; ethyl linoleate; ethyl linolenate; ethyl minkate; ethyl morrhuate; ethyl myristate; ethyl oleate; ethyl olivate; ethyl palmitate; ethyl pelargonate; ethyl persate; ethyl stearate; fish glycerides; gadi iecur; glycereth-7 triacetate; glycerin/oxybutylene copolymer stearyl ether; glyceryl/sorbitol oleate/hydroxystearate; glyceryl abietate; glyceryl adipate; glyceryl arachidate; glyceryl arachidonate; glyceryl behenate; glyceryl caprate; glyceryl caprylate; glyceryl caprylate/caprate; glyceryl cocoate; glyceryl diarachidate; glyceryl dibehenate; glyceryl dierucate; glyceryl dihydroxystearate; glyceryl diisopalmitate; glyceryl diisostearate; glyceryl dilaurate; glyceryl dilinoleate; glyceryl dimyristate; glyceryl dioleate; glyceryl dipalmitate; glyceryl dipalmitoleate; glyceryl diricinoleate; glyceryl distearate; glyceryl erucate; glyceryl hydroxystearate; glyceryl isostearate; glyceryl lanolate; glyceryl laurate; glyceryl laurate/oleate; glyceryl linoleate; glyceryl linolenate; glyceryl myristate; glyceryl octanoate/stearate/adipate; glyceryl oleate; glyceryl palmitate; glyceryl palmitate/stearate; glyceryl palmitate lactate; glyceryl ricinoleate; glyceryl sesquioleate; glyceryl stearate; glyceryl stearate citrate; glyceryl stearate diacetate; glyceryl stearate lactate; glyceryl triacetyl hydroxystearate; glyceryl triacetyl ricinoleate; glycine soja; glycine soja; glycol/butylene glycol montanate; glycol cetearate; glycol dibehenate; glycol dilaurate; glycol dioctanoate; glycol dioleate; glycol distearate; glycol ditallowate; glycol hydroxystearate; glycol oleate; glycol ricinoleate; glycol stearate; glycosaminoglycans; glycosphingolipids; gossypium; helianthus annus; helianthus annuus; heptylundecanol; hexadecyl methicone; hexamethyldisiloxane; hexanediol distearate; hexyl isostearate; hexyl laurate; hexyldecyl oleate; hordeum vulgare; hordeum vulgare; hydrogenated butylene/ethylene/styrene copolymer; hydrogenated C12–18 triglycerides; hydrogenated c6–14 olefin polymers; hydrogenated castor oil; hydrogenated castor oil laurate; hydrogenated coco-glycerides; hydrogenated coconut acid; hydrogenated coconut oil; hydrogenated cottonseed glyceride; hydrogenated cottonseed oil; hydrogenated ethylene/propylene/styrene copolymer; hydrogenated fish oil; hydrogenated jojoba oil; hydrogenated jojoba wax; hydrogenated lanolin; hydrogenated lard; hydrogenated menhaden oil; hydrogenated mink oil; hydrogenated olive oil unsaponifiables; hydrogenated orange roughy oil; hydrogenated palm/palm kernel oil PEG-6 esters; hydrogenated palm glyceride; hydrogenated palm glycerides; hydrogenated palm kernel glycerides; hydrogenated palm kernel oil; hydrogenated palm oil; hydrogenated peanut oil; hydrogenated polyisobutene; hydrogenated rapeseed oil; hydrogenated shark liver oil; hydrogenated soy glyceride; hydrogenated soybean glycerides; hydrogenated soybean oil; hydrogenated tallow; hydrogenated tallow acid; hydrogenated tallow alcohol; hydrogenated tallow glyceride; hydrogenated tallow glyceride citrate; hydrogenated tallow glyceride lactate; hydrogenated tallow glycerides; hydrogenated tallow glycerides citrate; hydrogenated vegetable glyceride; hydrogenated vegetable glycerides; hydrogenated vegetable glycerides phosphate; hydrogenated vegetable oil; hydrolyzed collagen; hydroxylated lanolin; hydroxylated milk glycerides; hydroxyoctacosanyl hydroxystearate; hyptis suaveolens; isatis tinctoria; isoamyl laurate; isobutyl myristate; isobutyl palmitate; isobutyl pelargonate; isobutyl stearate; isobutyl tallowate; isobutylated lanolin oil; isocetyl alcohol; isocetyl behenate; isocetyl isodecanoate; isocetyl linoleoyl stearate; isocetyl myristate; isocetyl palmitate; isocetyl salicylate; isocetyl stearate; isocetyl stearoyl stearate; isodeceth-2 cocoate; isodecyl citrate; isodecyl cocoate; isodecyl hydroxystearate; isodecyl isononanoate; isodecyl laurate; isodecyl myristate; isodecyl neopentanoate; isodecyl octanoate; isodecyl oleate; isodecyl palmitate; isodecyl stearate; isododecane; isododecene; isoeicosane; isohexadecane; isohexyl laurate; isohexyl neopentanoate; isohexyl palmitate; isolauryl behenate; isomerized jojoba oil; isononyl isononanoate; isopropyl arachidate; isopropyl avocadate; isopropyl behenate; isopropyl C12–15-pareth-9 carboxylate; isopropyl hydroxystearate; isopropyl isostearate; isopropyl lanolate; isopropyl laurate; isopropyl linoleate; isopropyl myristate; isopropyl oleate; isopropyl palmitate; isopropyl PPG-2-isodeceth-7 carboxylate; isopropyl ricinoleate; isopropyl stearate; isopropyl tallowate; isopropyl titanium triisostearate; isostearyl alcohol; isostearyl avocadate; isostearyl behenate; isostearyl benzoate; isostearyl erucate; isostearyl glyceryl pentaerythrityl ether; isostearyl isononanoate; isostearyl isostearate; isostearyl lactate; isostearyl myristate; isostearyl neopentanoate; isostearyl octanoate; isostearyl palmitate; isostearyl stearoyl stearate; isotridecyl isononanoate; isotridecyl myristate; jojoba alcohol; jojoba wax; juglans regia; lactis lipida; laneth-10 acetate; laneth-9 acetate; lanolin; lanolin; lanolin acid; lanolin alcohol; lanolin cera; lanolin linoleate; lanolin ricinoleate; lanosterol; lard glycerides; laureth-2 acetate; laureth-2 benzoate; laureth-2 octanoate; lauric/palmitic/oleic triglyceride; lauryl alcohol; lauryl behenate; lauryl cocoate; lauryl glycol; lauryl isostearate; lauryl lactate; lauryl myristate; lauryl oleate; lauryl palmitate; lauryl stearate; lauryldimonium hydroxypropyl hydrolyzed collagen; laurylmethicone copolyol; lavandula hybrida; lecithin; lesquerella fendleri; limnanthes alba; linoleic acid; linolenic acid; linoleyl lactate; linseed acid; linum usitatissimum; macadamia ternifolia; maleated soybean oil; mangifera indica; mango seed oil PEG-70 esters; MEL; methicone; methyl acetyl ricinoleate; methyl caproate; methyl caprylate; methyl caprylate/caprate; methyl cocoate; methyl dehydroabietate; methyl gluceth-20 benzoate; methyl glucose dioleate; methyl glucose laurate; methyl glucose sesquicaprylate/sesquicaprate; methyl glucose sesquicocoate; methyl glucose sesquiisostearate; methyl glucose sesquilaurate; methyl glucose sesquioleate; methyl glucose sesquistearate; methyl hydroxystearate; methyl laurate; methyl linoleate; methyl myristate; methyl oleate; methyl palmitate; methyl pelargonate; methyl ricinoleate; methyl stearate; mink oil PEG-13 esters; moringa pterygosperma; mortierella isabellina; musa sapientum;

mustela; mustela; myreth-2 myristate; myreth-3 caprate; myreth-3 laurate; myreth-3 myristate; myreth-3 octanoate; myreth-3 palmitate; myristoyl hydrolyzed collagen; myristyl alcohol; myristyl isostearate; myristyl lactate; myristyl lignocerate; myristyl myristate; myristyl neopentanoate; myristyl octanoate; myristyl propionate; myristyl stearate; neopentyl glycol dicaprate; neopentyl glycol dicaprylate/dicaprate; neopentyl glycol dicaprylate/dipelargonate/dicaprate; neopentyl glycol dioctanoate; nonyl acetate; octacosanyl glycol; octacosanyl glycol isostearate; octyl acetoxystearate; octyl cocoate; octyl hydroxystearate; octyl isononanoate; octyl isopalmitate; octyl isostearate; octyl laurate; octyl myristate; octyl neopentanoate; octyl octanoate; octyl oleate; octyl palmitate; octyl pelargonate; octyl stearate; octyldecanol; octyldodecanol; octyldodecyl behenate; octyldodecyl benzoate; octyldodecyl erucate; octyldodecyl lactate; octyldodecyl myristate; octyldodecyl neodecanoate; octyldodecyl neopentanoate; octyldodecyl octanoate; octyldodecyl oleate; octyldodecyl ricinoleate; octyldodecyl stearate; octyldodecyl stearoyl stearate; oenothera biennis; olea europaea; olea europaea; oleic/linoleic triglyceride; oleic/palmitic/lauric/myristic/linoleic triglyceride; oleic acid; oleostearine; oleoyl hydrolyzed collagen; oleyl acetate; oleyl alcohol; oleyl arachidate; oleyl erucate; oleyl lactate; oleyl lanolate; oleyl linoleate; oleyl myristate; oleyl oleate; oleyl stearate; olive oil PEG-10 esters; olive oil PEG-6 esters; olus; omental lipids; orange peel wax; orbignya oleifera; oryza sativa; oryza sativa; ovum; ozonized jojoba oil; palm glyceride; palm glycerides; palm kernel acid; palm kernel alcohol; palm kernel glycerides; palm kernel wax; palmitic acid; palmitoyl hydrolyzed collagen; pantethine; papaver orientale; paraffin; paraffinum liquidum; PCA glyceryl oleate; peanut oil PEG-6 esters; PEG/PPG-125/30 copolymer; PEG/PPG-35/9 copolymer; PEG-10 coconut oil esters; PEG-10 hydrogenated lanolin; PEG-10 lanolin; PEG-10 polyglyceryl-2 laurate; PEG-11 castor oil; PEG-2 milk solids; PEG-20 hydrogenated lanolin; PEG-20 methyl glucose distearate; PEG-200 hydrogenated glyceryl palmate; PEG-4 proline linoleate; PEG-4 proline linolenate; PEG-5 glyceryl triisostearate; PEG-5 hydrogenated lanolin; PEG-5 pentaerythrityl ether; PEG-5 tricetyl citrate; PEG-5 tridecyl citrate; PEG-5 trilauryl citrate; PEG-5 trimyristyl citrate; PEG-5 tristearyl citrate; PEG-75 lanolin; PEG-8 hydrogenated fish glycerides; PEG-8 linoleate; PEG-8 linolenate; pellis lipida; pentadecyl alcohol; pentadesma butyracea; pentadoxynol-200; pentaerythrityl dioleate; pentaerythrityl isostearate/caprate/caprylate/adipate; pentaerythrityl stearate; pentaerythrityl stearate/caprate/caprylate adipate; pentaerythrityl tetraabietate; pentaerythrityl tetraacetate; pentaerythrityl tetrabehenate; pentaerythrityl tetrabenzoate; pentaerythrityl tetracaprylate/caprate; pentaerythrityl tetracocoate; pentaerythrityl tetraisononanoate; pentaerythrityl tetraisostearate; pentaerythrityl tetralaurate; pentaerythrityl tetramyristate; pentaerythrityl tetraoctanoate; pentaerythrityl tetraoleate; pentaerythrityl tetrapelargonate; pentaerythrityl tetrastearate; pentaerythrityl trioleate; pentahydrosqualene; perfluoropolymethylisopropyl ether; persea gratissima; persea gratissima; petrolatum; petroleum hydrocarbon; phenyl dimethicone; phenyl methicone; phenyl trimethicone; phosphatidylcholine; pimenta acris; piscum iecur; pistacia vera; placental lipids; polyglyceryl-4 cocoate; polygonum aviculare; polyisoprene; polypentene; polyquaternium-2; polysilicone-3; polysilicone-4; polysilicone-5; PPG-1 trideceth-6; PPG-1-ceteth-1; PPG-1-ceteth-10; PPG-1-ceteth-20; PPG-1-ceteth-5; PPG-10 butanediol; PPG-10 cetyl ether phosphate; PPG-10 jojoba acid; PPG-10 jojoba alcohol; PPG-10 methyl glucose ether; PPG-10 oleyl ether; PPG-11 stearyl ether; PPG-12; PPG-12/SMDI copolymer; PPG-12 butyl ether; PPG-12-PEG-50 lanolin; PPG-12-PEG-65 lanolin oil; PPG-15; PPG-15 stearyl ether; PPG-15 stearyl ether benzoate; PPG-17; PPG-17 butyl ether; PPG-17 dioleate; PPG-2 butyl ether; PPG-2 hydrogenated tallowamine; PPG-2 isostearate; PPG-2 lanolin alcohol ether; PPG-2 myristyl ether propionate; PPG-2-buteth-2; PPG-2-ceteth-1; PPG-2-ceteth-5; PPG-20; PPG-20 butyl ether; PPG-20 lanolin alcohol ether; PPG-20 methyl glucose ether acetate; PPG-20 oleyl ether; PPG-23 oleyl ether; PPG-23-steareth-34; PPG-25 butyl ether phosphate; PPG-26; PPG-26 butyl ether; PPG-26 oleate; PPG-3 myristyl ether; PPG-3-deceth-2 carboxylic acid; PPG-3-ISODECETH-1, PPG-30; PPG-30 cetyl ether; PPG-30 isocetyl ether; PPG-30 lanolin alcohol ether; PPG-30 oleyl ether; PPG-34; PPG-36 oleate; PPG-36-buteth-36; PPG-37 oleyl ether; PPG-4 jojoba acid; PPG-4 jojoba alcohol; PPG-4 laureth-2; PPG-4 laureth-7; PPG-4 lauryl ether; PPG-4 myristyl ether; PPG-4-buteth-4; PPG-4-ceteth-20; PPG-4-deceth-4; PPG-40-PEG-60 lanolin oil; PPG-5 lanolin alcohol ether; PPG-5 lanolin wax; PPG-5 lanolin wax glyceride; PPG-5 pentaerythrityl ether; PPG-5-buteth-5; PPG-5-laureth-5; PPG-50 oleyl ether; PPG-52 butyl ether; PPG-6-deceth-4; PPG-6-deceth-9; PPG-6-laureth-3; PPG-6-sorbeth-245; PPG-6-sorbeth-500; PPG-68-PEG-10 trimethylolpropane; PPG-7/succinic acid copolymer; PPG-7 lauryl ether; PPG-8 deceth-6; PPG-8 polyglyceryl-2 ether; PPG-9; PPG-9 diglyceryl ether; PPG-9 laurate; PPG-9-steareth-3; pristane; propylene glycol behenate; propylene glycol capreth-4; propylene glycol caprylate; propylene glycol ceteth-3 acetate; propylene glycol ceteth-3 propionate; propylene glycol citrate; propylene glycol cocoate; propylene glycol dicaprate; propylene glycol dicaproate; propylene glycol dicaprylate; propylene glycol dicaprylate/dicaprate; propylene glycol dicocoate; propylene glycol diisostearate; propylene glycol dilaurate; propylene glycol dioctanoate; propylene glycol dioleate; propylene glycol dipelargonate; propylene glycol distearate; propylene glycol hydroxystearate; propylene glycol isoceth-3 acetate; propylene glycol isostearate; propylene glycol laurate; propylene glycol linoleate; propylene glycol linolenate; propylene glycol myristate; propylene glycol myristyl ether; propylene glycol myristyl ether acetate; propylene glycol oleate; propylene glycol oleth-5; propylene glycol ricinoleate; propylene glycol soyate; propylene glycol stearate; prunus armeniaca; prunus armeniaca; prunus avium; prunus dulcis; prunus persica; rapeseed glyceride; rapeseed glycerides; red petrolatum; rhus succedanea; ricinoleic acid; ricinus communis; rosa canina; rosa moschata; safflower glyceride; salmo; salvia hispanica; sesamum indicum; sesamum indicum; shellac; shellac cera; shorea stenoptera; silica dimethyl silylate; silica silylate; simethicone; sorbitan distearate; soy acid; sphingolipids; squalane; squalene; squali iecur; stearoxy dimethicone; stearoxymethicone/dimethicone copolymer; stearoxytrimethylsilane; stearyl/aminopropyl methicone copolymer; stearyl acetate; stearyl alcohol; stearyl behenate; stearyl benzoate; stearyl caprylate; stearyl citrate; stearyl dimethicone; stearyl erucate; stearyl glycol; stearyl glycol isostearate; stearyl heptanoate; stearyl lactate; stearyl linoleate; stearyl methicone; stearyl octanoate; stearyl stearate; stearyl stearoyl stearate; sucrose distearate; sulfurized jojoba oil; sunflower seed oil glyceride; sunflower seed oil glycerides; synthetic candelilla wax; synthetic carnauba; synthetic japan wax; synthetic jojoba oil; synthetic wax; tall oil acid; tall oil glycerides; tall oil sterol; tallol; tallow acid; tallow alcohol; tallow glyceride; tallow glycerides; taraktogenos kurzii;

tetrabutoxypropyl trisiloxane; tetradecyleicosanol; tetradecyleicosyl stearate; tetradecyloctadecanol; tetramethyl tetraphenyl trisiloxane; theobroma cacao; tri-C12–13 alkyl citrate; triarachidin; tribehenin; tricaprin; tricaprylin; tricaprylyl citrate; tridecyl alcohol; tridecyl behenate; tridecyl cocoate; tridecyl erucate; tridecyl isononanoate; tridecyl myristate; tridecyl neopentanoate; tridecyl octanoate; tridecyl stearate; tridecyl stearoyl stearate; tridecyl trimellitate; trierucin; triheptylundecanoin; trihydroxymethoxystearin; trihydroxystearin; triisocetyl citrate; triisononanoin; triisopalmitin; triisopropyl trilinoleate; triisostearin; triisostearin PEG-6 esters; triisostearyl citrate; triisostearyl trilinoleate; trilaurin; trilauryl citrate; trilinoleic acid; trilinolein; trilinolenin; trimethyl pentaphenyl trisiloxane; trimethylolpropane tricaprylate/tricaprate; trimethylolpropane tricocoate; trimethylolpropane triisostearate; trimethylolpropane trilaurate; trimethylolpropane trioctanoate; trimethylolpropane tristearate; trimethylsiloxysilicate; trimethylsilylamodimethicone; trimyristin; trioctanoin; trioctyldodecyl citrate; triolein; triolein PEG-6 esters; trioleyl phosphate; tripalmitin; tripalmitolein; triphenyl trimethicone; tripropylene glycol citrate; triricinolein; tris(tributoxysiloxy)methylsilane; trisebacin; tristearin; tristearyl citrate; triticum vulgare; triticum vulgare; triundecanoin; undecylpentadecanol; vegetable glycerides phosphate; vitis vinifera; wheat germ acid; wheat germ glycerides; *zea mays*.

Humectants useful in the invention as moisturizing agents include: 1,2,6-hexanetriol; acetamide MEA; aluminum hydroxide; arachidyl glycol; arginine PCA; butoxypropanol; butylene glycol; butyloctanol; capryl glycol; carboxymethyl chitosan succinamide; chitosan PCA; copper acetyl tyrosinate methylsilanol; copper PCA; copper PCA methylsilanol; cyclomethicone; diglycerin; dimethicone copolyol acetate; dimethicone copolyol adipate; dimethicone copolyol behenate; dimethicone copolyol butyl ether; dimethicone copolyol hydroxystearate; dimethicone copolyol isostearate; dimethicone copolyol laurate; dimethicone copolyol methyl ether; dimethicone copolyol phosphate; dimethicone copolyol stearate; dimethicone copolyolamine; dimethicone silylate; dimethyl imidazolidinone; dimethylsilanol hyaluronate; dipotassium glycyrrhizate; erythritol; ethoxydiglycol; fructose; glucamine; gluconic acid; glucose; glucose glutamate; glucuronic acid; glutamic acid; glutamic acid; glycereth-12; glycereth-20; glycereth-26; glycereth-7; glycerin; glycogen; glycyrrhetinyl stearate; glycyrrhizic acid; heilmoor clay; hexacosyl glycol; hexanediol beeswax; hexanetriol beeswax; hexyldecanol; histidine; histidine; hyaluronic acid; hydrogenated honey; hydrogenated starch hydrolysate; hydrolyzed collagen; hydrolyzed elastin; hydrolyzed glycosaminoglycans; hydrolyzed keratin; hydrolyzed silk; hydrolyzed soy protein; hydrolyzed wheat protein/dimethicone copolyol phosphate copolymer; hydroxyethyl sorbitol; inositol; inositol hexa-PCA; isopropyl hydroxybutyramide dimethicone copolyol; lactamide MEA; lactic acid; lactitol; lactose; lauryl PCA; lysine PCA; lysine PCA; lysine PCA; magnesium PCA; maltitol; manganese PCA; mannitol; MEL; menthyl PCA; methoxy PEG-10; methoxy PEG-100; methoxy PEG-16; methoxy PEG-40; methyl gluceth-10; methyl gluceth-20; methyl glucose dioleate; methylsilanol PCA; octyl PCA; PCA; PEG-10; PEG-10 propylene glycol; PEG-100; PEG-12; PEG-135; PEG-14; PEG-150; PEG-16, PEG-18; PEG-180; PEG-2 lactamide; PEG-20; PEG-20 stearate; PEG-200; PEG-240; PEG-25M; PEG-3 stearate; PEG-32; PEG-4; PEG-40; PEG-45M; PEG-6; PEG-60; PEG-75; PEG-8; PEG-8 stearate; PEG-9; PEG-90; placental protein; polydextrose; polyglucuronic acid; polyglycerin-3; polyglyceryl sorbitol; polysilicone-1; polysilicone-2; potassium dimethicone copolyol panthenyl phosphate; potassium dimethicone copolyol phosphate; potassium PCA; PPG-20 methyl glucose ether; PPG-20 methyl glucose ether distearate; PPG-38-buteth-37; propylene glycol; pyridoxine dilaurate; saccharide isomerate; serica; serum albumin; silk amino acids; sodium carboxymethyl chitin; sodium lactate; sodium mannuronate methylsilanol; sodium PCA; sodium PCA; sodium PCA methylsilanol; sodium PG-propyl thiosulfate dimethicone; sodium polyglutamate; soluble collagen; sorbitol; soy sterol; sucrose; sulfated castor oil; TEA-lactate; TEA-PCA; trehalose; tricontanyl PVP; trifluoromethyl C1–4 alkyl dimethicone; trilactin; urea; xylitol; *zea mays*; zinc PCA.

The active agent can also be a depilatory agent. A depilatory agent is an agent which removes body hair. Examples of depilatory agents include: alkali sulphides; alkaline earth sulphides; ammonium thioglycolate; ammonium thiolactate; barium sulfide; calcium sulfide; calcium thioglycolate; ethanolamine thioglycolate; glyceryl thioglycolate; isooctyl thioglycolate; lithium sulfide; magnesium sulfide; magnesium thioglycolate; mercaptopropionie acid; potassium sulfide; potassium thioglycolate; sodium sulfide; sodium thioglycolate; strontium sulfide; strontium thioglycolate; thioglycerin; thioglycollic acid and its salts; thiolactic acid; and zinc sulfide.

A preferred cosmetic agent is any of the known bulking agents which can be added to the hair or nails to provide 'body' and strength. Bulking agents are well known to those of ordinary skill in the art. Examples of bulking agents generally include cationic surfactant/polymers, fatty alcohols (non-ionic surfactant), waxes or esters, non-ionic polymers (e.g. polyglycols) for thickening, and insoluble silicone. The preferred bulking agent is the cationic surfactant, which places a dispersive charge on the hair. Examples of cationic surfactants include: quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethy-ammonium hydroxide, hexadecyltrimethylammonium hydroxide, cetyltrimethylammonium hydroxide, octyldimethylbenzylammonium hydroxide, decyldimethyl-benzylammonium hydroxide, stearyldimethylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof, e.g., chlorides; cetylpyridinium hydroxide or salts thereof, e.g., chloride; Quaternium-5, Quaternium-31, Quaternium 18 and mixtures thereof. Additional bulking agents can be solutions of proteins, peptides, and polynucleotides or combinations thereof. Particular bulking agents include collagen, keratins, plant structural proteins, silk, fibrin, mucopolysaccharide and elastin. Other examples of bulking agents include: polylysine; biotin, panthenol, glycoprotein, and mucopolysaccharide; amodimethicone; acrylates; dimethicone copolymer; di-isobutyl adipate; isododecane; polypropylene glycol, glycerol, disaccharides, urea, dithiothreitol, edta, methyl paraben, propylparaben; polyvinylpyrrolidone and copolymers or derivatives thereof; for example, copolymers with the ethyl or butyl ester of PVA/MA (partially neutralized), copolymers with vinyl acetate/crotonic acid, copolymers of PVP/VA in all proportions, Polyquaternium-11, and copolymers with ethyl methacrylate/oleyl methacrylate/ diethylaminoethyl methacrylate quaternized with dimethyl sulfate, as well as carboxyvinyl polymers, such as hydroxyethyl cellulose, hydroxypropyl methylcellulose, and guar gum, zanthan gum, tragacanth gum, and other natural viscosity boosters; ceramide; copolymers of vinyl acetate and crotonic acid, terpolymers of vinyl acetate, crotonic acid and a vinyl ester of an alpha-branched saturated aliphatic monocarboxylic acid such as vinyl neodecanoate, and copolymers of methyl vinyl ether and maleic anhydride (molar ratio about 1:1) wherein such copolymers are 50% esterified with a saturated aliphatic alcohol containing from 1 to 4 carbon atoms such as ethanol or butanol; and acrylic copolymers and terpolymers containing acrylic acid or methacrylic acid as the anionic radical containing moiety such as terpolymers of methacrylic acid, butylacrylate and ethyl methacrylate which is presently the preferred acrylic polymer.

Bulking agents can be used as hair conditioning or hair fixative agents. Hair conditioning agents are agents which improve the appearance, texture and sheen of hair as well as increasing hair body or suppleness. Usually these compounds facilitate hair styling. Examples of hair conditioning agents include: Acetamide MEA; Acetamidoethoxybutyl Trimonium Chloride; Acetylated Lanolin; Acetylated Lanolin Alcohol; Acetylmethionyl Methylsilanol Elastinate; Acrylates/Carbamate Copolymer; Alanine; Albumen; Alfalfa (Medicago Sativa) Oil Unsaponifiables; Almondamidopropalkonium Chloride; Almondamidopropyl Betaine; Aluminum Capryloyl Hydrolyzed Collagen; Aluminum Undecylenoyl Collagen Amino Acids; Amino Bispropyl Dimethicone; Aminopropyl Dimethicone; Aminopropyl Laurylglutamine; Ammonium Caseinate; Ammonium Hydrolyzed Collagen; Ammonium Lauroyl Sarcosinate; Amodimethicone; Amodimethicone/Dimethicone Copolyol; Amodimethicone Hydroxystearate; AMP-Isostearoyl Gelatin/Keratin Amino Acids/Lysine Hydroxypropyltrimonium Chloride; AMP-Isostearoyl Hydrolyzed Collagen; AMP-Isostearoyl Hydrolyzed Soy Protein; AMP-Isostearoyl Hydrolyzed Wheat Protein; AMPD-Isostearcyl Hydrolyzed Collagen; AMPD-Rosin Hydrolyzed Collagen; Apricotamidopropyl Betaine; Apricotamidopropyl Ethyldimonium Ethosulfate; Argemone Mexicana Oil; Arginine; Arginine Aspartate; Asparagine; Aspartic Acid; Atelocollagen; Avocadamidopropyl Betaine; Avocado (Persea Gratissima) Oil Unsaponifiables; Babassuamide DEA; Babassuamidopropalkonium Chloride; Babassuamidopropylamine Oxide; Babassuamidopropyl Betaine; Beer; Behenamide DEA; Behenamide MEA; Behenamidopropyl Betaine; Behenamidopropyl Dimethylamine Behenate; Behenamidopropyl Dimethylamine Lactate; Behenamidopropyl Ethyldimonium Ethosulfate; Behenamidopropyl PG-Dimonium Chloride; Behenoyl PG-Trimonium Chloride; Behentrimonium Chloride; Behentrimonium Methosulfate; Behenyl Betaine; Behenyl Hydroxyethyl Imidazoline; Benzyltrimonium Hydrolyzed Collagen; Biotin; Bisphenylhexamethicone; Butoxy Chitosan; Buttermilk Powder; Butyloctyl Salicylate; Calcium Caseinate; Calcium Pantothenate; Canolamidopropyl Betaine; Canolamidopropyl Ethyldimonium Ethosulfate; Caproyl Sphingosine; Capryl/Capramidopropyl Betaine; Capryl Hydroxyethyl Imidazoline; Capryloyl Collagen Amino Acids; Capryloyl Glycine; Capryloyl Hydrolyzed Collagen; Capryloyl Hydrolyzed Keratin; Capryloyl Keratin Amino Acids; Capryloyl Pea Amino Acids; Capryloyl Quinoa Amino Acids; Capryloyl Silk Amino Acids; Caprylyl Glycol; Caprylyl Hydroxyethyl Imidazoline; Caprylyl Pyrrolidone; Carboxybutyl Chitosan; Carboxymethyl Chitin; Carboxymethyl Chitosan Succinamide; Carboxymethyl Isostearamidopropyl Morpholine; Carnitine; Carpronium Chloride; Casein; Catalase; Cauliflower (Brassica Oleracea Botrytis) Oil Unsaponifiables; Ceramide 1; Ceramide 2; Ceramide 3; Ceramide 4; Ceramide 5; Ceramide 1 A; Ceramide 6 II; Ceteartrimonium Chloride; Cetearyl Dimethicone/Vinyl Dimethicone Crosspolymer; Cetearyl Isononanoate; Cetearyl Octanoate; Cetearyl Palmitate; Cetyl Betaine; Cetyl Glycol; Cetyl Pyrrolidonylmethyl Dimonium Chloride; Cetyl Triethylammonium Dimethicone Copolyol Phthalate; Cholecalciferol Polypeptide; Cocamidoethyl Betaine; Cocamidopropylamine Oxide; Cocamidopropyl Amine Oxide; Cocamidopropyl Betaine; Cocamidopropyl Dimethylamine Dihydroxymethylpropionate; Cocamidopropyl Dimethylamine Hydrolyzed Collagen; Cocamidopropyl Dimethylamine Lactate; Cocamidopropyl Dimethylamine Propionate; Cocamidopropyl Dimethylamino-hydroxypropyl Hydrolyzed Collagen; Cocamidopropyl Dimethylammonium C8–16 Isoalkylsuccinyl Lactoglobulin Sulfonate; Cocamidopropyldimonium Hydroxypropyl Hydrolyzed Collagen; Cocamidopropyl Ethyldimonium Ethosulfate; Cocamidopropyl Hydroxysultaine; Cocamidopropyl Morpholine; Cocamidopropyl Morpholine Lactate; Cocamidopropyl PG-Dimonium Chloride; Cocamidopropyl PG-Dimonium Chloride Phosphate; Cocamidopropyltrimonium Chloride; Cocamine Oxide; Cocaminobutyric Acid; Cocaminopropionic Acid; Cocoalkonium Chloride; Cocoamphodipropionic Acid; Cocobetainamido Amphopropionate; Coco-Betaine; Cocodimonium Hydroxypropyl Hydrolyzed Casein; Cocodimonium Hydroxypropyl Hydrolyzed Collagen; Cocodimonium Hydroxypropyl Hydrolyzed Hair Keratin; Cocodimonium Hydroxypropyl Hydrolyzed Keratin; Cocodimonium Hydroxypropyl Hydrolyzed Rice Protein; Cocodimonium Hydroxypropyl Hydrolyzed Silk; Cocodimonium Hydroxypropyl Hydrolyzed Soy Protein; Cocodimonium Hydroxypropyl Hydrolyzed Wheat Protein; Cocodimonium Hydroxypropyl Silk Amino Acids; Coco-Ethyldimonium Ethosulfate; Coco-Hydroxysultaine; Coco-Morpholine Oxide; Coconut (Cocos Nucifera) Oil; Coco/Oleamidopropyl Betaine; Coco-Sultaine; Cocotrimonium Chloride; Cocotrimonium Methosulfate; Cocoyl Benzyl Hydroxyethyl Imidazolinium Chloride; Cocoyl Glutamic Acid; Cocoyl Hydrolyzed Collage; Cocoyl Hydrolyzed Keratin; Cocoyl Hydrolyzed Soy Protein; Cocoyl Hydroxyethyl Imidazoline; Cocoyl Hydroxyethylimidazolinium PG-Chloride phosphate; cocoyl sarcosinamide DEA; Cocyl sarcosine; Collagen; Collagen Amino Acids; Corn (Zea Mays) Gluten Protein; Corn (Zea Mays) Oil; Corn (Zea Mays) Oil Unsaponifiables; Crystallins; Cylcomethicone; Cysteine; Cysteine HCl; Cystine; DATEM; DEA-Cocoamphodipropionate; DEA-Cyclocarboxypropyloleate; DEA-Hydrolyzed Lecithin; DEA-Lauraminopropionate; Decyl Betaine; Decyl Mercaptomethylimidazole; Desamido Collagen; Dextran Hydroxypropyltrimonium Chloride; Diaminopyrimidine Oxide; Dibehenamidopropyldimethylamine Dilinoleate; DibehenylDjarachidyl Dimonium Chloride; Dibehenyldimonium Chloride; Dibehenyldimonium Methosulfate; Dibutyl Lauroyl Glutamide; Di-C12–15 Alkyl Dimonium Chloride; Di-C12–18 Alkyl Dimonium Chloride; Di-C14–18 Alkyl Dimonium Chloride; Dicapryl/Dicaprylyl Dimonium Chloride; Dicaptyloyl Cystine; Dicetyldiminium Chloride; Dicocodimethylamine Dilinoleate; Dicocodimonium Chloride; Dicocoylethyl Hydroxyethylmonium Methosolufate; Didecyldimonium Chloride; Diethylaminoethyl Cocoate; Diethylaminoethyl PEG-5 Cocoate; Diethylaminoethyl PEG-5 Laurate; Diethylaminoethyl Stearate; Diethylene Glycol Dibenzoate; Diethylene Glycol Diisononanoate; Diethylene Glycol Dioctanoate; Diethylene Glycol Dioctanoate/Diisononanoate; Diethylene Tricaseinamide; Dihyrogenated Palmoylethyl Hydroxyethylmonium Methosulfate; Dihydrogenated Palmoyl Hydroxyethylmonium Methosulfate; Dihydrogenated Tallowamidoethyl Hydroxyethylmonium Chloride; Dihydrogenated Tallowamidoethyl Hydroxyethylmonium Methosulfate; Dihydrogenated Tallow Benzylmonium Chloride; Dihyrodgenated Tallowethyl Hydroxyethylmonium Methosulate; Dihydrogenated Tallow Hydroxyethylmonium Methosulfate; Dihydrogenated Tallowoylethyl Hydroxyethylmonium Methosulfate; Dihydroxyethylamino Hydroxypropyl Oleate; Dihydroxyethyl C12–15 Alkoxypropylamine Oxide; Dihidroxyethyl Cocamine Oxide; Dihyroxyethyl Oleyl Glycinate; Dihydroxyethyl Soy Glycinate; Dihydroxyethyl Stearamine Oxide; Dihydroxyethyl Stearyl Glycinate; Dihydroxyethyl Tallowamine/IPDI Copolymer; Dihydroxyethyl Tallowamine Oleate; dihydroxyethyl Tallowamine Oxide; dihydroxyethyl Tallow Glycinate; Dihydroxypropyl PEG-5 Linoleammonium Chloride Phosphate; Diisostearamidopropyl Epoxypropylmonium Chloride; Dilaureth-4 Dimonium Chloride; Dilauryl Acetyl Dimonium Chloride; Dilauryldimonium Chloride; Dilinoleamidopropyl Dimethylamine Dimethicone Copolyol Phosphate; Dimenthicone Bisamino Hydroxypropyl Copolyol; Dimenthicone Copolyol; Dimethicone Copolyol Acetate; Dimethicone Copolyol Adipate; Dimethicone Copolyol Almondate; Dimethicone Copolyol Avocadoate; Dimethicone Copolyol Beeswax; Dimethicone Copolyol Bishydroxyethylamine; Dimethiocone Copolyol Borageate; Dimethicone Copolyol Butyl Ether; Dimethicone Copolyol Cocoa Butterate; Dimethicone Copolyol Dhupa Butterate; Dimethicone Copolyol Ethyl Ether; Dimethicone Copolyol Kokum Butterate; Dimethicone Copolyol Lactate; Dimethicone Copolyol Mango Butterate; Dimethicone Copolyol Methyl Ether; Dimethicone Copolyol Mohwa Butterate; Dimethicone Copolyol Olivate; Dimethicone Copolyol Phthalate; Dimethicone Copolyol Sal Butterate; Dimethicone Copolyol Shea Butterate; Dimethicone Copolyol Undecylenate; Dimethicone Hydroxyptropyl Trimonioum Chloride; Dimethicone/Mercaptopropyl Methicone Copolymer; Dimethicone Propyl PG-Betaine; Dimethicone/Sodium PG-Propyidimethicone Thiosulfate Copolymer; Dimethiconol Arginine; Dimethiconol Cysteine; Dimethiconol Lactate; Dimethiconol Panthenol; Dimethiconol/Silsesquioxane Copolymer; Dimethaxysilyl Ethylenediaminopropyl Dimethicone; Dimethylaminopropylamido PCA Dimethicone; Dimethyl Aspartic Acid; Dimethyl Glutamic Acid; Dimethyl Lauramine Dimer Dilinoleate; Dimethyl Lauramine Isostearate; Dimethyl Lauramine Oleate; DimethyIPABAmidopropyl Laurdimonium Tosylate; Dioctyldodeceth-2 Lauroyl Glutamate; Dioctyldodecyl Dodecanedioate; Dioctyldodecyl Lauroyl Glutamate; Dioleoyl EDTHP-Monium Methosulfate; Dioleoylethyl Hydroxyethylmonium Methosulfate; Dioleoylisopropyl Dimonium Methosulfate; Dipalmitoyl Cystine; Dipalmitoylethyl Dimonium Chloride; Dipalmitoylethyl Hydroxyethylmonium Methosulfate; Dipalmoylethyl Hydroxyethylmonium Methosulfate; Disodium Caproamphodiacetate; Disodium Caproamphodipropionate; Disodium Capryloamphodiacetate; Disodium Capryloamphodipropionate; Disodium Cocaminopropyl Iminodiacetate; Disodium Cocoamphocarboxyethylhydroxypropylsulfonate; Disodium Cocoamphodiacetate; Disodium Cocoamphodipropionate; Disodium Cystinyl Disuccinate; Disodium Dicarboxyethyl Cocopropylenediamine; Disodium Hydrogenated Tallow Glutamate; Disodium Isostearoamphodiacetate; Disodium Isostearoamphodipropionate; Disodium Laureth-5 Carboxyamphodiacetate; Disodium Lauriminodipropionate; Disodium Lauroamphodiacetate; Disodium Lauroamphodipropionate; Disodium Oleoamphodipropionate; Disodium PPG-2-Isodeceth-7 Carboxyamphodiacetate; Disodium Steariminodipropionate; Disodium Stearoamphodiacetate; Disodium Stearoyl Glutamate; Disodium Tallowamphodiacetate; Disodium Tallowiminodipropionate; Disodium Wheatgermamphodiacetate; Disoyamidoethyl Hydroxyethyl Ammonium Lactate; Disoydimonium Chloride; Disoyoylethyl Hydroxyethylmonium Methosulfate; Disteareth-6 Dimonium Chloride; Disteareth-2 Lauroyl Glutamate; Disteareth-5 Lauroyl Glutamate; Distearoylethyl Dimonium Chloride; Distearoylethyl Hydroxyethylmonium Methosulfate; Distearoylpropyl Trimonium Chloride; Distearyldimethylamine Dilinoleate; Distearyldimonium Chloride; Distearyl Epoxypropylmonium Chloride; Ditallowamidoethyl Hydroxypropylamine; Ditallowamidoethyl Hydroxypropylmonium Methosulfate; Ditallow Dimonium Cellulose Sulfate; Ditallowdimonium Chloride; Ditallowethyl Hydroxyethylmonium Methosulfate; Ditallowoylethyl Hydroxyethylmonium Methosulfate; Ditridecyldimonium Chloride; Dodecylbenzyltrimonium Chloride; Dodecylhexadecyltrimonium Chloride; Dodecylxylylditrimonium Chloride; Egg; Egg Oil; Egg Powder; Elastin; Elastin Amino Acids; Erucalkonium Chloride; Erucamidopropyl Hydroxysultaine; Ethyl Almondate; Ethyl Apricot Kernelate; Ethyl Biotinate; Ethyl Ester of Hydrolyzed Animal Protein; Ethyl Ester of Hydrolyzed Keratin; Ethyl Ester of Hydrolyzed Silk; Ethyl Glutamate; Ethyl Hydroxymethyl Oleyl Oxazoline; Ethyl Minkate; Ethyl Morrhuate; Ethyl Myristate; Ethyl Oleate; Ethyl Olivate; Ethyl Palmitate; Ethyl Pelargonate; Ethyl Persate; Ethyl Serinate; Ethyl Stearate; Ethyl Wheat Germate; Fibronectin; Gelatin; Gelatin/Keratin Amino Acids/Lysine Hydroxypropyltrimonium Chloride; Gelatin/Lysine/Polyacrylamide Hydroxypropyltrimonium Chloride; Ginseng Hydroxypropyltrimonium Chloride; Glucaric Acid; Glucose Oxidase; Glutamic Acid; Glutamine; Glutamyl Histamine; Glyceryl Collagenate; Glyceryl Lanolate; Glycine; Glycoproteins; Glycyl Glycine; Guar Hydroxypropyltrimonium Chloride; Hair Keratin Amino Acids; Hexyldecyl Ester of Hydrolyzed Collagen; Hexyldodecyl Salicylate; Hinokitiol; Histidine; Histidine HCl; Human Placental Enzymes; Human Placental Lipids; Human Placental Protein; Hydrogenated Lanolin; Hydrogenated Olive Oil Unsaponifiables; Hydrogenated Palmtrimonium Chloride; Hydrogenated Tallowalkonium Chloride; Hydrogenated Tallow Betaine; Hydrogenated Tallowoyl Glutamic Acid; Hydrogenated Tallowtrimonium Chloride; Hydrolyzed Actin; Hydrolyzed Casein; Hydrolyzed Collagen; Hydrolyzed Conchiorin Protein; Hydrolyzed Corn Protein; Hydrolyzed DNA; Hydrolyzed Egg Protein; Hydrolyzed Elastin; Hydrolyzed Extensin; Hydrolyzed Fibronectin; Hydrolyzed Glycosaminoglycans; Hydrolyzed Hair Keratin; Hydrolyzed Hemoglobin; Hydrolyzed Human Placental Protein; Hydrolyzed Keratin; Hydrolyzed Lupine Protein; Hydrolyzed Maple Sycamore Protein; Hydrolyzed Milk Protein; Hydrolyzed Oat Flour; Hydrolyzed Oat Protein; Hydrolyzed Oats; Hydrolyzed Pea Protein; Hydrolyzed Placental Protein; Hydrolyzed Potato Protein; Hydrolyzed Reticulin; Hydrolyzed Rice Bran Protein; Hydrolyzed Rice Protein; Hydrolyzed RNA; Hydrolyzed Serum Protein; Hydrolyzed Silk; Hydrolyzed Soy Protein; Hydrolyzed Soy Protein/Dimethicone Copolyol Acetate; Hydrolyzed Spinal Protein; Hydrolyzed Sweet Almond Protein; Hydrolyzed Vegetable Protein; Hydrolyzed Wheat Gluten; Hydrolyzed Wheat Protein; Hydrolyzed Wheat Protein/Dimethicone Copolyol Acetate; Hydrolyzed Wheat Protein Hydroxypropyl Polysiloxane; Hydrolyzed Wheat Protein/PEG-20 Acetate Copolymer; Hydrolyzed Yeast; Hydrolyzed Yeast Protein; Hydrolyzed Zein; Hydroxycaproyl Phytosphingosine; Hydroxycapryloyl Phytosphingosine; Hydroxycetyl Hydroxyethyl Dimonium Chloride; Hydroxyethyl Behenamidopropyl Dimonium Chloride; Hydroxyethyl Carboxymethyl; Cocamidopropylamine; Hydroxyethyl Cetyldimonium Chloride; Hydroxyethyl Cetyldimonium Phosphate; Hydroxyethyl Diphenyl Imidazoline; Hydroxyethyl Hydroxypropyl C12–15 Alkoxypropylamine Oxide; Hydroxyethyl Laurdimonium Chloride; Hydroxyethyl Tallowdimonium Chloride; Hydroxylauroyl Phytosphingosine; Hydroxyphenyl Glycinamide; Hydroxyproline; Hydroxypropyl Biscetearyldimonium Chloride; Hydroxypropyl Bisisostearamidopropyldimonium Chloride; Hydroxypropyl Bisoleyldimonium Chloride; Hydroxypropyl Bisstearyidimonium Chloride; Hydroxypropyldimethicone; Hydroxypropyl Guar Hydroxypropyltrimonium Chloride; Hydroxypropyltrimonium Gelatin; Hydroxypropyltrimonium Honey; Hydroxypropyltrimonium Hydrolyzed Casein; Hydroxypropyltrimonium Hydrolyzed Collagen; Hydroxypropyltrimonium Hydrolyzed Keratin; Hydroxypropyltrimonium Hydrolyzed Rice Bran Protein; Hydroxypropyltrimonium Hydrolyzed Silk; Hydroxypropyltrimonium Hydrolyzed Soy Protein; Hydroxypropyltrimonium Hydrolyzed Vegetable Protein; Hydroxypropyltrimonium Hydrolyzed Wheat Protein; Hydroxystearamidopropyl Trimonium Chloride; Hydroxystearamidopropyl Trimonium Methosulfate;Inositol; Iodized Corn Protein; Isobutylated Lanolin Oil; Isoleucine; Isostearamidopropylamine Oxide; Isostearamidopropyl Betaine; Isostearamidopropyl Epoxypropylmorpholinium Chloride; Isostearamidopropyl Ethyldimonium Ethosulfate; Isostearamidopropyl Ethylmorpholinium Ethosulfate; Isostearamidopropyl Laurylacetodimonium Chloride; Isostearamidopropyl Morpholine Oxide; Isostearamidopropyl PG-Dimonium Chloride; Isostearaminopropalkonium Chloride; Isostearoyl Hydrolyzed Collagen; Isostearoyl PG-Trimonium Chloride; Isostearyl Benzylimidonium Chloride; Isostearyl Ethyldimonium Chloride; Isostearyl Ethylimidazolinium Ethosulfate; Isostearyl Glyceryl Pentaerythrityl Ether; Isostearyl Hydroxyethyl Imidazoline; Isostearyl Laurdimonium Chloride; Isotridecyl Laurate; Isotridecyl Myristate; Jojoba Butter; Jojoba (Buxus Chinensis) Oil; Jojoba Wax; Juniperus Oxycedrus Tar; Keratin; Keratin Amino Acids; Lactamide MEA; Lactoferrin; Lactoglobulin; Lactoyl Methylsilanol Elastinate; Lactoyl Phytosphingosine; Laneth-9 Acetate; Laneth-10 Acetate; Lanolin; Lanolin Alcohol; Lanolin Linoleate; Lanolin Oil; Lanolin Ricinoleate; Lanolin Wax; Lanosterol; Lauramidopropyl-amine Oxide; Lauramidopropyl Betaine; Lauramidopropyl PG-Dimonium Chloride; Lauramine Oxide; Lauraminopropionic Acid; Laurdimonium Hydroxypropyl Hydrolyzed Soy Protein; Laurdimonium Hydroxypropyl Hydrolyzed Wheat Protein; Lauroamphodipropionic Acid; Lauroyl Collagen Amino Acids; Lauroyl Hydrolyzed Collagen; Lauroyl Hydrolyzed Elastin; Lauroyl Lysine; Lauroyl PG-Trimonium Chloride; Lauroyl Sarcosine; Lauroyl Silk Amino Acids; Laurtrimonium Bromide; Laurylamine Dipropylenediamine; Lauryl Aminopropylglycine; Lauryl Betaine; Lauryl Diethylenediaminoglycine; Lauryl Dimethylamine Cyclocarboxypropyloleate; Lauryldimonium Hydroxypropyl Hydrolyzed Casein; Lauryldimonium Hydroxypropyl Hydrolyzed Collagen; Lauryldimonium Hydroxypropyl Hydrolyzed Keratin; Lauryldimonium Hydroxypropyl Hydrolyzed Silk; Lauryldimonium Hydroxypropyl Hydrolyzed Soy Protein; Lauryl Glycol; Lauryl Hydroxyethyl Imidazoline; Lauryl Hydroxysultaine; Lauryl Methyl Gluceth-10 Hydroxypropyldimonium Chloride; Lauryl Myristate; Lauryl Pyrrolidone; Lauryl Sultaine; Lecithinamide DEA; Leucine; Linoleamide; Linoleamide DEA; Linoleamide MEA; Linoleamide MIPA; Linoleamidopropalkonium Chloride; Linoleamidopropyl Dimethylamine Dimer Dilinoleate; Linoleamidopropyl Ethyldimonium Ethosulfate; Linoleamidopropyl PG-Dimonium Chloride Phosphate Dimethicone; Linoleic Acid; Linolenic Acid; Lupin (Lupinus Albus) Oil Unsaponifiables; Lysine; Lysine Aspartate; Maltodextrin; Marmot Oil; MEA-Hydrolyzed Collagen; MEA-Hydrolyzed Silk; Methionine; Methyl Aspartic Acid; Methyl Glutamic Acid; Methyl Hydroxycetyl Glucaminium Lactate; Methyl Hydroxymethyl Oleyl Oxazoline; Methylsilanol Acetylmethionate; Methylsilanol Elastinate; Milkamidopropyl Amine Oxide; Milkamidopropyl Betaine; Milk Amino Acids; Milk Protein; Mineral Oil; Minkamidopropalkonium Chloride; Minkamidopropylamine Oxide; Minkamidopropyl Betaine; Minkamidopropyl Ethyldimonium Ethosulfate; Mink Oil; Mink Wax; Mixed Isopropanolamines Lanolate; Myristamidopropylamine Oxide; Myristamidopropyl Betaine; Myristamine Oxide; Myristaminopropionic Acid; Myristoyl Glutamic Acid; Myristoyl Hydrolyzed Collagen; Myristoyl Sarcosine; Myristyl Betaine; Myristyl/Cetyl Amine Oxide; Myristyl Hydroxyethyl Imidazoline; Niacin; Niacinamide; Nonfat Dry Colostrum; Nonfat Dry Milk; Norvaline; Oat (Avena Sativa) Protein; Octyldodecyl Lanolate; Octyldodecyltrimonium Chloride; Olealkonium Chloride; Oleamidopropylamine Oxide; Oleamidopropyl Betaine; Oleamidopropyl Dimethylamine Glycolate; Oleamidopropyl Dimethylamine Hydrolyzed Collagen; Oleamidopropyl Dimethylamine Lactate; Oleamidopropyl Dimethylamine Propionate; Oleamidopropyldimonium Hydroxypropyl Hydrolyzed Collagen; Oleamidopropyl Hydroxysultaine; Oleamidopropyl PG-Dimonium Chloride; Oleamine Bishydroxypropyltrimonium Chloride; Oleamine Oxide; Oleoyl Hydrolyzed Collagen; Oleoyl PG-Trimonium Chloride; Oleoyl Sarcosine; Oleyl Betaine; Oleyl Epoxypropyldimonium Chloride; Oleyl Hydroxyethyl Imidazoline; Oleyl Lanolate; Oleyl Linoleate; Oleyl Myristate; Oleyl Oleate; Oleyl Stearate; Olivamidopropylamine Oxide; Olivamidopropyl Betaine; Olivamidopropyl Dimethylamine Lactate; Olive (Olea Europaea) Oil Unsaponifiables; Ostrich Oil; Oxidized Keratin; Palmamidopropyl Betaine; Palmitamidopropylamine Oxide; Palmitamidopropyl Betaine; Palmitamine Oxide; Palmitoyl Collagen Amino Acids; Palmitoyl Glycine; Palmitoyl Hydrolyzed Collagen; Palmitoyl Hydrolyzed Milk Protein; Palmitoyl Hydrolyzed Wheat Protein; Palmitoyl Keratin Amino Acids; Palmitoyl Pea-Amino Acids; Palmitoyl PG-Trimonium Chloride; Palmitoyl Quinoa Amino Acids; Palmitoyl Silk Amino Acids; Palm Kernelamidopropyl Betaine; Pancreatin; Pantethine; Panthenol; Panthenyl Ethyl Ether; Panthenyl Ethyl Ether Acetate; Panthenyl Hydroxypropyl Steardimonium Chloride; Panthenyl Triacetate; Pantothenic Acid; Pantothenic Acid Polypeptide; Papain; PCA Dimethicone; PCA Ethyl Cocoyl Arginate; PEG-105 Behenyl Propylenediamine; PEG-2 Dimeadowfoamamidoethylmonium Methosulfate; PEG-3 Dioleoylamidoethylmonium Methosulfate; PEG-5 Ditridecylmonium Chloride; PEG-5 Hydrogenated Lanolin; PEG-10 Hydrogenated Lanolin; PEG-20 Hydrogenated Lanolin; PEG-24 Hydrogenated Lanolin; PEG-30 Hydrogenated Lanolin; PEG-70 Hydrogenated Lanolin; PEG-5 Lanolinamide; PEG-3 Lauramine Oxide; PEG-2 Milk Solids; PEG-5 Oleamide Dioleate; PEG-2 Oleammonium Chloride; PEG-8/SMDI Copolymer; PEG-15 Stearmonium Chloride; PEG-20 Tallow Ammonium Ethosulfate; PEG-15 Tallow Polyamine; PEG-3 Tallow Propylenedimonium Dimethosulfate; Pepsin; Petrolatum; PG-Hydroxyethylcellulose Cocodimonium Chloride; PG-Hydroxyethylcellulose Lauryldimonium Chloride; PG-Hydroxyethylcellulose Stearyldimonium Chloride; Phenylalanine; Phenyl Trimethicone; Phytosphingosine; Phytosteryl Macadamiate; Placental Enzymes; Placental Lipids; Placental Protein; Polybeta-Alanine; Polyglyceryl-2 Oleyl Ether; Polyglyceryl-4 Oleyl Ether; Polylysine; Polymethacrylamidopropyltrimonium Chloride; Polymethacrylamidopropyltrimonium Methosulfate; Potymethylglutamate; Polyquaternium-43; Polyquaternium-44; Polysilicone-1; Polysilicone-2; Polysilicone-3; Polysilicone-4; Polysilicone-5; Polysilicone-6; Polysilicone-7; Polysilicone-8; Polysilicone-10; Potassium Abietoyl Hydrolyzed Collagen; Potassium Caseinate; Potassium Cocoyl Glutamate; Potassium Cocoyl Glycinate; Potassium Coccyl Hydrolyzed Casein; Potassium Cocoyl Hydrolyzed Collagen; Potassium Cocoyl Hydrolyzed Corn Protein; Potassium Cocoyl Hydrolyzed Keratin; Potassium Cocoyl Hydrolyzed Potato Protein; Potassium Cocoyl Hydrolyzed Rice Bran Protein; Potassium Cocoyl Hydrolyzed Rice Protein; Potassium Cocoyl Hydrolyzed Silk; Potassium Cocoyl Hydrolyzed Soy Protein; Potassium Cocoyl Hydrolyzed Wheat Protein; Potassium Dihydroxyethyl Cocamine Oxide Phosphate; Potassium Dimethicone Copolyol Panthenyl Phosphate; Potassium Lauroyl Collagen Amino Acids; Potassium Lauroyl Glutamate; Potassium Lauroyl Hydrolyzed Collagen; Potassium Lauroyl Hydrolyzed Soy Protein; Potassium Lauroyl Wheat Amino Acids; Potassium Myristoyl Glutamate; Potassium Myristoyl Hydrolyzed Collagen; Potassium Oleoyl Hydrolyzed Collagen; Potassium Palmitoyl Hydrolyzed Wheat Protein; Potassium Stearoyl Hydrolyzed Collagen; Potassium Undecylenoyl Alginate; Potassium Undecylenoyl Carrageenan; Potassium Undecylenoyl Hydrolyzed Collagen; Potassium Undecylenoyl Hydrolyzed Corn Protein; Potassium Undecylenoyl Hydrolyzed Soy Protein; Potassium Undecylenoyl Hydrolyzed Wheat Protein; PPG-2-Buteth-2; PPG-2-Buteth-3; PPG-3-Buteth-5; PPG-4-Buteth-4; PPG-5-Buteth-5; PPG-5-Buteth-7; PPG-7-Buteth-10; PPG-9-Buteth-12; PPG-10-Buteth-9; PPG-12-Buteth-12; PPG-12-Buteth-16; PPG-15-Buteth-20; PPG-17-Buteth-17; PPG-20-Buteth-30; PPG-24-Buteth-27; PPG-26-Buteth-26; PPG-28-Buteth-35; PPG-30-Buteth-30; PPG-33-Buteth-45; PPG-36-Buteth-36; PPG-38-Buteth-37; PPG-2 Butyl Ether; PPG-4 Butyl Ether; PPG-5 Butyl Ether; PPG-9 Butyl Ether; PPG-12 Butyl Ether; PPG-14 Butyl Ether; PPC-15 Butyl Ether; PPG-16 Butyl Ether; PPG-17 Butyl Ether; PPG-18 Butyl Ether; PPG-20 Butyl Ether; PPG-22 Butyl Ether; PPG-24 Butyl Ether; PPG-26 Butyl Ether; PPG-30 Butyl Ether; PPG-33 Butyl Ether; PPG-40 Butyl Ether; PPG-52 Butyl Ether; PPG-53 Butyl Ether; PPG-9 Diethylmonium Chloride; PPG-2 Lanolin Alcohol Ether; PPG-5 Lanolin Alcohol Ether; PPG-10 Lanolin Alcohol Ether; PPG-20 Lanolin Alcohol Ether; PPG-30 Lanolin Alcohol Ether; PPG-10 Methyl Glucose Ether; PPG-20 Methyl Glucose Ether; PPG-20-PEG-20 Hydrogenated Lanolin; PPG-12-PEG-50 Lanolin; PPG-12-PEG-65 Lanolin Oil; PPG-40-PEG-60 Lanolin Oil; PPG-12/SMDI Copolymer; PPG-51/SMDI Copolymer; PPG-7/Succinic Acid Copolymer; Procollagen; Proline; Propyltrimonium Hydrolyzed Collagen; Propyltrimonium Hydrolyzed Soy Protein; Propyltrimonium Hydrolyzed Wheat Protein; Pyridoxine; Pyridoxine Dicaprylate; Pyridoxine Dilaurate; Pyridoxine Dioctenoate; Pyridoxine Dipalmitate; Pyridoxine HCl; Pyridoxine Tripalmitate; Quaternium-8; Quaternium-14; Quaternium-16; Quaternium-22; Quaternium-26; Quaternium-27; Quaternium-33; Quaternium-52; Quaternium-53; Quaternium-56; Quaternium-60; Quaternium-61; Quaternium-63; Quaternium-70; Quaternium-72; Quaternium-75; Quaternium-76 Hydrolyzed Collagen; Quaternium-77; Quaternium-78; Quaternium-79 Hydrolyzed Collagen; Quaternium-79 Hydrolyzed Keratin; Quaternium-79 Hydrolyzed Milk Protein; Quaternium-79 Hydrolyzed Silk; Quaternium-79 Hydrolyzed Soy Protein; Quaternium-79 Hydrolyzed Wheat Protein; Quaternium-80; Quaternium-81; Quaternium-82; Quaternium-83; Quaternium-85; Quaternium-86; Quinine; Rapeseed (Brassica; Campestris) Oil Unsaponifiables; Resorcinol Acetate; Ricinoleamidopropyl Betaine; Ricinoleamidopropyltrimonium Chloride; Ricinoleamidopropyltrimonium Methosulfate; Rosin Hydrolyzed Collagen; Rutin; Safflloweramidopropyl Ethyldimonium Ethosulfate; Salicylic Acid; Selenium Sulfide; Sericin; Serine; Serum Albumin; Serum Protein; Sesame (Sesamum Indicum) Oil Unsaponifiables; Sesamidopropylamine Oxide; Sesamidopropyl Betaine; Shea Butter (Butyrospermum Parkii) Unsaponifiables; Shellac Wax; Silicone Quaternium-1; Silicone Quaternium-2; Silicone Quaternium-3; Silicone Quaternium-4; Silicone Quaternium-5; Silicone Quaternium-6; Silicone Quaternium-7; Silicone Quaternium-8; Silicone Quaternium-9; Silicone Quaternium-10; Silicone Quaternium-11; Silicone Quaternium-12; Silicone Quaternium-13; Silk Amino Acids; Sodium C12–15 Alkoxypropyl Iminodipropionate; Sodium Caproamphoacetate; Sodium Caproamphohydroxypropylsulfonate; Sodium Caproamphopropionate; Sodium Capryloamphoacetate; Sodium Capryloamphohydroxypropylsulfonate; Sodium Capryloamphopropionate; Sodium Caseinate; Sodium Chondroitin Sulfate; Sodium C8–16 Isoalkylsuccinyl Lactoglobulin Suffonate; Sodium Cocaminopropionate; Sodium Cocoamphoacetate; Sodium Cocoamphohydroxypropylsulfonate; Sodium Cocoamphopropionate; Sodium Cocoyl Collagen Amino Acids; Sodium Cocoyl Hydrolyzed Collagen; Sodium Cocoyl Hydrolyzed Keratin; Sodium Cocoyl Hydrolyzed Rice Protein; Sodium Cocoyl Hydrolyzed Soy Protein; Sodium Cocoyl Hydrolyzed Wheat Protein; Sodium Cocoyl Sarcosinate; Sodium Cornamphopropionate; Sodium Dicarboxyethylcoco Phosphoethyl Imidazoline; Sodium Diethylaminopropyl Cocoaspartamide; Sodium Dimethicone Copolyol Acetyl Methyltaurate; Sodium Glutamate; Sodium Hydrolyzed Casein; Sodium Hydroxymethylglycinate; Sodium Isostearoamphoacetate; Sodium Isostearoamphopropionate; Sodium Lauraminopropionate; Sodium Lauraminodipropionate; Sodium Lauroamphoacetate; Sodium Lauroamphohydroxypropylsulfonate; Sodium Lauroampho PG-Acetate Phosphate; Sodium Lauroamphopropionate; Sodium Lauroyl Aspartate; Sodium Lauroyl Collagen Amino Acids; Sodium Lauroyl Glutamate; Sodium Lauroyl Hydrolyzed Collagen; Sodium Lauroyl Hydrolyzed Silk; Sodium Lauroyl Oat Amino Acids; Sodium Lauroyl Sarcosinate; Sodium Lauroyl Silk Amino Acids; Sodium Lauroyl Wheat Amino Acids; Sodium Milkamidopropyl PG-Dimonium Chloride Phosphate; Sodium Myristoamphoacetate; Sodium Myristoyl Hydrolyzed Collagen; Sodium Myristoyl Isethionate; Sodium Myristoyl Sarcosinate; Sodium Oleoamphoacetate; Sodium Oleoamphohydroxypropylsulfonate; Sodium Oleoamphopropionate; Sodium Oleoyl Hydrolyzed Collagen; Sodium Oleoyl Isethionate; Sodium Palmitoyl Chondroitin Sulfate; Sodium Palmitoyl Hydrolyzed Collagen; Sodium Palmitoyl Hydrolyzed Wheat Protein; Sodium Pantothenate; Sodium PCA; Sodium PG-Propyl Thiosulfate Dimethicone; Sodium Polyaspartate; Sodium Polyglutamate; Sodium Ricinoleoamphoacetate; Sodium Soy Hydrolyzed Collagen; Sodium Stearoamphoacetate; Sodium Stearoamphohydroxypropylsulfonate; Sodium Stearoamphopropionate; Sodium Stearoyl Casein; Sodium Stearoyl Chondroitin Sulfate; Sodium Stearoyl Glutamate; Sodium Stearoyl Hyaluronate; Sodium Stearoyl Hydrolyzed Collagen; Sodium Stearoyl Hydrolyzed Corn Protein; Sodium Stearoyl Hydrolyzed Silk; Sodium Stearoyl Hydrolyzed Soy Protein; Sodium Stearoyl Hydrolyzed Wheat Protein; Sodium Stearoyl Lactalbumin; Sodium Stearoyl Oat Protein; Sodium Stearoyl Pea Protein; Sodium Stearoyl Soy Protein; Sodium Tallamphopropionate; Sodium Tallowamphoacetate; Sodium/TEA-Lauroyl Collagen Amino Acids; Sodium/TEA-Lauroyl Hydrolyzed Collagen; Sodium/TEA-Lauroyl Hydrolyzed Keratin; Sodium/TEA-Lauroyl Keratin Amino Acids; Sodium/TEA-Undecylenoyl Alginate; Sodium/TEA-Undecylenoyl Carrageenan; Sodium/TEA-Undecylenoyl Collagen Amino Acids; Sodium/TEA-Undecylenoyl Hydrolyzed Collagen; Sodium/TEA-Undecylenoyl Hydrolyzed Corn Protein; Sodium/TEA-Undecylenoyl Hydrolyzed Soy Protein; Sodium/TEA-Undecylenoyl Hydrolyzed Wheat Protein; Sodium Undecylenoamphoacetate; Sodium Undecylenoamphopropionate; Sodium Wheat Germamphoacetate; Soluble Collagen; Soluble Proteoglycan; Soyamidoethyldimonium/Trimonium Hydroxypropyl Hydrolyzed Wheat Protein; Soyamidopropyl Betaine; Soybean (Glycine Soja) Oil Unsaponifiables; Soybean (Glycine Soja) Protein; Soybean Lipid; Soy Dihydroxypropyldimonium Glucoside; Soydimonium Hydroxypropyl Hydrolyzed Wheat Protein; Soyethyldimonium Ethosulfate; Soy Hydroxyethyl Imidazoline; Soytrimonium Chloride; Squalane; Squalene; Stearalkonium Dimethicone Copolyol Phthalate; Stearamidoethyl Diethylamine; Stearamidoethyl Diethylamine Phosphate; Stearamidopropylamine Oxide; Stearamidopropyl Betaine; Stearamidopropyl Dimethylamine; Stearamidopropyl Dimethylamine Lactate; Stearamidopropyl Dimethylamine Stearate; Stearamidopropyl Ethyldimonium Ethosulfate; Stearamidopropyl PG-Dimonium Chloride Phosphate; Stearamidopropyl Pyrrolidonylmethyl Dimonium Chloride; Stearamidopropyl Trimonium Methosulfate; Stearamine Oxide; Steardimonium Hydroxypropyl Hydrolyzed Casein; Steardimonium Hydroxypropyl Hydrolyzed Collagen; Steardimonium Hydroxypropyl Hydrolyzed Keratin; Steardimonium Hydroxypropyl Hydrolyzed Rice Protein; Steardimonium Hydroxypropyl Hydrolyzed Silk; Steardimonium Hydroxypropyl Hydrolyzed Vegetable Protein; Steardimonium Hydroxypropyl Hydrolyzed Wheat Protein; Stearoyl Glutamic Acid; Stearoyl Leucine; Stearoyl PG-Trimonium Chloride; Stearoyl Sarcosine; Steartrimonium Bromide; Steartrimonium Chloride; Steartrimonium Hydroxyethyl Hydrolyzed Collagen; Steartrimonium Methosulfate; Steartrimonium Saccharinate; Stearyl/Aminopropyl Methicone Copolymer; Stearyl Betaine; Stearyl Hydroxyethyl Imidazoline; Stearyl Hydroxyethyl-imidonium Chloride; Stearyl Octyldimonium Chloride; Stearyl Octyldimonium Methosulfate; Stearyl PG-Dimonium Chloride Phosphate; Sulfur; Sulfurized Hydrolyzed Corn Protein; Sulfurized TEA-Ricinoleate; Sunflower (Helianthus Annuus) Seed Oil Unsaponifiables; Sweet Almond (Prunus Amygdalus; Dulcis) Protein; Tall Oil Benzyl Hydroxyethyl Imidazolinium Chloride; Tall Oil Hydroxyethyl Imidazoline; Tallowamidopropylamine Oxide; Tallowamidopropyl Betaine; Tallowamidopropyl Hydroxysultaine; Tallowamine Oxide; Tallow Betaine; Tallow Dihydroxyethyl Betaine; Tallow Hydroxyethyl Imidazoline; Tallowtrimonium Chloride; TEA-Abietoyl Hydrolyzed Collagen; TEA-Cocoyl Glutamate; TEA-Cocoyl Hydrolyzed Collagen; TEA-Cocoyl Hydrolyzed Soy Protein; TEA-Cocoyl Sarcosinate; TEA-Hydrogenated Tallowoyl Glutamate; TEA-Isostearoyl Hydrolyzed Collagen; TEA-Lauraminopropionate; TEA-Lauroyl Collagen Amino Acids; TEA-Lauroyl Glutamate; TEA-Lauroyl Hydrolyzed Collagen; TEA-Lauroyl Keratin Amino Acids; TEA-Lauroyl Sarcosinate; TEA-Myristaminopropionate; TEA-Myristoyl Hydrolyzed Collagen; TEA-Oleoyl Hydrolyzed Collagen; TEA-Oleoyl Sarcosinate; TEA-Palm Kernel Sarcosinate; TEA-Undecylenoyl Hydrolyzed Collagen; Tetrabutoxypropyl Trisiloxane; Thenoyl Methionate; Thiodiglycolamide; Threonine; Tricetylmonium Chloride; Triethonium Hydrolyzed Collagen Ethosulfate; Trimethylsilyamodimethicone; Trioctanoin; TriPABA Panthenol; Trisodium Lauroampho PG-Acetate Chloride Phosphate; Triundecanoin; Tryptophan; Tyrosine; Undecylenamide DEA; Undecylenamide MEA; Undecylenamidopropylamine Oxide; Undecylenamidopropyl Betaine; Undecylenamidopropyltrimonium Methosulfate; Undecylenoyl Hydrolyzed Collagen; Undecylenoyl Wheat Amino Acids; Undecylenoyl Xanthan Gum; Valine; Vegetable Oil; Wheat Amino Acids; Wheat Germamidopropalkonium Chloride; Wheat Germamidopropylamine Oxide; Wheat Germamidopropyl Betaine; Wheatgermamidopropyl Dimethylamine Hydrolyzed Collagen; Wheatgermamidopropyl Dimethylamine Hydrolyzed Wheat Protein; Wheat Germamidopropyldimonium Hydroxypropyl Hydrolyzed Wheat Protein; Wheat Germamidopropyl Epoxypropyldimonium Chloride; Wheatgernamidopropyl Ethyldimonium Ethosulfate; Wheat (Triticum Vulgare) Germ Oil Unsaponifiables; Wheat (Triticum Vulgare) Germ Protein; Wheat (Triticum Vulgare) Gluten; Wheat (Triticum Vulgare) Protein; Whey Protein; Yogurt; Zein; Zinc Hydrolyzed Collagen.

Antistatic agents can sometimes also be used as hair conditioning agents. Antistatic agents are agents reduce static electricity by neutralizing electrical charge on a surface. Antistatic agents include: acetamide MEA; acetamidoethoxybutyl trimonium chloride; acetamidopropyl trimonium chloride; acetum; acetylated lanolin; acetylated lanolin alcohol; acetylated lanolin ricinoleate; acetylmethionyl methylsilanol elastinate; acrylamide/sodium acrylate copolymer; acrylamides copolymer; acrylates/ammonium methacrylate copolymer acrylates/pvp copolymer; acrylates copolymer; adipic acid/dimethylaminohydroxypropyl diethylenetriamine copolymer; adipic acid/epoxypropyl diethylenetriamine copolymer; alanine; allantoin acetyl methionine; almondamidopropalkonium chloride; almondamidopropyl dimethylamine; aluminum capryloyl hydrolyzed collagen; aluminum undecylenoyl collagen amino acids; aminoethylacrylate phosphate/acrylates copolymer aminopropyl laurylglutamine; ammonium acrylates copolymer; ammonium caseinate; ammonium hydrolyzed collagen; ammonium lauroyl sarcosinate; ammonium VA/acrylates copolymer; amodimethicone; amodimethicone/dimethicone copolyol; amp-isostearoyl hydrolyzed collagen; apricotamidopropyl ethyldimonium ethosulfate; arginine; asparagine; aspartic acid; avocadamidopropalkonium chloride; avocadamidopropyl dimethylamine; babassuamidopropalkonium chloride; babassuamidopropyl dimethylamine; behenalkonium chloride; behenamidopropyl dimethylamine; behenamidopropyl dimethylamine behenate; behenamidopropyl dimethylamine lactate; behenamidopropyl ethyldimonium ethosulfate; behenamidopropyl PG-dimonium chloride; behenoyl PG-trimonium chloride; behentrimonium methosulfate; behenyl betaine; behenyl hydroxyethyl imidazoline; benzyl nicotinate; benzyl triethyl ammonium chloride; benzyltrimonium hydrolyzed collagen; betaine; bishydroxyethyl dihydroxypropyl stearaminium chloride; butyl ester of ethylene/MA copolymer butyl ester of PVM/MA copolymer; C12–15 alkyl salicylate; C12–16 alcohols; C14–20 isoalkylamidopropylethyldimonium ethosulfate; C18–22 isoalkylamidopropylethyldimonium ethosulfate; calcium pantothenate; calcium pantothenate; canolamidopropyl ethyldimonium ethosulfate; capramide DEA; capryl hydroxyethyl imidazoline; capryloyl collagen amino acids; capryloyl hydrolyzed collagen; capryloyl hydrolyzed keratin; capryloyl keratin amino acids; caprylyl hydroxyethyl imidazoline; carpronium chloride; casein; ceresin; cetethyl morpholinium ethosulfate; cetethyldimonium bromide; cetrimonium methosulfate; cetrimonium saccharinate; cetrimonium tosylate; cetyl betaine; cetyl pyrrolidonylmethyl dimonium chloride; cetylpyridinium chloride; cholecalciferol polypeptide; cocamidopropyl dimethylamine; cocamidopropyl dimethylamine hydrolyzed collagen; cocamidopropyl dimethylamine propionate; cocamidopropyl dimethylaminohydroxypropyl hydrolyzed collagen; cocamidopropyl dimethylammonium C8–16 isoalkylsuccinyl lactoglobulin sulfonate; cocamidopropyl ethyldimonium ethosulfate; cocamidopropyl morpholine; cocamidopropyl morpholine lactate; cocamidopropyl PG-dimonium chloride; cocamidopropyl PG-dimonium chloride phosphate; cocamidopropyldimonium hydroxypropyl hydrolyzed collagen; cocamidopropyltrimonium chloride; cocamine oxide; coco/oleamidopropyl betaine coco-ethyldimonium ethosulfate; coco-hydroxysultaine; coco-morpholine oxide; cocoalkonium chloride; cocodimonium hydroxypropyl hydrolyzed casein; cocodimonium hydroxypropyl hydrolyzed collagen; cocodimonium hydroxypropyl hydrolyzed hair keratin; cocodimonium hydroxypropyl hydrolyzed keratin; cocodimonium hydroxypropyl hydrolyzed rice protein; cocodimonium hydroxypropyl hydrolyzed silk; cocodimonium hydroxypropyl hydrolyzed soy protein; cocodimonium hydroxypropyl hydrolyzed wheat protein; cocodimonium hydroxypropyl silk amino acids; cocotrimonium chloride; cocoyl benzyl hydroxyethyl imidazolinium chloride; cocoyl hydrolyzed collagen; cocoyl hydrolyzed keratin; cocoyl hydrolyzed soy protein; cocoyl polyglyceryl-4 hydroxypropyl dihydroxyethylamine; corn starch/acrylamide/sodium acrylate copolymer; cyclomethicone; cysteine; cystine; DEA-lauraminopropionate; DEA-linoleate; decyl betaine; decylamine oxide; dibehenyl/diarachidyl dimonium chloride; dibehenyl methylamine; dibehenyldimonium chloride; dibehenyldimonium methosulfate; dicapryl/dicaprylyl dimonium chloride dicaproyl cystine; dicetyldimonium chloride; dicocodimonium chloride; dicocoylethyl hydroxyethylmonium methosulfate; didecyldimonium chloride; diethyl aspartate; diethyl glutamate; diethylaminoethyl PEG-5 laurate; diethylene tricaseinamide; dihydrogenated tallow benzylmonium chloride; dihydrogenated tallow benzylmonium hectorite; dihydrogenated tallow hydroxyethylmonium methosulfate; dihydrogenated tallowamidoethyl hydroxyethylmonium chloride; dihydrogenated tallowamidoethyl hydroxyethylmonium methosulfate; dihydrogenated tallowdimonium chloride; dihydrogenated tallowethyl hydroxyethylmonium methosulfate; dihydrogenated tallowoylethyl hydroxycthylmonium methosulfate; dihydroxyethyl C12–15 alkoxypropylamine oxide; dihydroxyethyl cocamine oxide; dihydroxyethyl soya glycinate; dihydroxyethyl stearamine oxide; dihydroxyethyl stearyl glycinate; dihydroxyethyl tallowamine oxide; dilaureth-4 dimonium chloride; dilauryl acetyl dimonium chloride; dilauryldimonium chloride; dilinoleamidopropyl dimethylamine; dimethicone copolyol; dimethicone propyl PG-betaine; dimethyl aspartic acid; dimethyl behenamine; dimethyl cystinate; dimethyl glutamic acid; dimethyl glutarate; dimethyl lauramine; dimethyl lauramine oleate; dimethyl myristamine; dimethyl palmitamine; dimethyl soyamine; dimethyl stearamine; dioctylamine; dioctyldodecyl dodecanedioate; dioleoyl edthp-monium methosulfate; dioleyl edthp-monium methosulfate; dipalmitoyl cystine; dipalmitoyl hydroxyproline; dipalmitoylethyl hydroxyethylmonium methosulfate; dipalmoylethyl hydroxyethylmonium methosulfate; disodium caproamphodiacetate; disodium capryloamphodiacetate; disodium hydrogenated cottonseed glyceride sulfosuccinate; disodium lauriminodipropionaite; disodium lauroamphodiacetate; disodium lauroamphodipropionate; disodium oleamido MIPA-sulfosuccinate; disodium steariminodipropionate; disodium stearoamphodiacetate; disoyadimonium chloride; disteareth-6 dimonium chloride; distearoylethyl hydroxyethylmonium methosulfate; distearyldimonium chloride; ditallowamidoethyl hydroxypropylmonium methosulfate; ditallowdimonium chloride; ditallowethyl hydroxyethylmonium methosulfate; ditallowoylethyl hydroxyethylmonium methosulfate; ditridecyldimonium chloride; docosahexaenoic acid; dodecylbenzyltrimonium chloride; dodecylxylyldimonium chloride; erucalkonium chloride; erucamidopropyl hydroxysultaine; ethyl aspartate; ethyl ester of hydrolyzed animal protein; ethyl ester of hydrolyzed keratin; ethyl ester of hydrolyzed silk; ethyl ester of PVM/MA copolymer; ethyl glutamate; ethyl hydroxymethyl oleyl oxazoline; ethyl PEG-15 cocamine sulfate; ethyl serinate; gelatin/keratin amino acids/lysine hydroxypropyl trimonium chloride; gelatin/lysine/polyacrylamide hydroxypropyltrimonium chloride; ginseng hydroxypropyltrimonium chloride; glucosamine HCl; glutamic acid; glutamic acid; glutamine; glyceryl distearate; glyceryl lanolate; glycine; glycol oleate; glycol ricinoleate; guar hydroxypropyltrimonium chloride; hair keratin amino acids; hexadimethrine chloride; hexyl nicotinate; hinokitiol; histidine; hyaluronic acid; hydrogenated lanolin; hydrogenated tallowalkonium chloride; hydrogenated tallowamine oxide; hydrogenated tallowtrimonium chloride; hydrolyzed albumen; hydrolyzed casein; hydrolyzed collagen; hydrolyzed corn protein; hydrolyzed elastin; hydrolyzed hair keratin; hydrolyzed human placental protein; hydrolyzed keratin; hydrolyzed lupine protein; hydrolyzed milk protein; hydrolyzed oat protein; hydrolyzed oats; hydrolyzed pea protein; hydrolyzed placental protein; hydrolyzed potato protein; hydrolyzed rice bran protein; hydrolyzed rice protein; hydrolyzed serum protein; hydrolyzed silk; hydrolyzed soy protein; hydrolyzed spinal protein; hydrolyzed sweet almond protein; hydrolyzed vegetable protein; hydrolyzed wheat protein; hydrolyzed yeast protein; hydrolyzed zein; hydroxycetyl hydroxyethyl dimonium chloride; hydroxyethyl cetyldimonium chloride; hydroxyethyl cetyldimonium phosphate; hydroxyethyl stearamide-mipa; hydroxylated lanolin; hydroxyproline; hydroxypropyl biscetearyldimonium chloride; hydroxypropyl bisisostearamidopropyldimonium chloride; hydroxypropyl bisoleyldimonium chloride; hydroxypropyl bisstearyldimonium chloride; hydroxypropyl guar; hydroxypropyl guar hydroxypropyltrimonium chloride; hydroxypropyltrimonium amylopectin/glycerin crosspolymer; hydroxypropyltrimonium gelatin; hydroxypropyltrimonium hydrolyzed casein; hydroxypropyltrimonium hydrolyzed collagen; hydroxypropyltrimonium hydrolyzed keratin; hydroxypropyltrimonium hydrolyzed rice bran protein; hydroxypropyltrimonium hydrolyzed silk; hydroxypropyltrimonium hydrolyzed soy protein; hydroxypropyltrimonium hydrolyzed vegetable protein; hydroxypropyltrimonium hydrolyzed wheat protein; hydroxystearamide MEA; hydroxystearamidopropyl trimonium chloride; hydroxystearamidopropyl trimonium methosulfate; hydroxystearyl methylglucamine; inositol; isobutylated lanolin oil; isodecyl isononanoate; isodecyl salicylate; isoleucine; isononamidopropyl ethyldimonium ethosulfate; isononyl isononanoate; isopropyl ester of PVM/MA copolymer; isopropyl lanolate; isopropyl palmitate; isostearamide DEA; isostearamide MEA; isostearamide MIPA; isostearamidopropyl betaine; isostearamidopropyl dimethylamine; isostearamidopropyl dimethylamine gluconate; isostearamidopropyl dimethylamine glycolate; isostearamidopropyl dimethylamine lactate; isostearamidopropyl epoxypropyl dimonium chloride; isostearamidopropyl ethyldimonium ethosulfate; isostearamidopropyl ethylmorpholinium ethosulfate; isostearamidopropyl laurylacetodimonium chloride; isostearamidopropyl morpholine; isostearamidopropyl morpholine lactate; isostearamidopropyl PG-dimonium chloride; isostearaminopropalkonium chloride; isostearoyl hydrolyzed collagen; isostearoyl PG-trimonium chloride; isostearyl benzylimidonium chloride; isostearyl diglyceryl succinate; isostearyl ethyldimonium chloride; isostearyl ethylimidonium ethosulfate; isostearyl hydroxyethyl imidazoline; keratin amino acids; lactamide MEA; lactamidopropyl trimonium chloride; lactoglobulin; lactoyl methylsilanol elastinate; lanolin; lanolin alcohol; lanolin cera; lanolin linoleate; lanolin ricinoleate; lanosterol; lapyrium chloride; lauramide DEA; lauramide MEA; lauramide MIPA; lauramidopropyl acetamidodimonium chloride; lauramidopropyl betaine; lauramidopropyl dimethylamine; lauramidopropyl dimethylamine propionate; lauramidopropyl PG-dimonium chloride; lauramidopropylamine oxide; lauramine; lauramine oxide; lauraminopropionic acid; laurdimonium hydroxypropyl hydrolyzed soy protein; laurdimonium hydroxypropyl hydrolyzed wheat protein; lauroyl collagen amino acids; lauroyl hydrolyzed collagen; lauroyl PG-trimonium chloride; lauroyl sarcosine; laurtrimonium bromide; laurtrimonium trichlorophenoxide; lauryl aminopropylglycine; lauryl betaine; lauryl diethylenediaminoglycine; lauryl dimethylamine cyclocarboxypropyloleate; lauryl glycol; lauryl hydroxyethyl imidazoline; lauryl isoquinolinium bromide; lauryl isoquinolinium saccharinate; lauryl methyl gluceth-10 hydroxypropyldimonium chloride; lauryl myristate; lauryl palmitate; lauryl sultaine; lauryldimonium hydroxypropyl hydrolyzed casein; lauryldimonium hydroxypropyl hydrolyzed collagen; lauryldimonium hydroxypropyl hydrolyzed keratin; lauryldimonium hydroxypropyl hydrolyzed silk; lauryldimonium hydroxypropyl hydrolyzed soy protein; lauryldimonium hydroxypropyl hydrolyzed wheat protein; laurylpyridinium chloride; lecithin; lecithinamide DEA; leucine; linoleamide; linoleamide DEA; linoleamide MEA; linoleamide MIPA; linoleamidopropalkonium chloride; linoleamidopropyl dimethylamine; linoleamidopropyl dimethylamine dimer dilinoleate; linoleamidopropyl dimethylamine lactate; linoleamidopropyl ethyldimonium ethosulfate; linoleamidopropyl PG-dimonium chloride phosphate; linoleic acid; linolenic acid; lysine; lysine; lysine PCA; methacryloyl ethyl betaine/ acrylates copolymer; methenammonium chloride; methicone; methionine; methyl aspartic acid; methyl glutamic acid; methyl hydroxycetyl glucaminium lactate; methyl hydroxymethyl oleyl oxazoline; methylbenzethonium chloride; methylenebis tallow acetamidodimonium chloride; methylsilanol acetylmethionate; methylsilanol acetyltyrosine; methylsilanol elastinate; methylsilanol hydroxyproline; methylsilanol hydroxyproline aspartate; methylsilanol mannuronate; milk amino acids; minkamidopropalkonium chloride; minkamidopropyl dimethylamine; minkamidopropyl ethyldimonium ethosulfate; monosaccharide lactate condensate; montan acid wax; montan cera; myristamide DEA; myristamide MEA; myristamide MIPA; myristamidopropyl betaine; myristamidopropyl dimethylamine; myristamidopropylamine oxide; myristamine oxide; myristaminopropionic acid; myristoyl hydrolyzed collagen; myristoyl sarcosine; myristyl betaine; myristyl hydroxyethyl imidazoline; niacin; norvaline; norvaline; norvaline; octylacrylamide/ acrylates/butylaminoethyl methacrylate copolymer; octyldecyl trimonium chloride; octyldodecyltrimonium chloride; oleamide DEA; oleamide MEA; oleamide MIPA; oleamidopropyl betaine; oleamidopropyl dimethylamine; oleamidopropyl dimethylamine glycolate; oleamidopropyl dimethylamine hydrolyzed collagen; oleamidopropyl dimethylamine lactate; oleamidopropyl dimethylamine propionate; oleamidopropyl ethyldimonium ethosulfate; oleamidopropyl hydroxysultaine; oleamidopropyl PG-dimonium chloride; oleamidopropylamine oxide; oleamidopropyldimonium hydroxypropyl hydrolyzed collagen; oleamine; oleamine bishydroxypropyltrimonium chloride; oleamine oxide; oleoyl hydrolyzed collagen; oleoyl PG-trimonium chloride; oleoyl sarcosine; oleyl betaine; oleyl hydroxyethyl imidazoline; oleyl lanolate; olivamidopropyl dimethylamine; olivamidopropyl dimethylamine lactate; oryzanol; ouricury wax; palm kernclamidopropyl betaine; palmamidopropyl betaine; palmitamide DEA; palmitamide MEA; palmitamidopropyl betaine; palmitamidopropyl diethylamine; palmitamidopropyl dimethylamine; palmitamidopropyl dimethylamine lactate; palmitamidopropyl dimethylamine propionate; palmitamidopropylamine oxide; palmitamine; palmitamine oxide; palmitoleamidopropyl dimethylamine lactate; palmitoleamidopropyl dimethylamine propionate; palmitoyl collagen amino acids; palmitoyl hydrolyzed collagen; palmitoyl hydrolyzed milk protein; palmitoyl keratin amino acids; palmitoyl PG-trimonium chloride; panthenol; panthenyl ethyl ether; panthenyl ethyl ether acetate; panthenyl hydroxypropyl steardimonium chloride; panthenyl triacetate; pantothenic acid; pantothenic acid polypeptide; paraffinum liquidum; PCA ethyl cocoyl arginate; PEG-10 coco-benzonium chloride; PEG-10 coconut oil esters; PEG-10 stearamine; PEG-10 stearyl benzonium chloride; PEG-105 behenyl propylenediamine; PEG-15 cocomonium chloride; PEG-15 cocopolyamine; PEG-15 oleammonium chloride; PEG-15 stearamine; PEG-15 stearmonium chloride; PEG-15 tallow polyamine; PEG-2 coco-benzonium chloride; PEG-2 cocomonium chloride; PEG-2 milk solids; PEG-2 oleammonium chloride; PEG-2 stearamine; PEG-2 stearmonium chloride; PEG-20 tallow ammonium ethosulfate; PEG-25 diethylmonium chloride; PEG-3 lauramine oxide; PEG-3 tallow propylenedimonium dimethosulfate; PEG-5 cocomonium methosulfate; PEG-5 ditridecylmonium chloride; PEG-5 stearamine; PEG-5 stearyl ammonium chloride; PEG-5 stearyl ammonium lactate; PEG-5 tall oil sterol ether; PEG-5 tallow benzonium chloride; PEG-50 stearamine; PEG-8 palmitoyl methyl diethonium methosulfate; petrolatum; PG-hydroxyethylcellulose cocodimonium chloride; PG-hydroxyethylcellulose lauryldimonium chloride; PG-hydroxyethylcellulose stearyldimonium chloride; phenyl trimethicone; phenylalanine; phenylalanine; phosphatidylcholine; phthalic anhydride/glycerin/glycidyl decanoate copolymer pix ex carbone; polyacrylamide; polybutylene terephthalate; polyethylacrylate; polyethylene; polymethacrylamidopropyltrimonium chloride; polyquaternium-1; polyquaternium-10; polyquaternium-11; polyquaternium-12; polyquaternium-13; polyquaternium-14; polyquaternium-15; polyquaternium-16; polyquaternium-17; polyquaternium-18; polyquaternium-19; polyquaternium-2; polyquaternium-20; polyquaternium-22;

polyquaternium-24; polyquaternium-27; polyquaternium-28; polyquaternium-29; polyquaternium-30; polyquaternium-31; polyquaternium-32; polyquaternium-33; polyquaternium-34; polyquaternium-35; polyquaternium-36; polyquaternium-37; polyquaternium-39; polyquaternium-4; polyquaternium-42; polyquaternium-5; polyquaternium-6; polyquaternium-7; polyquaternium-8; polyquaternium-9; polysilicone-7; polyvinyl acetate; polyvinyl butyral; polyvinyl imidazolinium acetate; polyvinyl methyl ether; potassium caseinate; potassium cocoyl hydrolyzed casein; potassium cocoyl hydrolyzed collagen; potassium cocoyl hydrolyzed keratin; potassium cocoyl hydrolyzed rice bran protein; potassium cocoyl hydrolyzed rice protein; potassium cocoyl hydrolyzed silk; potassium cocoyl hydrolyzed soy protein; potassium cocoyl hydrolyzed wheat protein; potassium lauroyl collagen amino acids; potassium lauroyl hydrolyzed collagen; potassium lauroyl hydrolyzed soy protein; potassium lauroyl wheat amino acids; potassium lauryl hydroxypropyl sulfonate; potassium myristoyl hydrolyzed collagen; potassium oleoyl hydrolyzed collagen; potassium stearoyl hydrolyzed collagen; potassium tallate; potassium undecylenoyl hydrolyzed collagen; PPG-12-buteth-16; PPG-14 butyl ether; PPG-15 butyl ether; PPG-15-buteth-20; PPG-16 butyl ether; PPG-18 butyl ether; PPG-2-buteth-3; PPG-20 methyl glucose ether; PPG-20-buteth-30; PPG-22 butyl ether; PPG-24-buteth-27; PPG-25 diethylmonium chloride; PPG-26-buteth-26; PPG-28-buteth-35; PPG-3 tallow aminopropylamine; PPG-3-buteth-5; PPG-30 butyl ether; PPG-33 butyl ether; PPG-33-buteth-45; PPG-4 butyl ether; PPG-40 butyl ether; PPG-40 diethylmonium chloride; PPG-5 butyl ether; PPG-5-buteth-7; PPG-53 butyl ether; PPG-7-buteth-10; PPG-9 butyl ether; PPG-9 diethylmonium chloride; PPG-9-buteth-12; proline; proline; propyltrimonium hydrolyzed collagen; propyltrimonium hydrolyzed soy protein; propyltrimonium hydrolyzed wheat protein; PVM/MA copolymer; PVP/dimethylaminoethylmethacrylate copolymer; PVP/eicosene copolymer; PVP/hexadecene copolymer; PVP/VA/itaconic acid copolymer; PVP/VA/vinyl propionate copolymer; PVP/va copolymer; pyridoxine; pyridoxine dicaprylate; pyridoxine dilaurate; pyridoxine dioctenoate; pyridoxine dipalmitate; pyridoxine HCl; pyridoxine tripalmitate; quaternium-1; quaternium-14; quaternium-16; quaternium-18; quaternium-18 methosulfate; quaternium-22; quaternium-24; quaternium-26; quaternium-27; quaternium-30; quaternium-33; quaternium-43; quaternium-45; quaternium-51; quaternium-52; quaternium-53; quaternium-56; quaternium-60; quaternium-61; quaternium-62; quaternium-63; quaternium-70; quaternium-71; quaternium-72; quaternium-73; quaternium-75; quaternium-76 hydrolyzed collagen; quaternium-77; quaternium-78; quaternium-79 hydrolyzed collagen; quaternium-79 hydrolyzed keratin; quaternium-79 hydrolyzed milk protein; quaternium-79 hydrolyzed silk; quaternium-79 hydrolyzed soy protein; quaternium-79 hydrolyzed wheat protein; quaternium-8; quaternium-80; quaternium-81; quaternium-82; quaternium-83; quaternium-84; quaternium-85; rapeseedamidopropyl benzyldimonium chloride; rapeseedamidopropyl epoxypropyl dimonium chloride; rapeseedamidopropyl ethyldimonium ethosulfate; resorcinol acetate; ricinoleamide DEA; ricinoleamide MEA; ricinoleamide MIPA; ricinoleamidopropyl betaine; ricinoleamidopropyl dimethylamine; ricinoleamidopropyl dimethylamine lactate; ricinoleamidopropyl ethyldimonium ethosulfate; ricinoleamidopropyltrimonium chloride; ricinoleamidopropyltrimonium methosulfate; saffloweramidopropyl ethyldimonium ethosulfate; serica; sericin; serine; silicone quaternium-1; silicone quaternium-2; silicone quaternium-3; silicone quaternium-4; silicone quaternium-5; silicone quaternium-6; silicone quaternium-7; silicone quaternium-8; silicone quaternium-9; sine adipe lac; sodium/TEA-lauroyl collagen amino acids; sodium/TEA-lauroyl hydrolyzed collagen; sodium/TEA-lauroyl hydrolyzed keratin; sodium/TEA-lauroyl keratin amino acids; sodium/TEA-undecylenoyl collagen amino acids; sodium/TEA-undecylenoyl hydrolyzed collagen; sodium acrylate/vinyl alcohol copolymer; sodium carrageenan; sodium caseinate; sodium chondroitin sulfate; sodium cocoyl collagen amino acids; sodium cocoyl hydrolyzed collagen; sodium cocoyl hydrolyzed keratin; sodium cocoyl hydrolyzed rice protein; sodium cocoyl hydrolyzed soy protein; sodium isethionate; sodium lauraminopropionate; sodium lauriminodipropionate; sodium lauroamphohydroxypropylsulfonate; sodium lauroamphopropionate; sodium lauroyl collagen amino acids; sodium lauroyl glutamate; sodium lauroyl hydrolyzed collagen; sodium lauroyl hydrolyzed silk; sodium lauroyl isethionate; sodium lauroyl sarcosinate; sodium lauroyl taurate; sodium lauroyl wheat amino acids; sodium methyl oleoyl taurate; sodium myristoamphoacetate; sodium myristoyl hydrolyzed collagen; sodium myristoyl isethionate; sodium myristoyl sarcosinate; sodium oleoamphoacetate; sodium oleoamphopropionate; sodium oleoyl hydrolyzed collagen; sodium oleoyl isethionate; sodium PCA; sodium PCA; sodium soya hydrolyzed collagen; sodium stearoamphoacetate; sodium stearoyl hydrolyzed collagen; sodium tallamphopropionate; sodium urocanate; soluble collagen; soy dihydroxypropyldimonium polyglucose; soyaethyl morpholinium ethosulfate; soyamidopropalkonium chloride; soyamidopropyl ethyldimonium ethosulfate; soyamine; soydimonium hydroxypropyl hydrolyzed wheat protein; soyethyldimonium ethosulfate; soytrimonium chloride; squalene; starch diethylaminoethyl ether; steapyrium chloride; stearamide DEA; stearamide MEA; stearamide MEA-stearate; stearamide MIPA; stearamidoethyl diethanolamine; stearamidoethyl diethylamine; stearamidoethyl diethylamine phosphate; stearamidoethyl ethanolamine; stearamidoethyl ethanolamine phosphate; stearamidopropalkonium chloride; stearamidopropyl betaine; stearamidopropyl cetearyl dimonium tosylate; stearamidopropyl dimethylamine; stearamidopropyl dimethylamine lactate; stearamidopropyl ethyldimonium ethosulfate; stearamidopropyl morpholine; stearamidopropyl morpholine lactate; stearamidopropyl PG-dimonium chloride phosphate; stearamidopropyl pyrrolidonylmethyl dimonium chloride; stearamidopropyl trimonium methosulfate; stearamidopropylamine oxide; stearamine; stearamine oxide; steardimonium hydroxypropyl hydrolyzed casein; steardimonium hydroxypropyl hydrolyzed collagen; steardimonium hydroxypropyl hydrolyzed keratin; steardimonium hydroxypropyl hydrolyzed rice protein; steardimonium hydroxypropyl hydrolyzed silk; steardimonium hydroxypropyl hydrolyzed vegetable protein; steardimonium hydroxypropyl hydrolyzed wheat protein; stearoyl PG-trimonium chloride; stearoyl sarcosine; steartrimonium hydroxyethyl hydrolyzed collagen; steartrimonium methosulfate; stearyl betaine; stearyl hydroxyethyl imidazoline; stearyl hydroxyethylimidonium chloride; stearyl octyldimonium chloride; stearyl octyldimonium methosulfate; stearylvinyl ether/MA copolymer; sucrose cocoate; sulfur; synthetic wax; tall oil benzyl hydroxyethyl imidazolinium chloride; tall oil hydroxyethyl imidazoline; tallamide DEA; tallow trihydroxyethylammonium acetate; tallowalkonium chloride; tallowamide DEA; tallowamide MEA; tallowamidopropylamine oxide; tallowamine oxide; tallowdimonium propyltrimonium dichloride; tallowtrimonium chloride;

TEA-abietoyl hydrolyzed collagen; TEA-cocoyl hydrolyzed collagen; TEA-cocoyl hydrolyzed soy protein; TEA-lauraminopropionate; TEA-lauroyl keratin amino acids; TEA-lauroyl sarcosinate; TEA-myristaminopropionate; TEA-myristoyl hydrolyzed collagen; TEA-oleoyl hydrolyzed collagen; TEA-oleoyl sarcosinate; TEA-palm kernel sarcosinate; TEA-undecylenoyl hydrolyzed collagen; tetrabutyl ammonium bromide; thenoyl methionate; threonine; threonine; tricetylmonium chloride; tridecyl salicylate; triethonium hydrolyzed collagen ethosulfate; trilaurylamine; trimethylsilylamodimethicone; trioctanoin; tripaba panthenol; trisodium lauroampho PG-acetate phosphate chloride; tristearyl PG-phosphate dimonium chloride; triundecanoin; tryptophan; tryptophan; tyrosine; undecylenamide DEA; undecylenamide MEA; undecylenamidopropyltrimonium methosulfate; undecylenoyl collagen amino acids; undecylenoyl hydrolyzed collagen; undecylenyl alcohol; urea; VA/crotonates/vinyl neodecanoate copolymer; va/crotonates copolymer; valine; wheat germamidopropalkonium chloride; wheat germamidopropyl epoxypropyldimonium chloride; wheat germamidopropylamine oxide; wheat germamidopropyldimonium hydroxypropyl hydrolyzed wheat protein; wheatgermamidopropyl dimethylamine hydrolyzed collagen; wheatgermamidopropyl dimethylamine hydrolyzed wheat protein; wheatgermamidopropyl ethyldimonium ethosulfate; *zea mays*; zinc hydrolyzed collagen.

In particular, cationic and amphoteric fatty acids such as polyquaternium compounds are useful as hair conditioners or fixatives. Examples of cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, alkyl vinyl pyridinium, and alkyl vinyl pyrrolidine salts. The alkyl portions of these, monomers are preferably lower alkyls such as the C1–C3 alkyls, more preferably C1 and C2 alkyls.

Other compounds useful as bulking agents include: octylacrylamide/acrylates/butylaminoethyl methacrylate copolymer (a polymer of N-tert-octyl acrylamide, methyl methacrylate, hydroxypropyl methacrylate, acrylic acid and t-butyl aminoethyl methacrylate).

Other cationic conditioning compounds include quaternary nitrogen derivatives of cellulose ethers, homopolymers of dimethyldiallyl-ammonium chloride, copolymers of acrylamide and dimethyldiallylammonium chloride, homopolymers or copolymers derived from acrylic acid or methacrylic acid containing cationic nitrogen functional groups attached to the polymer via ester or amide linkages, polycondensation products of N,N'-bis-(2,3-epoxypropyl)-piperazine or of piperazine-bis-acrylamide and piperazine, poly-(dimethylbutenylammonium chloride)-α,θ-bis-(triethanolammonium) chloride.

The agent can also be a hair fixative as described above. Hair fixatives are agents which impart hair-holding or style-retention properties to hair. Film formers, such as gums and polymeric substances, can also be used as hair fixatives. Examples of hair fixative agents including some film formers which are suitable hair fixatives include:

Acrylamide/Ammonium Acrylate Copolymer; Acrylamides/ DMAPA Acrylates/Wethoxy PEG Methacrylate Copolymer; Acrylamidopropyltrimonium Chloride/Acrylamide Copolymer; Acrylamidopropyltrimonium Chloride/ Acrylates Copolymer; Acrylates/Acetoacetoxyethyl Methacrylate Copolymer; Acrylates/Acrylamide Copolymer; Acrylates/Ammonium Methacrylate Copolymer; Acrylates Copolymer; Acrylates/Octylacrylamide Copolymer; Acrylates/PVP Copolymer; Acrylates/VA Copolymer; Adipic Acid/Diethylenetriamine Copolymer; Adipic Acid/Dimethylaminohydroxypropyl Diethylenetriamine Copolymer; Adipic Acid/Epoxypropyl Diethylenetriamine Copolymer; Adipic Acid/Isophthalic Acid/ Neopentyl Glycol/Trimethylolpropane Copolymer; Allyl Stearate/VA Copolymer; Aminoethylacrylate Phosphate/ Acrylates Copolymer; Ammonium VA/Acrylates Copolymer; AMP-Acrylates/Diacetoneacrylamide Copolymer; AMPA-Acrylates/Dimethylaminoethylmethacrylate Copolymer; AMPD-Acrylates/Diacetoneacrylamide Copolymer; Butylated PVP; Butyl Ester of Ethylene/MA Copolymer; Butyl Ester of PVM/MA Copolymer; Calcium/Sodium PVM/MA Copolymer; Corn Starch/ Acrylamide/Sodium Acrylate Copolymer; Diethylene Glycolamine/Epichlorohydrin/Piperazine Copolymer; Ethyl Ester of PVM/MA Copolymer; Isobutylene/MA Copolymer; Isopropyl Ester of PVM/MA Copolymer; Karaya (Sterculia Urens) Gum; Lauryl Methacrylate/ Glycol Dimethacrylate Copolymer; Methacryloyl Ethyl Betaine/Acrylates Copolymer; Octylacrylamide/ Acrylates/Butylaminoethyl Methacrylate Copolymer; PEG-8/SMDI Copolymer; Polyacrylamide; Polybeta-alanine/Glutaric Acid Crosspolymer; Polybutylene Terephthalate; Polyethylacrylate; Polyethylene Terephthalate; Polyperfluoroperhydrophenanthrene; Polyquaternium-1; Polyquaternium-2; Polyquaternium-4; Polyquaternium-5; Polyquaternium-6; Polyquaternium-7; Polyquaternium-8; Polyquaternium-9; Polyquaternium-10; Polyquaternium-11; Polyquaternium-12; Polyquaternium-13; Polyquaternium-14; Polyquaternium-15; Polyquaternium-16; Polyquaternium-17; Polyquaternium-18; Polyquaternium-19; Polyquaternium-20; Polyquaternium-22; Polyquaternium-24; Polyquaternium-27; Polyquaternium-28; Polyquaternium-29; Polyquaternium-30; Polyquaternium-31; Polyquaternium-32; Polyquaternium-33; Polyquaternium-34; Polyquaternium-35; Polyquaternium-36; Polyquaternium-37; Polyquaternium-39; Polyquaternium-45; Polyquaternium-46; Polyquaternium-47; Polysilicone-9; Polyvinyl Acetate; Polyvinyl Butyral; Polyvinylcaprolactam; Polyvinylformamide; Polyvinyl Imidazolinium Acetate; Polyvinyl Methyl Ether; PPG-12/SMDI Copolymer PPG-51/SMDI Copolymer; PVM/MA Copolymer; PVP; PVP/Acrylates/ Lauryl Methacrylate Copolymer; PVP/ Dimethylaminoethylmethacrylate Copolymer; PVP/ DMAPA Acrylates Copolymer; PVP/Hexadecene Copolymer; PVP/VA Copolymer; PVP/VA/Itaconic Acid Copolymer; PVP/VA/Vinyl Propionate Copolymer; PVP/ Vinyl Caprolactam/DMAPA Acrylates Copolymer; Rosin Acrylate; Shellac; Sodium Polyacrylate; Terephthalic Acid/Isophthalic Acid/Sodium Isophthalic Acid Sulfonate/Glycol Copolymer; VA/Crotonates Copolymer; VA/Crotonates/Methacryloxybenzophenone-1 Copolymer; VA/Crotonates/Vinyl Neodecanoate Copolymer; VA/Crotonates/Vinyl Propionate Copolymer; VA/DBM Copolymer; VA/Vinyl Butyl Benzoate/Crotonates Copolymer; Vinyl Caprolactam/PVP/ Dimethylaminoethyl Methacrylate Copolymer; Yeast Palmitate.

Other compounds which are useful as hair fixatives include shellac, polyvinylpyrrolidone-ethyl methacrylate-methacrylic acid tarpolymer, vinyl acetate-crotonic acid copolymer, vinyl acetate-crotonic acid-vinyl neodeconate copolymer, vinyl acetate-crotonic acid-vinyl neodeconate tarpolymer, poly(vinylpyrrolidone-ethylmethacrylate) methacrylic acid copolymer, vinyl methyl ether-maleic anhydride copolymer, octylacrylamide-acrylate-butylaminoethyl-methacrylate copolymer, and poly(vinylpyrrolidone-dimethylaminoethyl-methacrylate) copolymer and derivatives; thioglycollic acid and its salts and esters; potassium or sodium hydroxide; lithium hydroxide; calcium hydroxide; quinine and its salts; resorcinol; 1,3-bis(hydroxymethyl) imidazolidine-2-thione; etidronic acid and its salts (1-hydroxy-ethylidene-diphosphonic acid and its salts).

Examples of anti-foaming agents which are useful as bulking agents include: bisphenylhexamethicone; dimethicone; dimethiconol; hexamethyldisiloxane; hexyl alcohol; isopropyl alcohol; petroleum distillates; phenethyl disiloxane; phenyl trimethicone; polysilicone-7; propyl alcohol; silica dimethyl silylate; silica silylate; tetramethyl decynediol; trimethylsiloxysilicate.

The active agent also can be a tissue sealant. Tissue sealants are those used in wound healing to mechanically seal wounds. The use of transglutaminase to covalently attach such materials would add mechanical and adhesive strength to this sealant. Such tissue sealants are composed typically of fibrinogen, collagen, hyaluronic acid, synthetic peptides and the like. They also can be polyglutamines, polylysines, or polymers of both glutamine and lysine, corneocyte proteins and the like.

The active agents also can be insect repellants. A widely used insect repellant is N-N-diethyl-3-methylbenzamide. Pheromones are also useful as insect repellants.

The agent also may be cultured cells and cultured body tissues used for wound healing, cartilage replacement, corneal replacements and other like surgical procedures.

As mentioned earlier, the agent can also be a film forming agent. A film forming agent is an agent which produces a continuous film on skin, hair or nails upon application. Film forming agents are useful in wound healing or in some cases as hair fixatives, as described above. Examples of film forming agents include: acetyl tributyl citrate; acetyl triethyl citrate; acetyl trioctyl citrate; acrylamide/sodium acrylate copolymer; acrylamides/acrylates/DMAPA/methoxy PEG methacrylate copolymer; acrylamides copolymer; acrylamidopropyltrimonium chloride/acrylates copolymer; acrylates/acetoacetoxyethyl methacrylate copolymer; acrylates/acrylamide copolymer; acrylates/ammonium methacrylate copolymer; acrylates/C10–30 alkyl acrylate crosspolymer; acrylates/diacetoneacrylamide copolymer; acrylates/octylacrylamide copolymer; acrylates/PVP copolymer; acrylates/steareth-50 acrylate copolymer; acrylates/VA copolymer; acrylates/VA crosspolymer; acrylates copolymer; acrylic acid/acrylonitrogens copolymer; adipic acid/diethylene glycol/glycerin crosspolymer; adipic acid/diethylenetriamine copolymer; adipic acid/dimethylaminohydroxypropyl diethylenetriamine copolymer; adipic acid/epoxypropyl diethylenetriamine copolymer; adipic acid/isophthalic acid/neopentyl glycol/trimethylolpropane; copolymer; albumen; allyl stearate/VA copolymer; aminoethylacrylate phosphate/acrylates copolymer; ammonium acrylates/acrylonitrogens copolymer; ammonium acrylates copolymer; ammonium alginate; ammonium VA/acrylates copolymer; amp-acrylates/diacetoneacrylamide copolymer; amp-acrylates copolymer; ampd-acrylates/diacetoneacrylamide copolymer; bayberry wax; behenyl/isostearyl beeswax; benzoic acid/phthalic anhydride/pentaerythritol/neopentyl glycol/palmitic acid copolymer; butadiene/acrylonitrile copolymer; butoxy chitosan; butyl benzoic acid/phthalic anhydride/trimethylolethane copolymer; butyl benzyl phthalate; butyl ester of ethylene/MA copolymer; butyl ester of PVM/MA copolymer; butyl phthalyl butyl glycolate; butylated polyoxymethylene urea; butylated PVP; calcium/sodium PVM/MA copolymer; calcium carrageenan; camphor; candelilla cera; carboxymethyl chitosan succinamide; carboxymethyl hydroxyethylcellulose; carnauba; cellulose acetate; cellulose acetate butyrate; cellulose acetate propionate; cellulose gum; cera alba; ceratonia siliqua; cetyl hydroxyethylcellulose; chitosan succinamide; collodion; colophonium; copaifera officinalis; copal; corn starch/acrylamide/sodium acrylate copolymer; croscarmellose; cyanopsis tetragonalba; desamido collagen; dibutyl adipate; dibutyl lauroyl glutamide; dibutyl phthalate; dibutyl sebacate; dicapryl adipate; dicetyl adipate; diethyl phthalate; diethylene glycolamine/epichlorohydrin/piperazine copolymer; diglycol/chdm/isophthalates/sip copolymer; dilinoleic acid/ethylenediamine copolymer; dimethicone/mercaptopropyl methicone copolymer; dimethicone/sodium PG-propyldimethicone thiosulfate copolymer; dimethyl phthalate; dioctyl adipate; dioctyl phthalate; dioctyl sebacate; dioctyl succinate; dmapa acrylates/acrylic acid/acrylonitrogens copolymer; dmhf; dodecanedioic acid/cetearyl alcohol/glycol copolymer; ethyl cyanoacrylate; ethyl ester of PVM/MA copolymer; ethyl tosylamide; ethylcellulose; ethylene/acrylic acid/VA copolymer; ethylene/acrylic acid copolymer; ethylene/calcium acrylate copolymer; ethylene/MA copolymer; ethylene/magnesium acrylate copolymer; ethylene/propylene copolymer; ethylene/sodium acrylate copolymer; ethylene/VA copolymer; ethylene/zinc acrylate copolymer; flexible collodion; gellan gum; glyceryl alginate; glyceryl hydrogenated rosinate; glyceryl polyacrylate; glyceryl rosinate; glycosaminoglycans; guar hydroxypropyltrimonium chloride; gutta percha; ydrogenated styrene/butadiene copolymer; hydrogenated styrene/methyl styrene/indene copolymer; ydrolyzed collagen; hydrolyzed elastin; hydrolyzed keratin; hydroxybutyl methylcellulose; hydroxyethyl ethylcellulose; hydroxyethylcellulose; hydroxylated lanolin; hydroxypropyl guar; hydroxypropyl methylcellulose; hydroxypropylcellulose; isobutylene/sodium maleate copolymer; isopropyl ester of PVM/MA copolymer; lanolin cera; lauryl acrylate/VA copolymer; lithium oxidized polyethylene; maltodextrin; melamine/formaldehyde resin; methacryloyl ethyl betaine/acrylates copolymer; methyl hydrogenated rosinate; methyl methacrylate crosspolymer; methyl rosinate; mustela; natto gum; nitrocellulose; nonoxynyl hydroxyethylcellulose; oat beta glucan; octylacrylamide/acrylates/butylaminoethyl methacrylate copolymer; oleoyl hydrolyzed collagen; ouricury wax; oxidized polypropylene; PEG-8/SMDI copolymer; PEG-crosspolymer; pentaerythrityl hydrogenated rosinate; pentaerythrityl rosinate; phthalic anhydride/adipic acid/castor oil/neopentyl glycol/PEG-3/trimethylolpropane copolymer; phthalic anhydride/benzoic acid/trimethylolpropane copolymer; phthalic anhydride/butyl benzoic acid/propylene glycol copolymer; phthalic anhydride/glycerin/glycidyl decanoate copolymer; phthalic anhydride/trimellitic anhydride/glycols copolymer; polyacrylamide; polyacrylamidomethylpropane sulfonic acid; polyacrylic acid; polybutylene terephthalate; polychlorotrifluoroethylene; polydimethylaminoethyl methacrylate; polyethylacrylate; polyethylene; polyethylene terephthalate; polyglucuronic acid; polyglycerylmethacrylate; polyisobutene; polymethacrylamidopropyltrimonium chloride;

polymethyl acrylate; polymethyl methacrylate; polyoxyisobutylene/methylene urea copolymer; polypropylene; Polyquaternium-1; Polyquaternium-10; Polyquaternium-11; Polyquaternium-12; Polyquaternium-13; Polyquaternium-14; Polyquaternium-15; Polyquaternium-16; Polyquaternium-17; Polyquaternium-18; Polyquaternium-19; Polyquaternium-2; Polyquaternium-20; Polyquaternium-22; Polyquaternium-24; Polyquaternium-27; Polyquaternium-28; Polyquaternium-29; Polyquaternium-30; Polyquaternium-31; Polyquaternium-32; Polyquaternium-33; Polyquaternium-34; Polyquaternium-35; Polyquaternium-36; Polyquaternium-37; Polyquaternium-39; Polyquaternium-4; Polyquaternium-42; Polyquaternium-5; Polyquaternium-6; Polyquaternium-7; Polyquaternium-8; Polyquaternium-9; Polysilicone-6; polystyrene; polyurethane; polyvinyl acetate; polyvinyl alcohol; polyvinyl butyral; polyvinyl imidazolinium acetate; polyvinyl laurate; polyvinyl methyl ether; potassium acetate; potassium carrageenan; potassium hyaluronate; PPG-26/TDI copolymer; PPG-51/SMDI copolymer; procollagen; propylene glycol diundecanoate; PVM/MA copolymer; PVP; PVP/decene copolymer; PVP/dimethylaminoethylmethacrylate copolymer; PVP/eicosene copolymer; PVP/hexadecene copolymer; PVP/VA/itaconic acid copolymer; PVP/VA/vinyl propionate copolymer; PVP/va copolymer; rosin acrylate; rosin hydrolyzed collagen; rubber latex; shellac; shellac cera; sodium acrylate/vinyl alcohol copolymer; sodium carrageenan; sodium dvb/acrylates copolymer; sodium polyacrylate starch; sodium polymethacrylate; sodium polystyrene sulfonate; sodium PVM/MA/decadiene crosspolymer; sodium styrene/acrylamide copolymer; sodium styrene/acrylates copolymer; sodium tauride acrylates/acrylic acid/acrylonitrogens copolymer; soluble collagen; starch/acrylates/acrylamide copolymer; starch diethylaminoethyl ether; steareth-10 allyl ether/acrylates copolymer; stearylvinyl ether/MA copolymer; styrax benzoin; styrax benzoin; styrene/acrylates/acrylonitrile copolymer; styrene/acrylates/ammonium methacrylate copolymer; styrene/allyl benzoate copolymer; styrene/MA copolymer; styrene/pvp copolymer; sucrose acetate isobutyrate; sucrose benzoate; sucrose benzoate/sucrose acetate isobutyrate/butyl benzyl phthalate/methyl methacrylate copolymer; sucrose benzoate/sucrose acetate isobutyrate/butyl benzyl phthalate; copolymer; sucrose benzoate/sucrose acetate isobutyrate copolymer; TEA-acrylates/acrylonitrogens copolymer; tosylamide/epoxy resin; tosylamide/formaldehyde resin; triacetin; tributyl citrate; tributylcresylbutane; tricetyl phosphate; tricontanyl PVP; trimethylpentanediol/isophthalic acid/trimellitic anhydride copolymer; tromethamine acrylates/acrylonitrogens copolymer; VA/butyl maleate/isobornyl acrylate copolymer; VA/crotonates/methacryloxybenzophenone-1 copolymer; VA/crotonates/vinyl neodecanoate copolymer; VA/crotonates/vinyl propionate copolymer; VA/crotonates copolymer; VA/dbm copolymer; VA/isobutyl maleate/vinyl neodecanoate copolymer; VA/vinyl butyl benzoate/crotonates copolymer; vinyl acetate; vinyl caprolactam/pvp/dimethylaminoethyl methacrylate copolymer.

The agent can also be an anti-nerve gas agent. An anti-nerve gas agent is an agent which counteracts the effects of a nerve gas agent. Examples of anti-nerve gas agents include: organophosphate hydrolases such as phosphotriesterase; pyridostigmine, physostigmine, eptastigmine, pralidoxime-2-chloride (2-PAM); potassium 2,3-butadion monoximate; potassium permanganate; sodium phenolate or sodium cresolate; chlorinated lime and magnesium oxide; chloramines; bentonite; and a mixture of atropine and PAM.

The agent can also be a vitamin including vitamin A, vitamin B, vitamin C, vitamin D, vitamin E, and their provitamin counterparts.

As mentioned above, the agent may be a pharmaceutical agent.

When administered the pharmaceutical agents of the invention are applied in pharmaceutically acceptable amounts and in pharmaceutically acceptable compositions. Such preparations may routinely contain salts, buffering agents, preservatives, compatible carriers and optionally other therapeutic or nontherapeutic ingredients. When used in medicine, the salts should be pharmaceutically acceptable, but nonpharmaceutically acceptable salts may conveniently be used to prepare pharmaceutically acceptable salts thereof and are not excluded from the scope of the invention.

Examples of categories of pharmaceutical agents include: analgesic; amino acid; antagonist; anti-acne agent; antiallergic; anti-asthmatic; antibacterial; anticholinergic; antifungal; antiglaucoma agent; antihistamine; anti-infective; anti-infective, topical; antiinflammatory; antikeratinizing agent; antimicrobial; antimycotic; antineoplastic, antineutropenic; antiproliferative; antipruritic; antiseborrheic; carbonic anhydrase inhibitor; cholinergic; cholinergic agonist; diagnostic aids; ectoparasiticide; fluorescent agent; glucocorticoid; hair growth stimulant; histamine H2 receptor antagonists; immunizing agent; immunomodulator; immunoregulator; immunostimulant; immunosuppressant; keratolytic; mucosal protective agent; radioactive agents; wound healing agent.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin.

Antiacne: Adapalene; Erythromycin Salnacedin; Inocoterone Acetate.

Antiallergic: Amlexanox; Astemizole; Azelastine Hydrochloride; Eclazolast; Minocromil; Nedocromil; Nedocromil Calcium; Nedocromil Sodium; Nivimedone Sodium; Pemirolast Potassium; Pentigetide; Pirquinozol; Poisonoak Extract; Probicromil Calcium; Proxicromil; Repirinast; Tetrazolast Meglumine; Thiazinamium Chloride; Tiacrilast; Tiacrilast Sodium; Tiprinast Meglumine; Tixanox.

Antiasthmatic: Ablukast; Ablukast Sodium; Azelastine Hydrochloride; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine; Quazolast; Repirinast; Ritolukast; Sulukast; Tetrazolast Meglumine; Tiaramide Hydrochloride; Tibenelast Sodium; Tomelukast; Tranilast; Veriukast; Verofylline; Zarirlukast.

Antibacterial: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefmetazole; Cefmetazole Sodium; Cefonicid Monosodium; Cefonicid Sodium; Cefoperazone Sodium; Cefloranide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thianphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Anticholinergic: Alverine Citrate; Anisotropine Methylbromide; Atropine; Atropine Oxide Hydrochloride; Atropine Sulfate; Belladonna; Benapryzine Hydrochloride; Benzetimide Hydrochloride; Benzilonium Bromide; Biperiden; Biperiden Hydrochloride; Biperiden Lactate; Clidinium Bromide; Cyclopentolate Hydrochloride; Dexetimide; Dicyclomine Hydrochloride; Dihexyverine Hydrochloride; Domazoline Fumarate; Elantrine; Elucaine; Ethybenztropine; Eucatropine Hydrochloride; Glycopyrrolate; Heteronium Bromide; Homatropine Hydrobromide; Homatropine Methylbromide; Hyoscyamine; Hyoscyamine Hydrobromide; Hyoscyamine Sulfate; Isopropamide Iodide; Mepenzolate Bromide; Methylatropine Nitrate; Metoquizine; Oxybutynin Chloride; Parapenzolate Bromide; Pentapiperium Methylsulfate; Phencarbamide; Poldine Methylsulfate; Proglumide; Propantheline Bromide; Propenzolate Hydrochloride; Scopolamine Hydrobromide; Tematropium Methylsulfate; Tiquinamide Hydrochloride; Tofenacin Hydrochloride; Toquizine; Triampyzine Sulfate; Trihexyphenidyl Hydrochloride; Tropicamide.

Antifungal: Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; Zinoconazole Hydrochloride.

Antiglaucoma agent: Alprenoxime Hydrochloride; Colforsin; Dapiprazole Hydrochloride; Dipivefrin Hydrochloride; Naboctate Hydrochloride; Pilocarpine; Pirnabine.

Antihistaminic: Acrivastine; Antazoline Phosphate; Astemizole; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cinnarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylamine Succinate; Ebastine; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Terfenadine; Tripelennamine Citrate; Tripelennamine Hydrochloride; Triprolidine Hydrochloride; Zolamine Hydrochloride.

Anti-infective: Difloxacin Hydrochloride; Lauryl Isoquinolinium Bromide; Moxalactam Disodium; Omidazole; Pentisomicin; Sarafloxacin Hydrochloride; Protease inhibitors of HIV and other retroviruses; Integrase Inhibitors of HIV and other retroviruses; Cefaclor (Ceclor); Acyclovir (Zovirax); Norfloxacin (Noroxin); Cefoxitin (Mefoxin); Cefuroxime axetil (Ceftin); Ciprofloxacin (Cipro).

Anti-infective, topical: Alcohol; Aminacrine Hydrochloride; Benzethonium Chloride; Bithionolate Sodium; Bromchlorenone; Carbamide Peroxide; Cetalkonium Chloride; Cetylpyridinium Chloride; Chlorhexidine Hydrochloride; Clioquinol; Domiphen Bromide; Fenticlor; Fludazonium Chloride; Fuchsin, Basic; Furazolidone; Gentian Violet; Halquinols; Hexachlorophene; Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofurazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; Troclosene Potassium.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

Antikeratinizing agent: Doretinel; Linarotene; Peiretin.

Antimicrobial: Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine.

Antimycotic: Amorolfine.

Antineoplastic: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizclesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1 a; Interferon Gamma-1 b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentanustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan, iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinoretbine; vinxaltine; vitaxin; vorozole; zanoterone; zeniplatin; zilascorb; zinostatin stimalamer.

Anti-cancer Supplementary Potentiating Agents: Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{++}$ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Antineutropenic: Filgrastim; Lenograstim; Molgramostim; Regramostim; Sargramostim.

Antiproliferative agent: Piritrexim Isethionate.

Antiprotozoal: Amodiaquine; Azanidazole; Bamnidazole; Carnidazole; Chlortetracycline Bisulfate; Chlortetracycline Hydrochloride; Flubendazole; Flunidazole; Halofuginone Hydrobromide; Imidocarb Hydrochloride; Ipronidazole; Metronidazole; Misonidazole; Moxnidazole; Nitarsone; Partricin; Puromycin; Puromycin Hydrochloride; Ronidazole; Sulnidazole; Tinidazole.

Antipruritic: Cyproheptadine Hydrochloride; Methdilazine; Methdilazine Hydrochloride; Trimeprazine Tartrate.

Antipsoriatic: Acitretin; Anthralin; Azaribine; Calcipotriene; Cycloheximide; Enazadrem Phosphate; Etretinate; Liarozole Fumarate; Lonapalene; Tepoxalin.

Carbonic anhydrase inhibitor: Acetazolamide; Acetazolamide Sodium; Dichlorphenamide; Dorzolamide Hydrochloride; Methazolamide; Sezolamide Hydrochloride.

Cholinergic: Aceclidine; Bethanechol Chloride; Carbachol; Demecarium Bromide; Dexpanthenol; Echothiophate Iodide; Isoflurophate; Methacholine Chloride; Neostigmine Bromide; Neostigmine Methylsulfate; Physostigmine; Physostigmine Salicylate; Physostigmine Sulfate; Pilocarpine; Pilocarpine Hydrochloride; Pilocarpine Nitrate; Pyridostigmine Bromide.

Diagnostic aid: Aminohippurate Sodium; Anazolene Sodium; Arclofenin; Arginine; Bentiromide; Benzylpenicilloyl Polylysine; Butedronate Tetrasodium; Butilfenin; Coccidioidin; Corticorelin Ovine Triflutate; Corticotropin, Repository; Corticotropin Zinc Hydroxide; Diatrizoate Meglumine; Diatrizoate Sodium; Diatrizoic Acid; Diphtheria Toxin for Schick Test; Disofenin; Edrophonium Chloride; Ethiodized Oil; Etifenin; Exametazime; Ferristenc; Ferumoxides; Ferumoxsil; Fluorescein; Fluorescein Sodium; Gadobenate Dimeglumine; Gadoteridol; Gadodiamide; Gadopentetate Dimegiumine; Gadoversetamide; Histoplasmin; Impromidine Hydrochloride; Indigotindisulfonate Sodium; Indocyanine Green; Iobenguane Sulfate I 123; Iobenzamic Acid; Iocarmate Meglumine; Iocarmic Acid; Iocetamic Acid; Iodamide; Iodamide Meglumine; Iodipamide Meglumine; Iodixanol; Iodoxamate Meglumine; Iodoxamic Acid; Ioglicic Acid; Ioglucol; Ioglucomide; Ioglycamic Acid; Iogulamide; Iohexol; Iomeprol; Iopamidol; Iopanoic Acid; Iopentol; Iophendylate; Iprofenin; Iopronic Acid; Ioprocemic Acid; Iopydol; Iopydone; Iosefamic Acid; Ioseric Acid; Iosulamide Meglumine; Iosumetic Acid; Iotasul; Iotetric Acid; Iothalamate Meglumine; Iothalamate Sodium; Iothalamic Acid; Iotrolan; Iotroxic Acid; Ioversol; Ioxaglate Meglumine; Ioxagiate Sodium; Ioxaglic Acid; Ioxilan; Ioxotrizoic Acid; Ipodate Calcium; Ipodate Sodium; Isosulfan Blue; Leukocyte Typing Serum; Lidofenin; Mebrofenin; Meglumine; Metrizamide; Metrizoate Sodium; Metyrapone; Metyrapone Tartrate; Mumps Skin Test Antigen; Pentetic Acid; Propyliodone; Quinaldine Blue; Schick Test Control; Sermorelin Acetate; Sodium Iodide I 123; Sprodiamide; Stannous Pyrophosphate; Stannous Sulfur Colloid; Succimer; Teriparatide Acetate; Tetrofosmin; Tolbutamide Sodium; Tuberculin; Tryropanoate Sodium; Xylose.

Ectoparasiticide: Nifluridide; Permethrin.

Glucocorticoid: Amcinonide; Beclomethasone Dipropionate; Betamethasone; Betamethasone Acetate; Betamethasone Benzoate; Betamethasone Dipropionate; Betamethasone Sodium Phosphate; Betamethasone Valerate; Carbenoxolone Sodium; Clocortolone Acetate; Clocortolone Pivalate; Cloprednol; Corticotropin; Corticotropin, Repository; Corticotropin Zinc Hydroxide; Cortisone Acetate; Cortivazol; Descinolone Acetonide; Dexamethasone; Dexamethasone Sodium Phosphate; Diflucortolone; Diflucortolone Pivalate; Flucloronide; Flumethasone; Flumethasone Pivalate; Flunisolide; Fluocinolone Acetonide; Fluocinonide; Fluocortolone; Fluocortolone Caproate; Fluorometholone; Fluperolone Acetate; Fluprednisolone; Fluprednisolone Valerate; Flurandrenolide; Formocortal; Hydrocortisone; Hydrocortisone Acetate; Hydrocortisone Buteprate; Hydrocortisone Butyrate; Hydrocortisone Sodium Phosphate; Hydrocortisone Sodium Succinate; Hydrocortisone Valerate; Medrysone; Methylprednisolone; Methylprednisolone Acetate; Methylprednisolone Sodium Phosphate; Methylprednisolone Sodium Succinate; Nivazol; Paramethasone Acetate; Prednicarbate; Prednisolone; Prednisolone Acetate; Prednisolone Hemisuccinate; Prednisolone Sodium Phosphate; Prednisolone Sodium Succinate; Prednisolone Tebutate; Prednisone; Prednival; Ticabesone Propionate; Tralonide; Triamcinolone; Triamcinolone Acetonide; Triamcinolone Acetonide Sodium; Triamcinolone Diacetate, Triamcinolone Hexacetonide.

Hair growth stimulant: Minoxidil.

Histamine H2 receptor antagonists: Ranitidine (Zantac); Famotidine (Pepcid); Cimetidine (Tagamet); Nizatidine (Axid).

Immunizing agent: Antirabies Serum; Antivenin (Latrodectus mactans); Antivenin (Micrurus Fulvius); Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; $Rh_o(D)$ Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Yellow Fever vaccine; Vaccinia Immune Globulin; Varicella-Zoster Immune Globulin.

Immunomodulator: Dimepranol Acedoben; Imiquimod; Interferon Beta-1b; Lisofylline; Mycophenolate Mofetil; Prczatide Copper Acetate.

Immunoregulator: Azarole; Fanetizole Mesylate; Frentizole; Oxamisole Hydrochloride; Ristianol Phosphate; Thymopentin; Tilomisole.

Immunostimulant: Loxoribine; Teceleukin.

Immunosuppressant: Azathioprine; Azathioprine Sodium; Cyclosporine; Daltroban; Gusperimus Trihydrochloride; Sirolimus; Tacrolimus.

Mucolytic: Acetylcysteine; Carbocysteine; Domiodol.

Mucosal Protective agents: Misoprostol (Cytotec).

Radioactive agent: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine I 131; Tolpovidone I 131; Triolein I 1125; Triolein I 131.

Wound healing agent: Ersofermin.

The invention further provides methods of treating a subject to attach microparticles to a tissue of the subject by contacting a tissue of the subject with a microparticle having surface available transglutaminase substrate reactive groups and allowing the microparticles to remain in contact with the tissue for a time sufficient to permit a layer of microparticles to covalently attach to the tissue. The reactive groups are present on the surface of the microparticle in an amount sufficient to attach the microparticle to the skin surface in the presence of transglutaminase. The transglutaminase may be endogenous (i.e., provided by the tissue to which the microparticle is applied) or exogenous. The quantity of surface available reactive groups which is a "sufficient amount" will vary depending upon whether the transglutaminase is endogenous or exogenous, as described above. A sufficient amount of surface available reactive groups can be achieved, for example, by increasing in the microparticles the number of residues which have the reactive groups, or by increasing in the microparticles (and particularly at the surface) the number of reactive groups by preventing their chemical reaction with other reactive groups either intrinsic or extrinsic to the microparticle. Whether the particles have a "sufficient amount" of surface available reactive groups can be tested as described herein. Preferably, the tissue is an external surface such as skin, nails or hair. In important embodiments, the tissue is a skin surface.

As used herein, a subject may be a human, non-human primate, cow, horse, pig, sheep, goat, dog, cat, rabbit or rodent. In all embodiments, human subjects are preferred.

The subject to be treated according to the methods of the invention is one who will benefit from the treatment with the microparticles. Such treatment can be prophylactic, such as when the microparticles contain a sunscreen agent or a UV filter, or it can be therapeutic, such as when the microparticles contain an anti-fungal agent. Additionally, the subject may be one in need of cosmetic benefit, in which case the microparticles may contain a cosmetic such as a moisturizer or a skin tanning agent.

The term "contacting" as used herein refers to a physical interaction between the skin surface and the microparticles, or, alternatively, the suspension in which the microparticles are provided. Preferably, "contacting" embraces placing the microparticles in close enough proximity to the skin to allow for attachment of the microparticles to the skin via the surface available transglutaminase substrate reactive groups. Microparticles may be applied to the skin alone, or alternatively, they may be provided together with a pharmaceutically acceptable carrier. In some embodiments, the microparticles can be provided in a formulation commonly intended for application to an external surface, such as a lotion, gel, ointment, jelly, cream, shampoo, detergent or spray (e.g., aerosol).

After contacting the microparticles with, for example, the skin surface, it is necessary to allow the microparticles to remain in contact with the skin surface for a time sufficient to permit a layer of microparticles to covalently attach to the tissue. When the microparticles are contacted with the skin surface they generally will distribute randomly throughout a volume above the skin surface, or if small enough in size, throughout a volume under the outermost layer of skin. This will also be the case should the microparticles be provided in a topical formulation such as an ointment. Not all the microparticles will contact the skin surface initially, however with time, a sufficient number of microparticles will settle closer to the skin surface until the point where their surface available reactive groups will react with corresponding active groups on the skin, resulting in a covalent bond that tethers the microparticles to the skin. If the microparticles of small enough, they will distribute randomly below the outermost layer of skin and preferably in proximity to the layer of living skin cells. A "sufficient number of microparticles" is that number required to provide an effective amount of the active agent to the tissue (e.g., the skin surface).

The microparticles, whether applied to the tissue in an isolated form or as part of a formulation, are allowed to settle towards the tissue and thereby form a layer. A layer of microparticles is that amount and distribution of microparticles that is enough to provide distribution of active agent to the skin in amounts sufficient to achieve the prophylactic, therapeutic or cosmetic purpose of the agent. The microparticles need not be adjacent to one another in the layer, nor must they be in the same plane (as described herein) provided their distribution above, within or below the outermost layer of skin allows the active agent to be distributed sufficiently. As an example, when the active agent is a sunscreen, it is desirable that it be applied uniformly distributed over an entire area of skin in order to provide maximal effect. It may not be necessary, however, that the sunscreen containing microparticles be physically touching each other, provided each microparticle is capable of providing sufficient amounts of sunscreen for a particular surface area. As a further example, if the active agent is a cosmetic, it may be desirable to form a layer of microparticles over a defined surface area in order to provide the cosmetic solely to the discrete area. The layer of microparticles may be a volume of space over the tissue occupied by the microparticles. The microparticles may be, but need not be, in a planar arrangement. By a planar arrangement, it is meant that the microparticles are equidistant from the surface of the tissue. Conversely, a non-planar arrangement indicates that the microparticles are differentially spaced away from the surface of the tissue. The distance of the microparticle from the surface of the tissue may depend upon the location of the microparticle reactive groups which have covalently linked to the tissue. If these are located on long pendent chains, the microparticle may not be contacting the tissue surface at all. If instead the reactive groups are directly on the surface of the microparticle, then the microparticle may be contacting the tissue surface.

If the method relies on the activity of endogenous transglutaminase alone, then only the microparticles need be applied to the skin surface. However, if the method requires the use of exogenous transglutaminase, then both microparticles and exogenous transglutaminase are applied to the skin surface and allowed to remain in contact with the skin for a time sufficient to permit the layer of microparticles to covalently attach to the skin.

In some embodiments, it may be desired that the microparticles penetrate the skin to at least the layer of living cells. Thus, rather than being located on the skin surface, the particles may be located within the skin surface. In these latter embodiments, it may also be desirable to use microparticles which possess both carboxamide and aliphatic amine reactive groups and to rely on the action of endogenous transglutaminase. Once the microparticles enter the layer of living cells and are exposed to endogenous transglutaminase, they are likely to crosslink with each other (i.e., covalent bonds may be formed between aliphatic amines on one microparticle and carboxamides on another). The crosslinked microparticles may then become so large that they are unable to exit the layer of living cells and are thus retained in this layer. In some embodiments, the microparticles may be those which degrade following the treatment period.

If the microparticles are provided to the skin surface as part of a formulation such as those listed above, it is important that the majority of the active agent does not exit (i.e., leach) from the microparticle and into the formulation prior to contact with the skin. Preferably, the active agent is not substantially soluble in the formulation. Instead, the agent will exit the microparticle only upon contact with the skin. This may occur if, for example, the active agent is specifically soluble at higher temperatures (such as at the skin surface), or in the bodily secretions at the skin surface. Alternatively, the microparticle may be made from substances which are temperature or environment sensitive, so that contact with the skin but not necessarily with the formulation induces their disintegration and the subsequent release of the active agent. Thermosensitive polymers in the form of poly(ether-ester) block copolymers are reported by Cha et al., in U.S. Pat. No. 5,702,717.

The microparticles may optionally be combined with a pharmaceutically-acceptable carrier to form a pharmaceutical preparation. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being commingled with the agents of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compositions and pharmaceutical preparations may be administered in effective amounts. An effective amount, in general, means that amount necessary to achieve the purpose for which the active agent is applied. The effective amount will depend upon the mode of administration, the particular condition being treated, the severity of the condition, the needs of the patient, and the desired outcome. It will also depend upon, as discussed above, the stage of the condition, the age and physical condition of the subject, frequency of treatment and mode of treatment, the nature of concurrent therapy, if any, and like factors well known to the medical practitioner. If the active agent is a pharmaceutical agent, then the amount is that amount necessary to delay the onset of slow the progression of, halt altogether the onset or progression of, or diagnose a particular condition being treated. In the case of a cosmetic agent, the effective amount will be that amount necessary to achieve the desired cosmetic result. In the case of a sunscreen agent, an effective amount will be that amount necessary to achieve suitable protection from the sun as is conventional.

Generally, doses of active compounds of the present invention would be from about 0.01 mg/kg per day to 1000 mg/kg per day. It is expected that doses ranging from 1–500 mg/kg, and preferably doses ranging from 1–100 mg/kg, and even more preferably doses ranging from 1–50 mg/kg, will be suitable. A variety of administration routes are available, although topical routes are preferred. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal or interdermal routes.

The active agents, the microparticles and the formulations in which they are provided can be in solid, semi-solid or liquid form. Solid forms include for example, powders, granules and flakes. Semi-solid forms include, for example, gels, creams, gelatins and ointments. Formulations for topical administration are known to those of ordinary skill in the art and, in most cases, are commercially available from suppliers such as Paddock Laboratories and Gallipot. Information on topically active and inactive agents, and their commercial suppliers is available from various trade manuals, most particularly, Remington's Pharmaceutical Sciences, United States Pharmacopoeia (USP), National Formulary (NF), Merck Index, Physician's Desk Reference (PDR) and Chemical Abstracts. The invention also provides kits. Referring to an exemplary kit in FIG. 1, the kit is a package 10 comprising a housing 12 holding a first container 14, a second container 16 and a third container 18. The kits optionally may be comprised of a single container which houses the microparticle compositions described above, either alone, in a pharmaceutically acceptable carrier or in a topically applied formation. Generally, this latter category of kits is recommended when endogenous transglutaminase is used. The kit may alternatively contain more than one container in which case they are provided in a package which houses the containers. A second container may be provided which contains transglutaminase. The transglutaminase preferably is stored in the presence of a chelating agent such as EDTA, and any of the other containers housed in the packaging may contain calcium for activating the transglutaminase when applied to the tissue. A third container may also be provided which contains, for example, a linking molecule for preparing the surface of the body tissue for application of the microparticles. The various containers may also contain preservatives, buffers, vehicles, and the like, as is conventional. The kit also houses instructions for using the materials according to the invention, particularly for the topical administration of the microparticles. The instructions may be provided separately from the containers (e.g., on a sheet of paper enclosed in the kit) or on one of the containers (e.g., text on the outside surface of a container).

EXAMPLES

Example 1

Durable Suntan Preparation and Kit

A kit is provided for producing a durable sunscreen. The kit includes as a first component a conjugate of a low molecular weight sunscreen agent and a linking agent. This component is an aqueous solution, pH 6.4 of 50 mM polylysyl-methoxy-2-ethylhexyl-cinnamate, 0.1 v % propylene glycol, 0.5 mM, EDTA, 0.1 wt % BHT, 0.1 wt % potassium sorbate, 0.05 wt % polysorbate 20 and 80 and 1 mM sodium laurylethcr sulfate. Component 2 of the kit is a calcium chloride activator solution. This is an aqueous solution at about 25 mM calcium chloride. Component 3 of the kit is lyophilized transglutaminase. The lyophilized preparation can contain 10 mg of recombinant tissue transglutaminase in 2% sucrose, 0.1 mM EDTA, and 5 mM glycine buffer, pH 7.2.

Three vials containing the three kit components are opened. About 10 mL of component 1 is added to 10 mg of component 3, and the combination is mixed by swirling. Then this combination is added to about 90 mL of component 1. Finally, about 10 mL of component 2 is added to the mixture, with this final combination mixed by gentle swirling. The mixture then is applied to a washed and scraped skin surface. The mixture is uniformly spread on the skin and allowed to remain for ten minutes. The excess solution is removed by washing.

Example 2

Durable Topical Antifungal Preparation and Kit

A kit is provided for producing durable antifungal protection. The kit contains three components. Component 1 is a conjugate of an antifungal agent and a linking agent. This component is an aqueous solution, pH 6.4, containing 0.01 wt % polylysyl-amphotericin B conjugate, 10 v % ethanol, 0.1 v % propylene glycol, 0.5 mM EDTA, 0.1 wt % BHT. Component 2 is a calcium chloride activator solution as described for Example 1. Component 3 is a lyophilized transglutaminase preparation as described in Example 1. The three containers containing components 1, 2 and 3 are opened. Ten mL of component 1 is added to component 3, and they are mixed by swirling. The mixture then is added to about 90 mL of component 1. To this mixture is added component 2. This final combination is mixed by gentle swirling. After this, the material is applied to the surface of skin as described in Example 1.

Example 3

Long-Term Protective Preparation for Anticholinesterase Nerve Gas and Kit

A kit for providing long-term protection from anticholinesterase nerve gas is provided. Component 1 of the kit includes recombinant cholinesterase coupled to biotin (e.g., by reaction in the presence of N.N. succinimide). Component 2 is polyglutamine coupled to avidin. Component 2 is applied to the surface of the skin in the presence of transglutaminase, as described above in connection with Examples 1 and 2. After the avidin is coupled to the skin via the polyglutamine, then component 1 is added to bind the biotin to the avidin, thereby coupling the cholinesterase to the skin.

Example 4

A Mousse for Thickening Hair

A dispensing can with three reservoirs (a calcium ion solution, a transglutaminase solution and a hair bulking or thickening agent such as a mucopolysaccharide linked to polyglutamine) is provided. The three solutions are mixed, as is conventional with such dispensing cans, as they are being applied onto tissue such as hair. The mousse can be combed through the hair, left on the hair for at least ten minutes, and then rinsed.

Example 5

It has been shown in previous studies that polyglutamine attached to other peptides remains an excellent substrate of transglutaminase. Under optimal conditions, virtually all of the glutamine residues acted as amine acceptors in the reaction with an aliphatic amine, and lengthening the sequence of polyglutamine increases the reactivity of each glutamine residue. In the presence of transglutaminase, peptides containing polyglutamine become cross-linked to polylysine. The details of the reaction conditions and the manner of applying labels whereby the reaction may be visualized under UV light are described in detail in Kahlem et al., *Proc. Natl. Acad. Sci. USA*, 1996 93:14580–14585 (Appendix A). The same polyglutamines, but attached to agents as described herein, and, in general, the same conditions as described in Kahlem et al. may be applied in the above-described examples and, in general, in the practice of the present invention. The disclosure of this reference, as well as any other reference mentioned herein, is incorporated by reference in its entirety.

Example 6

Polyglutamine Containing a Fluorescent Marker is Covalently Attached to the Surface of the Skin through the Action of Transglutaminase A. Mouse was epilated. Seven days later, a concentrated reaction solution containing guinea pig transglutaminase, dansyl labeled polyglutamine and $Ca^{2+}$ at 10 mM was applied to the left side. The control (right side) was pretreated for 10 mins with 100 mM cystamine, the excess liquid was drained and the same reaction solution containing 25 mM cystamine was applied. After 30 minutes, both sites were washed with a solution of 1% SDS. The mouse was then photographed under UV illumination (312 nm). The left side shows strong fluorescence of dansyl polyglutamine whereas the right side shows very weak fluorescence.

B. Same mouse was photographed again five days later. There is still considerable fluorescence at the site of enzymatic coupling, but the control fluorescence has virtually disappeared.

Reaction Solution

1 $\mu$l buffer containing 100 $\mu$M Tris pH8.2, 10 mM $CaCl_2$, and 10 mM DTT

3 $\mu$l dansylated polyglutamine (5 uM)

3 $\mu$l (13.3 mU/$\mu$l) partially purified guinea pig transglutaminase

It should be understood that the foregoing is merely a detailed description of certain preferred embodiments. It therefore should be apparent to those skilled in the art that various modification and equivalents can be made without departing from the spirit or scope of the invention. It is intended to encompass all such modifications within the scope of the appended claims.

All references, patents and patent applications recited in this application are incorporated in their entirety herein by reference.

We claim:

1. A composition comprising
   a microparticle comprising an active agent and a polymer having transglutaminase substrate reactive groups, wherein the transglutaminase substrate reactive groups are surface available, and the polymer comprises a polymer of amino acids having at least three contiguous linked glutamines.

2. The composition of claim 1, wherein the transglutaminase substrate reactive groups are surface available in an amount sufficient to attach the microparticle to a body tissue in the presence of endogenous transglutaminase.

3. The composition of claim 1, wherein the transglutaminase substrate reactive groups are surface available in an amount sufficient to attach the microparticle to a body tissue in the presence of exogenous transglutaminase.

4. The composition of claim 1, wherein the polymer is covalently linked to a synthetic polymer.

5. The composition of claim 1, wherein the polymer comprises a polymer of amino acids and wherein at least 20% of the amino acids are glutamines.

6. The composition of claim 1, wherein the active agent is selected from the group consisting of a cosmetic agent, a bulking agent, a hair conditioning agent, a hair fixative, a sunscreen agent, a moisturizing agent, a depilatory agent, an anti-nerve gas agent, a film forming agent, a vitamin, an insect repellant, a coloring agent, a pharmaceutical agent, a ligand-receptor complex and a receptor of a ligand-receptor complex.

7. A kit comprising
a package including a container containing the composition of claim 1 and instructions for topically administering the composition to a skin surface.

8. A composition comprising
a microparticle comprising an active agent and a polymer having transglutaminase substrate reactive groups, wherein the microparticle is non-biodegradable, and the transglutaminase substrate reactive groups are surface available, and the polymer comprises a polymer of amino acids having at least three contiguous linked lysines.

9. The composition of claim 8, wherein the transglutaminase substrate reactive groups are surface available in an amount sufficient to attach the microparticle to a body tissue in the presence of endogenous transglutaminase.

10. The composition of claim 8, wherein the transglutaminase substrate reactive groups are surface available in an amount sufficient to attach the microparticle to a body tissue in the presence of exogenous transglutaminase.

11. The composition of claim 8, wherein the polymer comprises a polymer of amino acids and wherein at least 50% of the amino acids are lysine.

12. The composition of claim 8, wherein the active agent is selected from the group consisting of a cosmetic agent, a bulking agent, a hair conditioning agent, a hair fixative, a sunscreen agent, a moisturizing agent, a depilatory agent, an anti-nerve gas agent, a film forming agent, a vitamin, an insect repellant, a coloring agent, a pharmaceutical agent, a ligand-receptor complex and a receptor of a ligand-receptor complex.

13. A kit comprising
a package including a container containing the composition of claim 8 and instructions for topically administering the composition to a skin surface.

14. A method of treating a subject to attach microparticles to a body tissue of the subject comprising
contacting the body tissue in the presence of endogenous or exogenous transglutaminase with microparticles having surface available transglutaminase substrate reactive groups in an amount sufficient to attach the microparticles to the body tissue in the presence of the transglutaminase,
allowing the microparticles to remain in contact with the body tissue for a time sufficient to permit a layer of microparticles to covalently attach to the body tissue,
wherein the transglutaminase substrate reactive groups are part of a polymer, and
wherein the polymer comprises a polymer selected from the group consisting of polymers containing:

(a) at least two contiguous linked lysines,
(b) at least three contiguous linked lysines,
(c) at least four contiguous linked lysines, and
(d) at least five contiguous linked lysines.

15. The method of claim 14, wherein the polymer is a polymer containing at least two contiguous linked lysines.

16. The method of claim 14, wherein the polymer is a polymer containing at least three contiguous linked lysines.

17. The method of claim 14, wherein the polymer is a polymer containing at least four contiguous linked lysines.

18. The method of claim 14, wherein the polymer is a polymer containing at least five contiguous linked lysines.

19. The method of claim 14, wherein the endogenous or exogenous transglutaminase is endogenous transglutaminase.

20. The method of claim 14, wherein the endogenous or exogenous transglutaminase is exogenous transglutaminase.

21. The method of claim 14, wherein the body tissue is integument.

22. The method of claim 21, wherein the integument is skin.

23. The method of claim 21, wherein the integument is the surface of the eye.

24. The method of claim 21, wherein the integument is a mucous membrane.

25. The method of claim 14, wherein the body tissue is an internal tissue.

26. The method of claim 14, wherein the microparticles further comprise an active agent.

27. A method of treating a subject to attach microparticles to a body tissue of the subject comprising
contacting the body tissue in the presence of endogenous or exogenous transglutaminase with microparticles having surface available transglutaminase substrate reactive groups in an amount sufficient to attach the microparticles to the body tissue in the presence of the transglutaminase,
allowing the microparticles to remain in contact with the body tissue for a time sufficient to permit a layer of microparticles to covalently attach to the body tissue,
wherein the transglutaminase substrate reactive groups are part of a polymer, and
wherein the polymer comprises a polymer selected from the group consisting of polymers containing:

(a) at least five contiguous linked glutamines,
(b) at least ten contiguous linked glutamines,
(c) at least fifteen contiguous linked glutamines, and
(d) at least twenty contiguous linked glutamines.

28. The method of claim 27, wherein the polymer is a polymer containing at least five contiguous linked glutamines.

29. The method of claim 27, wherein the polymer is a polymer containing at least ten contiguous linked glutamines.

30. The method of claim 27, wherein the polymer is a polymer containing at least fifteen contiguous linked glutamines.

31. The method of claim 27, wherein the polymer is a polymer containing at least twenty contiguous linked glutamines.

32. The method of claim 27, wherein the endogenous or exogenous transglutaminase is endogenous transglutaminase.

33. The method of claim 27, wherein the endogenous or exogenous transglutaminase is exogenous transglutaminase.

34. The method of claim 24, wherein the body tissue is integument.

35. The method of claim 34, wherein the integument is skin.

36. The method of claim 34, wherein the integument is the surface of the eye.

37. The method of claim 34, wherein the integument is a mucous membrane.

38. The method of claim 27, wherein the body tissue is an internal tissue.

39. The method of claim 27, wherein the microparticles further comprise an active agent.

\* \* \* \* \*

UNITED STATES PATENT AND TRADEMARK OFFICE
CERTIFICATE OF CORRECTION

PATENT NO. : 6,958,148 B1
DATED : October 25, 2005
INVENTOR(S) : Howard Green et al.

It is certified that error appears in the above-identified patent and that said Letters Patent is hereby corrected as shown below:

Column 71,
Line 3, delete "24" and insert -- 27 --.

Signed and Sealed this

Seventeenth Day of January, 2006

JON W. DUDAS
*Director of the United States Patent and Trademark Office*